(«12») United States Patent
Ablordeppey

(10) Patent No.: US 10,525,050 B2
(45) Date of Patent: Jan. 7, 2020

(54) ALKYLATED TETRAHYDROISOQUINOLINES FOR BINDING TO CENTRAL NERVOUS SYSTEM RECEPTORS

(71) Applicant: Florida A&M University, Tallahassee, FL (US)

(72) Inventor: Seth Y. Ablordeppey, Tallahassee, FL (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 15/861,750

(22) Filed: Jan. 4, 2018

(65) Prior Publication Data

US 2018/0193330 A1    Jul. 12, 2018

Related U.S. Application Data

(60) Provisional application No. 62/443,053, filed on Jan. 6, 2017.

(51) Int. Cl.
*A61K 31/4725* (2006.01)
*A61P 25/00* (2006.01)
*A61K 31/55* (2006.01)

(52) U.S. Cl.
CPC .......... *A61K 31/4725* (2013.01); *A61K 31/55* (2013.01); *A61P 25/00* (2018.01)

(58) Field of Classification Search
CPC ................................................. A61K 31/4725
USPC ........................................................ 514/307
See application file for complete search history.

(56) References Cited

U.S. PATENT DOCUMENTS

| | | | | |
|---|---|---|---|---|
| 6,486,173 B2 * | 11/2002 | Cain | ..................... | C07D 209/44 514/307 |
| 7,132,547 B2 * | 11/2006 | Ishihara | ................. | A61K 31/00 548/306.4 |
| 2005/0054850 A1 * | 3/2005 | Wu | ...................... | C07D 413/14 544/238 |

FOREIGN PATENT DOCUMENTS

IN    WO 2007029078    *    3/2007    ........... C07D 401/06

OTHER PUBLICATIONS

Mokrosz, STN Abstrct of Journal of Medicinal Chemistry (1996), 39(5), 1125-9.*
Zhu, STN Abstrct of European Journal of Medicinal Chemistry (2012), 53, 124-132.*
Mokrosz, STN Abstrct ofArchiv der Pharmazie (1995), 328(7-8), 604-8.*
Bojarski, Molecules 2004, 9(3), 170-177.*
Ofori, Bioorg. Med. Chem. 24 (2016) 5730-5740.*
Venkatesh, J. Pharm. Sci. 89, 145-54 (2000) (p. 146, left column).*
Dorwald F. A. Side Reactions in Organic Synthesis, 2005, Wiley: VCH, Weinheim p. IX of Preface p. 1-15.*
Abbas et al., (2009) Psychopharmacol. 205: 119.
Adham et al., (214) N. Eur. Neuropsychopharmacol. 24: S233.
Agai-Csongor et al., (2012) Bioorg. Med. Chem. Lett. 22: 3437.
Antkiewicz-Michaluk et al., (2014) J. Neurotox. Res. 26: 85.
Artigas, F. Pharmacol. Ther. 2013, 137: 119.
Bachman & Heisey (1949) Am. Chem. Soc. 71: 1985.
Bard et al., (1993) J. Biol. Chem. 268: 23422.
Butini et al., (2009) J. Med. Chem. 52: 151.
Canale et al., (2014) Eur. J. Med. Chem. 78: 10.
Celada et al. (2013) CNS Drugs 27: 703.
Chowdhury et al., (2012) Photochem. Photobiol. B 115: 25.
Cruz, M.P. (2012) Pharmacy Ther. 37: 28.
Davies et al., (2004) CNS Drug Rev. 10: 317.
DeLeon et al., (2004) Clin. Ther. 26: 649.
Depoortere et al., (2007) Br. J. Pharmacol. 151: 253.
Dutta et al., (2004) Bioorg Med. Chem. 12: 4361.
Franklin et al., (2015) Neuropsychiatr. Dis. Treat. 11: 2143.
Gasbarri et al., (2008) Behav. Brain Res. 195: 164.
Hall & Gisler (1976) Org. Chem. 41: 3769.
Hedlund & Sutcliffe (2004) Trends Pharmacol. Sci. 25: 481.
Horiguchi et al., (2011) J. Pharmacol. Exp. Ther. 338: 605.
Hoyer et al., (2002) Pharmacol. Biochem. Behav. 71: 533.
Kalali et al., (2012) Essential CNS Drug Development; Cambridge University Press: New York; Jul. 2012.
Conn & Roth (2008) Neuropsychopharmacol. 33: 2048.
Kroeze et al., (2003) Neuropsychopharmacol. 28: 519.
Leopoldo et al., (2011) Pharmacol. Ther. 129: 120.
Lieberman, J. A. (2004) CNS Drugs 18: 251.
Liu et al., (2014) ACS Med. Chem. Lett. 5: 760.
Lovell et al., (2000). J. Med. Chem. 43: 342.
Matthys et al., (2011) Mol. Neurobiol. 43: 228.
Medina et al., (2009) J. Med. Chem. 52: 2384.
Meltzer et al., (2003) Prog. Neuropsychopharmacol. Biol. Psychiatry 27: 1159.
Meltzer, H.Y. (1999) Neuropsychopharmacol. 21: 106S.
Miller, D. D. (2004) Prim. Care Companion J. Clin. Psychiatry 6: 3.
Mozdzen et al., (2014) Eur. J. Pharmacol. 729: 107.
Muller & Homberg (2015) Behav. Brain Res. 277: 146.
Naumenko et al., (2014) CNS Neurosci. Ther. 20: 582.
Neill et al., (2016) N. Eur. Neuropsychopharmacol. 26, 3.
Newman-Tancredi & Kleven (2011) Psychopharmacology (Berl.) 216:451.

(Continued)

*Primary Examiner* — Nizal S Chandrakumar
(74) *Attorney, Agent, or Firm* — Thomas|Horstemeyer, LLP

(57) ABSTRACT

Derivatives of 1,2,3,4-tetrahydroisoquinoline (THIQ) having the general formula A-$(CH_2)_n$—B are provided, wherein A is THIQ or a substituted derivative thereof and B is an aryl, cycloalkylaryl, or cycloalkyl group, wherein A and B are linked to each other by an alkyl or substituted alkyl chain. The compounds are useful as selective ligands (agonists or antagonists) of central nervous system receptors, and in particular of the seratonin receptors. The compounds or their salts can be formulated into pharmaceutical in need thereof by any route of administration suitable for a desired treatment protocol and especially for the treatment of psychiatric disorders.

1 Claim, 15 Drawing Sheets

(56) References Cited

OTHER PUBLICATIONS

Noel et al., (2012) Bioorg. Med. Chem. Lett. 22: 3739.
Ofori et al., (2016) Bioorg. Med. Chem. 24: 3464.
Peprah et al., (2012) Bioorg. Med. Chem. 20: 1671.
Rothman et al., (2000) Circulation 102: 2836.
Sagnes et al., (2014) Eur. J. Med. Chem. 75: 159.
Sampson et al., (2014) Bioorg. Med. Chem. 22: 3105.
Shapiro et al., (2003) Neuropsychopharmacol. 28: 1400.
Silvano et al., (2010) Mol. Pharmacol. 78: 925.
Smith & Takacs (2010) Am. Chem. Soc. 132: 1740.
Vermeulen et al., (2004) J. Med. Chem. 47: 5451.
Volkow et al., (2004) Mol. Psychiatry 9: 557.
Zajdel et al., (2011) Bioorg. Med. Chem. 19: 6750.
Zhu et al., (2012) Eur. J. Med. Chem. 53: 124.

\* cited by examiner

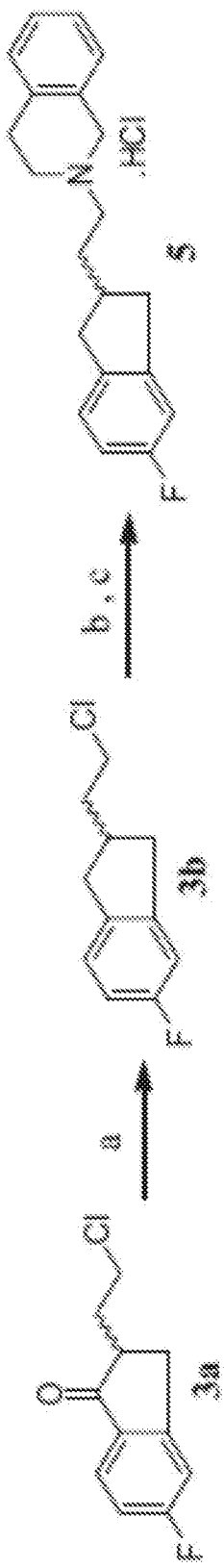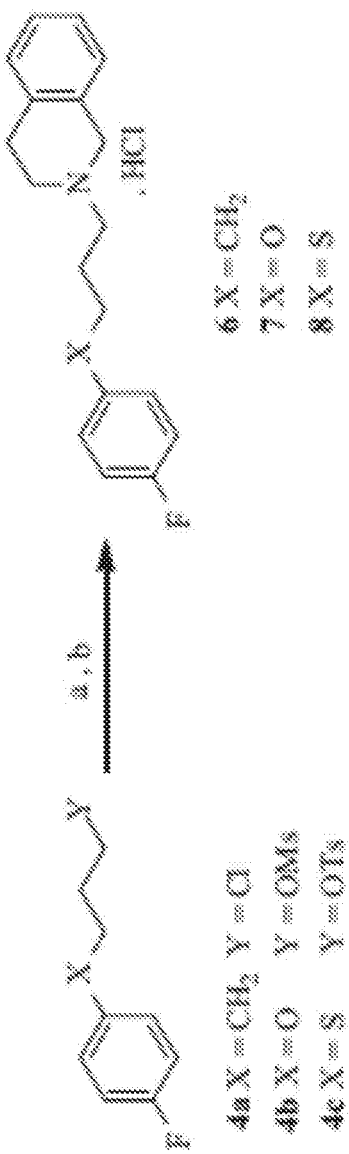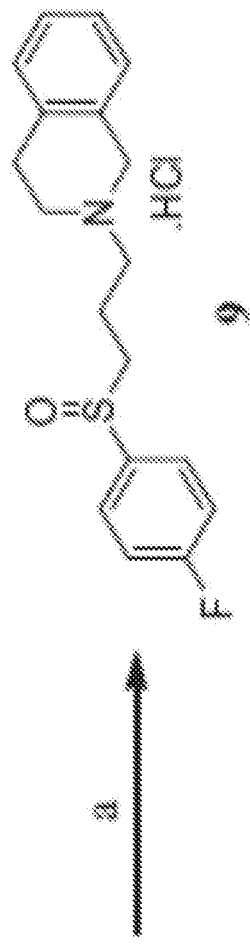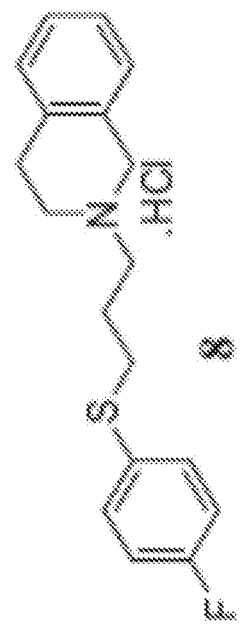
Fig. 3
Fig. 4
Fig. 5

ALKYLATED TETRAHYDROISOQUINOLINES FOR BINDING TO CENTRAL NERVOUS SYSTEM RECEPTORS

CROSS-REFERENCE TO RELATED APPLICATION

This application claims priority to and the benefit of U.S. Provisional Application 62/443,053 titled "ALKYLATED TETRAHYDROISOQUINOLINES FOR BINDING TO CENTRAL NERVOUS SYSTEM RECEPTORS" filed Jan. 6, 2017, the entire disclosure of which is incorporated herein by reference.

STATEMENT REGARDING FEDERALLY SPONSORED RESEARCH OR DEVELOPMENT

This invention was made with Government support under contracts 2SC1GM116724, G12RR03020, and 1C06-RR12512-01 awarded by the National Institutes of Health. The Government has certain rights in the invention.

TECHNICAL FIELD

The present disclosure is generally related to 1,2,3,4-tetrahydroquinoline derivatives having affinity for the central nervous system serotonin (5-HT) and dopamine (DA) receptor subtypes.

BACKGROUND

Over the years, it has become evident that pharmacotherapy of major central nervous system (CNS) diseases such as depression, bipolar disorder, schizophrenia and anxiety disorders rely on drugs that target multiple CNS receptors simultaneously (Kalali et al., (2012) *Essential CNS Drug Development;* Cambridge University Press: New York; Conn & Roth (2008) *Neuropsychopharmacol.* 33: 2048). For instance, the superior efficacy and improved side-effect profiles of atypical antipsychotics such as lurasidone, ziprasidone and aripiprazole, have been attributed to their broad spectrum of activities involving dopaminergic, serotonergic and even cholinergic neurotransmission (Davies et al., (2004) *CNS Drug Rev.* 10: 317). In the same way, antidepressants such as vilazodone, that target the reuptake of serotonin (5-HT) along with the 5-HT1A receptor are known to be fast acting, efficacious and tolerable (Cruz, M. P. (2012) *Pharmacy Ther.* 37: 28; Celada et al. (2013) *CNS Drugs* 27: 703). However, a more defined combination of pharmacological activities at these and other targets is desirable for such agents to offer optimum therapeutic benefits in treating diseases of CNS origin.

It is now well established that targeting the D2-like receptors (D2, D3 and D4, antagonists), 5-HT1A (agonists), 5-HT2A (antagonists) and 5-HT7 (antagonists) are desirable features in the pharmacotherapy for schizophrenia (Roth & Meltzer (1995) *The Role of Serotonin in Schizophrenia in Psychopharmacology: The Fourth Generation of Progress;* Bloom & Kupfer, Eds. Raven Press New York: New York; Gross & Geyer (2012) *Current Antipsychotics,* Handbook Exp. Pharmacol.; Springer-Verlag: Berlin Heidelberg, p 418). On the other hand, antidepressants may benefit from targeting the serotonin transporter (SERT), along with 5-HT1AR (agonist) and 5-HT7R (antagonist) for an improved profile (Abbas et al., (2009) *Psychopharmacol.* 205: 119; Artigas, F. *Pharmacol. Ther.* 2013, 137: 119; Stahl et al., (2013) *Curr. Drug Targets* 14: 578). With the introduction of the D2R partial agonist and functionally selective aripiprazole as a well-tolerated and effective antipsychotic, the drug development paradigm for schizophrenia has significantly shifted in a new and exciting direction (Lieberman, J. A. (2004) *CNS Drugs* 18: 251). The caveat for multiple receptor targeting has been that it may also lead to off-target activities that may culminate in unforeseen side effects. Therefore, as part of drug design strategy, there is also a focus on evaluating synthetic compounds at culprit receptors including the 5-HT2B receptors associated with valvular heart disease and the 5-HT2C and H1 weight-gain and sedation side-effects (Kroeze et al., (2003) *Neuropsychopharmacol.* 28: 519; Miller, D. D. (2004) *Prim. Care Companion J. Clin. Psychiatry* 6: 3; Opgen-Rhein et al., (2010) *Pharmacogenomics* 11: 773).

N-Alkylated tetrahydroisoquinolines have been at the center of discussion recently as key ligands for certain CNS receptors associated with major brain disorders (Vermeulen et al., (2004) *J. Med. Chem.* 47: 5451; Antkiewicz-Michaluk et al., (2014) *J. Neurotox. Res.* 26: 85; Noel et al., (2012) *Bioorg. Med. Chem. Lett.* 22: 3739). It has been previously reported that the tetrahydroisoquinoline (THIQ) moiety, appropriately substituted with arylalkyl groups such as benzothiazole alkyl groups or halobutyrophenones could produce agents that provide differential binding profiles at clinically relevant CNS receptors including serotonin (5-HT) and dopamine (DA) receptor subtypes (Zhu et al., (2012) *Eur. J. Med. Chem.* 53: 124; Ofori et al., (2016) *Bioorg. Med. Chem.* 24: 3464).

SUMMARY

Briefly described, one aspect of the disclosure encompasses embodiments of a serotonin receptor ligand having the formula:

or a salt thereof,
wherein: n=2, 3, or 4; A can be selected from the group consisting of:

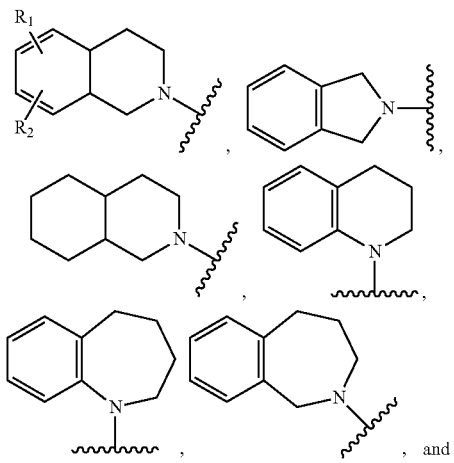

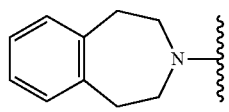

wherein if $R_1$ is H or a halogen, $R_2$ is H, and if $R_1$ is a methoxy, $R_2$ is an H or methoxy; and B is selected from the group consisting of:

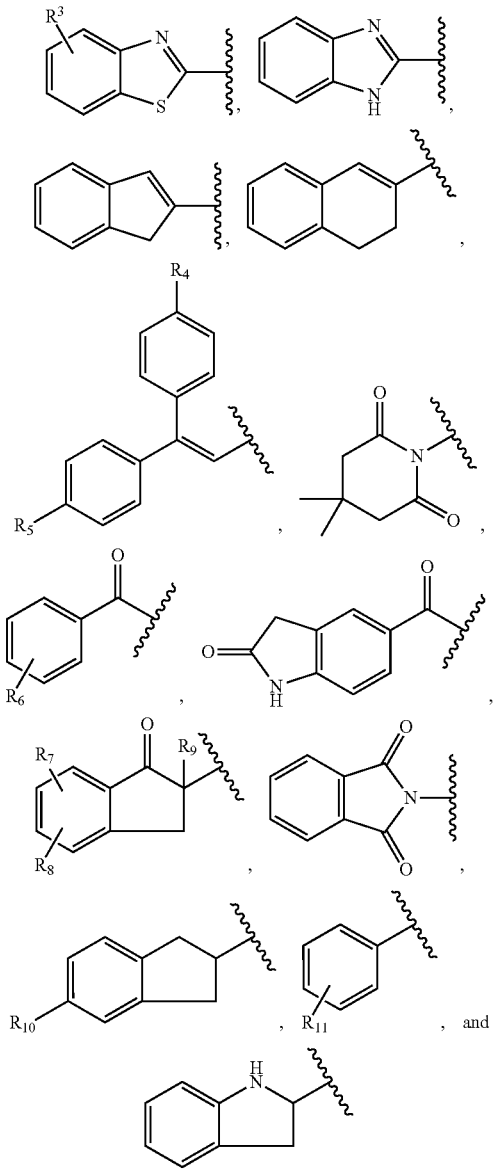

wherein: $R_3$ is H or a halogen; $R_4$ and $R_5$ are each independently H or a halogen; $R_6$ is H, CN, $CONH_2$, $H_3CO$, OH, or a halogen; $R_7$ and $R_8$ are each independently H or a halogen; $R_9$ is H, an alkyl group, or a terminally substituted alkyl group having a polar functional group, and $R_{10}$, and $R_{11}$ are each H or a halogen.

In one embodiment of this aspect of the disclosure the serotonin receptor ligand has the formula:

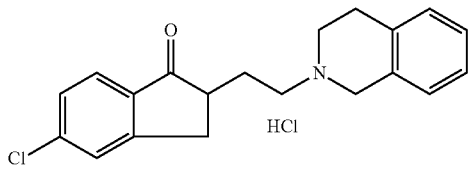 [SMILES: O=C1c2ccc(Cl)cc2CC1CCN1CCc2ccccc2C1 ; Cl]

BRIEF DESCRIPTION OF THE DRAWINGS

Further aspects of the present disclosure will be more readily appreciated upon review of the detailed description of its various embodiments, described below, when taken in conjunction with the accompanying drawings.

FIG. 3 illustrates scheme 3: Synthesis of 5-fluoro-2,3-dihydro-1H-indene analog. Reagents and conditions: (a) Zn amalgam, Conc. HCl, toluene, reflux; (b) THIQ, $K_2CO_3$/KI, DME, reflux, 12 h; (c) ethereal HCl.

FIG. 4 illustrates scheme 4: Synthesis of 4-fluorobutyrophenone analogs. Reagents and conditions: (a) THIQ, $K_2CO_3$/KI, DME, Microwave-assisted reaction (MW); (b) ethereal HCl.

FIG. 5 illustrates scheme 5: Synthesis of sulfoxide analog. Reagents and conditions: (a) m-CPBA, MeOH, 0° C. to rt.

DETAILED DESCRIPTION

Figure 1:
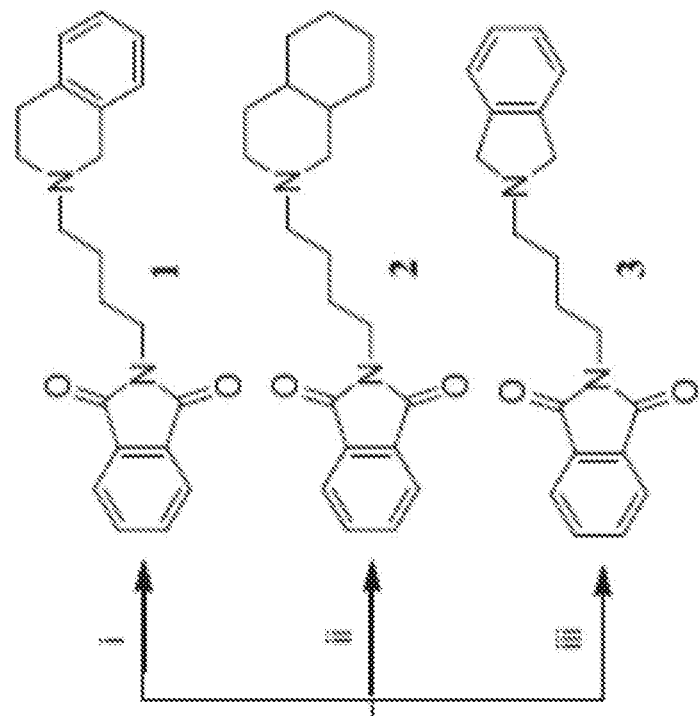
FIG. 1 illustrates scheme 1: Synthesis of isoindoline-1,3-dione analogs. Reagents and conditions: (a) 1,4-dibromobutane, DMF, 100° C.; (b) $K_2CO_3$/KI, $CH_3CN$, reflux, 12-24 h. i=THIQ; ii=decahydroisoquinoline; iii=isoindoline.
Figure 1:

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.
Abbreviations
CNS, central nervous system; THIQ, 1,2,3,4-tetrahydroisoquinoline; SAFIR, structure affinity relationship;
Definitions The term "alkoxy" as used herein refers to a linear or branched oxy-containing functional group having an alkyl portion of one to about ten carbon atoms, such as a methoxy functional group, which may be substituted. In aspects of the disclosure an alkoxy functional group can comprise about 1-10, 1-8, 1-6 or 1-3 carbon atoms. In embodiments of the disclosure, an alkoxy functional group can comprise about 1-6 carbon atoms and includes a $C_1$-$C_6$ alkyl-O— group wherein $C_1$-$C_6$ alkyl has the meaning set out herein. Examples of alkoxy functional groups include without limitation methoxy, ethoxy, propoxy, butoxy, isopropoxy and tert-butoxy alkyls. An "alkoxy" functional group may, optionally, be substituted with one or more substitutents disclosed herein including alkyl atoms to provide "alkylalkoxy" functional groups; halo atoms, such as fluoro, chloro or bromo, to provide "haloalkoxy" functional groups (e.g. fluoromethoxy, chloromethoxy, trifluoromethoxy, difluoromethoxy, trifluoroethoxy, fluoroethoxy, tetrafluoroethoxy, pentafluoroethoxy, and fluoropropox) and "haloalkoxyalkyl" functional groups (e.g. fluoromethoxymethyl, chloromethoxyethyl, trifluoromethoxymethyl, difluoromethoxyethyl, and trifluoroethoxymethyl.

The terms "alkoxyl" or "alkoxyalkyl" as used herein refer to an alkyl-O— group wherein alkyl is as previously described. The term "alkoxyl" as used herein can refer to $C_{1-20}$ inclusive, linear, branched, or cyclic, saturated or unsaturated oxo-hydrocarbon chains, including, for example, methoxyl, ethoxyl, propoxyl, isopropoxyl, butoxyl, t-butoxyl, and pentoxyl.

The term "alkyl", either alone or within other terms such as "thioalkyl" and "arylalkyl", as used herein, means a monovalent, saturated hydrocarbon functional group which may be a straight chain (i.e. linear) or a branched chain. An alkyl functional group for use in the present disclosure generally comprises from about 1 to 20 carbon atoms, particularly from about 1 to 10, 1 to 8 or 1 to 7, more particularly about 1 to 6 carbon atoms, or 3 to 6. Illustrative alkyl functional groups include methyl, ethyl, n-propyl, n-butyl, n-pentyl, n-hexyl, isopropyl, isobutyl, isopentyl, amyl, sec-butyl, tert-butyl, tert-pentyl, n-heptyl, n-octyl, n-nonyl, n-decyl, undecyl, n-dodecyl, n-tetradecyl, pentadecyl, n-hexadecyl, heptadecyl, n-octadecyl, nonadecyl, eicosyl, dosyl, n-tetracosyl, and the like, along with branched variations thereof. In certain aspects of the disclosure an alkyl functional group is a $C_1$-$C_6$ lower alkyl comprising or selected from the group consisting of methyl, ethyl, n-propyl, n-butyl, n-pentyl, n-hexyl, isopropyl, isobutyl, isopentyl, amyl, tributyl, sec-butyl, tert-butyl, tert-pentyl, and n-hexyl. An alkyl functional group may be optionally substituted with substituents as defined herein at positions that do not significantly interfere with the preparation of compounds of the disclosure and do not significantly reduce the efficacy of the compounds. In certain aspects of the disclosure, an alkyl functional group is substituted with one to five substituents including halo, lower alkoxy, lower aliphatic, a substituted lower aliphatic, hydroxy, cyano, nitro, thio, amino, keto, aldehyde, ester, amide, substituted amino, carboxyl, sulfonyl, sulfuryl, sulfenyl, sulfate, sulfoxide, substituted carboxyl, halogenated lower alkyl (e.g. $CF_3$), halogenated lower alkoxy, hydroxycarbonyl, lower alkoxycarbonyl, lower alkylcarbonyloxy, lower alkylcarbonylamino, cycloaliphatic, substituted cycloaliphatic, or aryl (e.g., phenylmethyl benzyl)), heteroaryl (e.g., pyridyl), and heterocyclic (e.g., piperidinyl, morpholinyl). Substituents on an alkyl group may themselves be substituted.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

The term "alkylene" as used herein refers to a linear or branched functional group having from about 1 to 10, 1 to 8, 1 to 6, or 2 to 6 carbon atoms and having attachment points for two or more covalent bonds. Examples of such functional groups are methylene, ethylene, propylene, butylene, pentylene, hexylene, ethylidene, methylethylene, and isopropylidene. When an alkenylene functional group is present as a substituent on another functional group it is typically considered to be a single substituent rather than a functional group formed by two substituents.

The term "aralkoxycarbonyl" as used herein refers to an aralkyl-O—CO— group. An exemplary aralkoxycarbonyl group is benzyloxycarbonyl.

The term "aralkyl" as used herein refers to an aryl or a substituted aryl group bonded directly through an alkyl group, such as benzyl. Aralkyl groups include benzyl, phenylethyl, and naphthylmethyl. Other particular examples of substituted aryl functional groups include chlorobenzyl, and amino benzyl.

The term "aralkyloxyl" as used herein refers to an aralkyl-O— group wherein the aralkyl group is as previously described. An exemplary aralkyloxyl group is benzyloxyl.

The term "aroyl" as used herein refers to aryl functional groups, as defined above, attached to a carbonyl functional group as defined herein, including without limitation benzoyl and toluoyl. An aroyl functional group may be optionally substituted with groups as disclosed herein.

The term "aroylamino" as used herein refers to an aroyl-NH— group wherein aroyl is as previously described.

The term "aryl" as used herein refers to an aromatic substituent that can be a single aromatic ring, or multiple aromatic rings that are fused together, linked covalently, or linked to a common group, such as, but not limited to, a methylene or ethylene moiety. The common linking group also can be a carbonyl, as in benzophenone, or oxygen, as in diphenylether, or nitrogen, as in diphenylamine. The term "aryl" specifically encompasses heterocyclic aromatic compounds. The aromatic ring(s) can comprise phenyl, naphthyl, biphenyl, diphenylether, diphenylamine and benzophenone, among others. In particular embodiments, the term "aryl" means a cyclic aromatic comprising about 5 to about 10 carbon atoms, e.g., 5, 6, 7, 8, 9, or 10 carbon atoms, and including 5- and 6-membered hydrocarbon and heterocyclic aromatic rings.

The aryl group can be optionally substituted (a "substituted aryl") with one or more aryl group substituents, which can be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR'R", wherein R' and R" can each be independently hydrogen, alkyl, substituted alkyl, aryl, substituted aryl, and aralkyl.

The term "carbamoyl" as used herein refers to an $H_2N$—CO— group.

The term "carbonyl" as used herein refers to a carbon functional group having two of the four covalent bonds shared with an oxygen atom.

The term "carboxamide" as used herein refers to the group —CONH—.

The term "carboxyl" as used herein refers to the —COOH group.

The term "salt" as used herein refers to compounds that may be formed where acidic protons in the compounds are capable of reacting with inorganic or organic bases. Suitable inorganic salts include those formed with alkali metals, e.g. sodium and potassium, magnesium, calcium, and aluminum. Suitable organic salts include those formed with organic bases such as the amine bases, e.g. ethanolamine, diethanolamine, triethanolamine, tromethamine, N-methylglucamine, and the like. Suitable salts also include acid addition salts formed with inorganic acids (e.g. hydrochloric and hydrobromic acids) and organic acids (e.g. acetic acid, citric acid, maleic acid, and the alkane- and arene-sulfonic acids such as methanesulfonic acid and benzenesulfonic acid). When there are two acidic groups present, a pharmaceutically acceptable salt may be a mono-acid-mono-salt or a di-salt; and similarly where there are more than two acidic groups present, some or all of such groups can be salified.

Compounds of the disclosure which are acidic in nature are capable of forming base salts with various pharmacologically acceptable cations. These salts may be prepared by conventional techniques by treating the corresponding acidic compounds with an aqueous solution containing the desired pharmacologically acceptable cations and then evaporating the resulting solution to dryness, preferably under reduced pressure. Alternatively, they may be prepared by mixing lower alkanolic solutions of the acidic compounds and the desired alkali metal alkoxide together and then evaporating the resulting solution to dryness in the same manner as before. In either case, stoichiometric quantities of reagents are typically employed to ensure completeness of reaction and maximum product yields.

The compounds of the disclosure which are basic in nature can form a wide variety of different salts with various inorganic and organic acids. In practice is it sometimes desirable to first isolate a compound of the disclosure from a reaction mixture as a pharmaceutically unacceptable salt and then convert the latter to the free base compound by treatment with an alkaline reagent and subsequently convert the free base to a pharmaceutically acceptable acid addition salt. The acid addition salts of the base compounds of the disclosure are readily prepared by treating the base compound with a substantially equivalent amount of the chosen mineral or inorganic or organic acid in an aqueous solvent medium or in a suitable organic solvent such as methanol or ethanol. Upon careful evaporation of the solvent, the desired solid salt is obtained.

The compounds of the disclosure may also include "pharmaceutically acceptable salt(s)". By pharmaceutically acceptable salts is meant those salts which are suitable for use in contact with the tissues of a subject or patient without undue toxicity, irritation, allergic response and the like, and are commensurate with a reasonable benefit/risk ratio. Pharmaceutically acceptable salts are described for example, in S. M, Berge, at al., J. Pharmaceutical Sciences, 1977, 66:1. Suitable salts include salts that may be formed where acidic protons in the compounds are capable of reacting with inorganic or organic bases.

A composition of the disclosure may be sterilized by, for example, filtration through bacteria retaining filter, addition of sterilizing agents to the composition, irradiation of the composition, or heating the composition. Alternatively, the compounds or compositions of the present disclosure may be provided as sterile solid preparations e.g. lyophilized powder, which are readily dissolved in sterile solvent immediately prior to use.

A compound of the disclosure of the disclosure may be formulated into a pharmaceutical composition for administration to a subject by appropriate methods known in the art. Pharmaceutical compositions of the present disclosure or fractions thereof comprise suitable pharmaceutically acceptable carriers, excipients, and vehicles selected based on the intended form of administration, and consistent with conventional pharmaceutical practices. Suitable pharmaceutical carriers, excipients, and vehicles are described in the standard text, Remington: The Science and Practice of Pharmacy (21.sup.st Edition. 2005, University of the Sciences in Philadelphia (Editor), Mack Publishing Company), and in The United States Pharmacopeia: The National Formulary (USP 24 NF19) published in 1999. By way of example for oral administration in the form of a capsule or tablet, the active components can be combined with an oral, non-toxic pharmaceutically acceptable inert carrier such as lactose, starch, sucrose, methyl cellulose, magnesium stearate, glucose, calcium sulfate, dicalcium phosphate, mannitol, sorbital, and the like. For oral administration in a liquid form, the chug components may be combined with any oral, non-toxic, pharmaceutically, acceptable inert carrier such as ethanol, glycerol, water, and the like. Suitable binders (e.g., gelatin, starch, corn sweeteners, natural sugars including glucose; natural and synthetic gums, and waxes), lubricants (e.g. sodium oleate, sodium stearate, magnesium stearate, sodium benzoate, sodium acetate, and sodium chloride), disintegrating agents (e.g. starch, methyl cellulose, agar, bentonite, and xanthan gum), flavoring agents, and coloring agents may also be combined in the compositions or components thereof. Compositions as described herein can further comprise wetting or emulsifying agents, or pH buffering agents.

A compound of the disclosure includes derivatives. As used herein the term "derivative" of a compound of the disclosure can refer to a chemically modified compound wherein the chemical modification takes place either at a functional group or ring of the compound. The term "derivative" as used herein can further relate to a substitution of a functional group such as nitro group with another, different, group that is either functional or non-functional with respect to the intended use of the compound, or hydrogen. Non-limiting examples of derivatives of compounds of the disclosure may include N-acetyl, N-methyl, or N-hydroxy groups at any of the available nitrogen atoms in the compound.

A compound of the disclosure can contain one or more asymmetric centers and may give rise to enantiomers, diasteriomers, and other stereoisomeric forms which may be defined in terms of absolute stereochemistry as (R)- or (S)-. Thus, compounds of the disclosure include all possible diasteriomers and enantiomers as well as their racemic and optically pure forms. Optically active (R)- and (S)-isomers may be prepared using chiral synthons or chiral reagents, or resolved using conventional techniques. When a compound of the disclosure contains centers of geometric asymmetry, and unless specified otherwise, it is intended that the compounds include both E and A geometric isomers. All tautomeric forms are also included within the scope of a compound of the disclosure.

A compound of the disclosure includes crystalline forms which may exist as polymorphs. Solvates of the compounds formed with water or common organic solvents are also intended to be encompassed within the term. In addition, hydrate forms of the compounds and their salts are encompassed within this disclosure. Further prodrugs of compounds of the disclosure are encompassed within the term.

The term "solvate" means a physical association of a compound with one or more solvent molecules or a complex of variable stoichiometry formed by a solute (for example, a compound of the disclosure) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological, activity of the solute. Solvates encompass both solution-phase and isolatable solvates. Representative solvates include hydrates, ethanolates, methanolates, and the like. Dehydrate, co-crystals, anhydrous, or amorphous forms of the compounds of the disclosure are also included. The term "hydrate" means a solvate wherein the solvent molecule(s) is/are $H_2O$, including, mono-, di-, and various poly-hydrates thereof. Solvates can be formed using various methods known in the art.

The amount of solvent used to make solvates can be determined by routine testing. For example, a monohydrate of a compound of the disclosure would have about 1 equivalent of solvent ($H_2O$) for each equivalent of a compound of the disclosure. However, more or less solvent may be used depending on the choice of solvate desired.

Compounds of the disclosure may be amorphous or may have different crystalline polymorphs, possibly existing in different salvation or hydration states. By varying the form of a drug, it is possible to vary the physical properties thereof. For example, crystalline polymorphs typically have different solubilities from one another, such that a more thermodynamically stable polymorph is less soluble than a less thermodynamically stable polymorph. Pharmaceutical polymorphs can also differ in properties such as shelf-life, bioavailability, morphology, vapor pressure, density, color, and compressibility.

The term "formulation" as used herein refers to a composition that may be a stock solution of the components, or a composition, preferably including a dilutant such as water or other pharmaceutically acceptable carrier or vehicle that may be available for distribution including to a patient or physician.

The term "halo" as used herein refers to a halogen such as fluorine, chlorine, bromine or iodine atoms.

The term "heteroaryl" as used herein refers to fully unsaturated heteroatom-containing ring-shaped aromatic functional groups having at least one heteroatom selected from carbon, nitrogen, sulfur and oxygen. A heteroaryl functional group may contain one, two or three rings and the rings may be attached in a pendant manner or may be fused. In aspects of the disclosure the term refers to fully unsaturated hetoreatom-containing ring-shaped aromatic functional groups having from 3 to 15, 3 to 10, 3 to 8, 5 to 15, 5 to 10, or 5 to 8 ring members selected from carbon, nitrogen, sulfur and oxygen, wherein at least one ring atom is a heteroatom. Examples of "heteroaryl" functional groups, include without limitation, an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, 4-pyridyl, pyridinyl, pyrimidinyl, pyrazinyl, pyridazinyl, triazolyl, tetrazolyl and the like; an unsaturated condensed heterocyclic group containing 1 to 5 nitrogen atoms, in particular, indolyl, isoindolyl, indolizinyl, benzimidazolyl, quinolyl, isoquinolyl, indazolyl, quinazolinyl, pteridinyl, quinolizidinyl, phthalazinyl, naphthyridinyl, quinoxalinyl, cinnolinyl, phenanthridinyl, acridinyl, phenanthrolinyl, phenazinyl, carbazolyl; purinyl, benzimidazolyl, quinolinyl, isoquinolinyl, beazotriazolyl, tetrazolopyridazinyl and the like; an unsaturated 3 to 6-membered heteromonocyclic group containing an oxygen atom, in particular, 2-furyl, pyranyl, and the like; an unsaturated 5 to 6-membered heteromonocyclic group containing a sulfur atom, in particular, thienyl, 2-thienyl, 3-thienyl, and the like; unsaturated 5 to 6-membered heteromonocyclic group containing 1 to 2 oxygen atoms and 1 to 3 nitrogen atoms, in particular, furazanyl, benzofurazanyl, oxazolyl, isoxazolyl, and oxadiazolyl; an unsaturated condensed heterocyclic group containing 1 to 2 oxygen atoms and 1 to 3 nitrogen atoms, in particular benzoxazolyl, benzoxadiazolyl and the like; an unsaturated 5 to 6-membered heteromonocyclic group containing 1 to 2 sulfur atoms and 1 to 3 nitrogen atoms, for example, thiazolyl, isothiazolyl, thiadiazolyl and the like; an unsaturated condensed heterocyclic group containing 1 to 2 sulfur atoms and 1 to 3 nitrogen atoms such as benzothiazolyl, benzothiadiazolyl and the like. The term also includes functional groups where heterocyclic groups are fused with aryl groups, in particular bicyclic functional groups such as benzofuranyl, benzothiophenyl, phthalazinyl, chromenyl, xanthenyl, and the like. A heteroaryl functional group may be optionally substituted with groups as disclosed herein, for example with an alkyl, amino, halogen, etc., in particular a heteroarylamine. The term may refer to an unsaturated 5 to 6 membered heteromonocyclyl group containing 1 to 4 nitrogen atoms, in particular, pyrrolyl, pyrrolinyl, imidazolyl, pyrazolyl, 2-pyridyl, 3-pyridyl, pyridinyl, pyrimidinyl, pyrazinyl, pyridazinyl, triazolyl, tetrazolyl and the like. A heteroaryl functional group may be optionally substituted with groups disclosed herein, for example with an alkyl, amino, halogen, etc., in particular a substituted heteroaryl functional group is a heteroarylamine.

The term "heterocyclic" as used herein refers to saturated and partially saturated heteroatom containing ring-shaped groups having at least one heteroatom selected from carbon, nitrogen, sulfur and oxygen. A heterocylic group may contain one, two or three rings wherein such rings may be attached in a pendant manner or may be fused. The term may refer to a saturated and partially saturated heteroatom-containing ring-shaped groups having from about 3 to 15, 3 to 10, 5 to 15, 5 to 10, or 3 to 8 ring members selected from carbon, nitrogen, sulfur and oxygen, wherein at least one ring atom is a heteroatom. Exemplary saturated heterocyclic groups include without limitation a saturated 3 to 6-membered heteromonocylic group containing 1 to 4 nitrogen atoms (e.g. pyrrolidinyl, imidazolidinyl, and piperazinyl); a saturated 3 to 6-membered heteromonocyclic group containing 1 to 2 oxygen atoms and 1 to 3 nitrogen atoms (e.g. morpholinyl; sydnonyl); and, a saturated 3 to 6-membered heteromonocyclic group containing 1 to 2 sulfur atoms and 1 to 3 nitrogen atoms (e.g., thiazolidinyl), etc. Examples of partially saturated heterocyclyl groups include without limitation dihydrothiophene, dihydropyranyl, dihydrofuranyl and dihydrothiazolyl. Illustrative heterocyclic groups include without limitation aziridinyl, azetidinyl, 2-pyrrolinyl, 3-pyrrolinyl, pyrrolidinyl, azepinyl, 1,3-dioxolanyl, 2H-pyranyl, 4H-pyranyl, piperidinyl, 1,4-dioxanyl, morpholinyl, pyrazolinyl, thiomorpholinyl, 1,2,3,6-tetrahydropyridinyl, oxiranyl, oxetanyl, tetrahydrofuranyl, tetrahydropyranyl, tetrahydropyridinyl, tetrahydrothiopyranyl, thioxanyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, quinuelidinyl, quinolizinyl, and the like.

The term "hydroxyalkyl" as used herein refers to an alkyl group substituted with an —OH group.

The term "hydroxyl" as used herein refers to the —OH group.

The term "lower-alkyl-substituted-amino" as used herein refers to any alkyl unit containing up to and including eight carbon atoms where one of the aliphatic hydrogen atoms is replaced by an amino group. Examples of such include, but are not limited to, ethylamino and the like.

The terms "carrier" and "vehicle" as used interchangeably herein refers to a medium which does not interfere with the effectiveness or activity of an active ingredient. A carrier or vehicle may include diluents, wetting or emulsifying agents, pH buffering agents, and miscellaneous materials such as absorbents that may be needed in order to prepare a particular composition. Examples of carriers etc. include but are not limited to saline, buffered saline, dextrose, water, glycerol, ethanol, and combinations thereof. The use of such media and agents for an active substance is well known in the art.

The term "substituted alkenyl" as used herein includes an alkenyl group substituted by, for example, one to three substituents, preferably one to two substituents, such as alkyl, alkoxy, haloalkoxy, alkylalkoxy, haloalkoxyalkyl, alkanoyl, alkanoyloxy, cycloalkyl, cycloalkoxy, acyl, acylamino, acyloxy, amino, alkylamino, alkanoylamino, aminoacyl, aminoacyloxy, cyano, halogen, hydroxyl, carboxyl, carboxylalkyl, carbamyl, keto, thioketo, thiol, alkylthio, sulfonyl, sulfonamido, thioalkoxy, aryl, nitro, and the like.

The term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. In some embodiments of the disclosure the functional group is a terminal substitution.

The term "substituted aryl" includes aryl groups, as defined herein, in which one or more atoms or functional groups of the aryl group are replaced with another atom or functional group including, for example, alkyl, substituted alkyl, halogen, aryl, substituted aryl, alkoxyl, hydroxyl, nitro, amino, alkylamino, dialkylamino, sulfate, and mercapto.

The term "substituted cycloaliphatic" as used herein refers to a cycloalkane possessing less than 8 carbons or a fused ring system consisting of no more than three fused rings, and where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such groups include, but are not limited to, 1-chlorodecalyl and the like.

The term "substituted aliphatic" as used herein refers to an alkyl or an alkane possessing less than 10 carbons. The term "substituted aliphatic" refers to an alkyl or an alkane possessing less than 10 carbons where at least one of the aliphatic hydrogen atoms has been replaced by a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such groups include, but are not limited to, 1-chloroethyl and the like. In some embodiments of the disclosure the functional group is a terminal substitution.

The term "thio" as used herein refers to a compound described previously herein wherein a carbon or oxygen atom is replaced by a sulfur atom.

The term "thiol" as used herein means —SH. A thiol may be substituted with a substituent disclosed herein, in particular alkyl (thioalkyl), aryl (thioaryl), alkoxy (thioalkoxy) or carboxyl.

The term "thioalkoxy" as used herein, alone or in combination, refers to a chemical functional group where a sulfur atom (S) is bonded to an alkoxy group with the general chemical formula —SR$_{24}$ where R$_{24}$ is an alkoxy group which may be substituted. A "thioalkoxy group" may have 1-6 carbon atoms i.e. a —S—(O)—C$_1$-C$_6$ alkyl group wherein C$_1$-C$_6$ alkyl have the meaning as defined above. Illustrative examples of a straight or branched thioalkoxy group having from 1 to 6 carbon atoms, also known as a C$_1$-C$_6$ thioalkoxy, include thiomethoxy and thioethoxy.

The term "thioalkyl" as used herein, alone or in combination, refers to a chemical functional group where a sulfur atom (S) is bonded to an alkyl, which may be substituted. Examples of thioalkyl groups are thiomethyl, thioethyl, and thiopropyl. A thioalkyl may be substituted with a substituted or unsubstituted carboxyl, aryl, heterocyclic, carbonyl, or heterocyclic.

The term "thioaryl" as used herein, alone or in combination, refers to a chemical functional group where a sulfur atom (S) is bonded to an aryl group with the general chemical formula —SR, wherein R is aryl that may be substituted. Illustrative examples of thioaryl groups and substituted thioaryl groups are thiophenyl, chlorothiophenol, para-chlorothiophenol, thiobenzyl, 4-methoxy-thiophenyl, 4-nitro-thiophenyl, and para-nitrothiobenzyl.

A thiol may be substituted with a substituted or unsubstituted heteroaryl or heterocyclic, in particular a substituted or unsubstituted saturated 3 to 6-membered heteromonocylic group containing 1 to 4 nitrogen atoms (e.g. pyrrolidinyl, imidazolidinyl, piperidinyl, and piperazinyl) or a saturated 3 to 6-membered heteromonocyclic group containing 1 to 2 oxygen atoms and 1 to 3 nitrogen atoms (e.g. morpholinyl; sydrionyl), especially a substituted morpholinyl or piperidinyl.

The term "serotonin receptor" (also known as 5-hydroxytryptamine receptors or 5-HT receptors) as used herein refers to a group of G protein-coupled receptors (GPCRs) and ligand-gated ion channels (LGICs) found in the central and peripheral nervous systems. They mediate both excitatory and inhibitory neurotransmission. The serotonin receptors are activated by the neurotransmitter serotonin, which acts as their natural ligand. The serotonin receptors modulate the release of many neurotransmitters, including glutamate, GABA, dopamine, epinephrine/norepinephrine, and acetylcholine, as well as many hormones, including oxytocin, prolactin, vasopressin, cortisol, corticotropin, and substance P, among others. The serotonin receptors influence various biological and neurological processes such as aggression, anxiety, appetite, cognition, learning, memory, mood, nausea, sleep, and thermoregulation. The serotonin receptors are the target of a variety of pharmaceutical drugs, including many antidepressants, antipsychotics, anorectics, antiemetics, gastroprokinetic agents, antimigraine agents, hallucinogens, and entactogens.

Very non-selective agonists of 5-HT receptor subtypes include ergotamine (an antimigraine), which activates 5-HT1A, 5-HT1D, 5-HT1B, D2 and norepinephrine receptors. LSD (a psychedelic) is a 5-HT1A, 5-HT2A, 5-HT2C, 5-HT5A, 5-HT5, 5-HT6 agonist.

Numerical ranges recited herein by endpoints include all numbers and fractions subsumed within that range (e.g., 1 to 5 includes 1, 1 5, 2, 2.75, 3, 3.90, 4, and 5). It is also to be understood that all numbers and fractions thereof are presumed to be modified by the term "about." The term "about" means plus or minus 0.1 to 50%, 5-50%, or 10-40%, preferably 10-20%, more preferably 10% or 15%, of the number to which reference is being made. Further, it is to be understood that "a", "an," and "the" include plural referents unless the content clearly dictates otherwise. Thus, for example, reference to a composition comprising "a compound" includes a mixture of two or more compounds.

Description

The present disclosure encompasses embodiments of derivatives of 1,2,3,4-tetrahydroisoquinoline (THIQ) having the general formula of A-(CH$_2$)$_n$—B, wherein A is THIQ or a substituted derivative thereof and B is an aryl, cycloalkylaryl, or cycloalkyl group, wherein A and B are linked to each other by an alkyl or substituted alkyl chain. The compounds of the disclosure are advantageous as selective ligands (as either agonists or antagonists) of receptors of the central nervous system, and in particular of the seratonin receptors. The compounds of the disclosure, or salts thereof, may be formulated into pharmaceutical compositions for the delivery of therapeutic amounts of the ligand or ligands to a patient in need thereof by any route of administration suitable for the desired treatment protocol and especially for the treatment of psychiatric disorders.

It is now well established that targeting a single receptor is often inadequate in treating several diseases including diseases originating from the central nervous system. Thus, drugs such asaripiprazole, lurasidone and others derive their superior therapeutic outcomes from their ability to target multiple receptors in the CNS (DeLeon et al., (2004) *Clin. Ther.* 26: 649; Davies et al., (2004) CNS Drug Rev. 10: 317; Shapiro et al., (2003) *Neuropsychopharmacol.* 28: 1400; Franklin et al., (2015) *Neuropsychiatr. Dis. Treat.* 11: 2143). The neurotransmitters, dopamine (DA) and serotonin (5-HT), are of particular interest because of their involvement in several neurological and psychiatric diseases such as schizophrenia, major depressive disorder (MDD), depression, attention deficit and hyperactivity disorder (ADHD), and addiction (Meltzer, H. Y. (1999) *Neuropsychopharmacol.* 21: 106S; Meltzer et al., (2003) *Prog. Neuropsychopharmacol. Biol. Psychiatry* 27: 1159; Volkow et al., (2004) *Mol. Psychiatry* 9: 557; Muller & Homberg (2015) *Behav. Brain Res.* 277: 146). Recent research has indicated that the serotonin receptors (5-HTRs) in particular play significant roles in CNS physiological activities, and dysregulation of these receptors often results in several diseases. For example, the serotonin 1A receptor (5-HT1AR) which is found predominantly in the dorsal raphe nuclei, hippocampus, and cortico-limbic regions, controls memory, cognition, and mood, functions that are impaired in anxiety, depression and schizophrenia (Glennon et al., (1995) *Psychopharmacology: The Fourth Generation of Progress*, Bloom & Kupfer, Eds.; Raven Press: New York). Several lines of evidence now support the anti-negative symptoms and cognitive enhancement effects of ligands that activate 5-HT1AR in schizophrenia (Meltzer et al., (2003) *Prog. Neuropsychopharmacol. Biol. Psychiatry* 27: 1159; Newman-Tancredi & Kleven (2011) *Psychopharmacology* (*Berl.*) 216: 451). Similarly, the serotonin7 receptor (5-HT7R), the most recent addition to the 5-HTreceptor subtypes (Ruat et al., (1993) *Proc. Natl. Acad. Sci. U.S.A.* 90:8547; Lovenberg et al., (1993) *Neuron* 11: 449; Bard et al., (1993) *J. Biol. Chem.* 268: 23422), has been shown to mediate key functions such as sleep, mood, learning, memory, and cognition (Leopoldo et al., (2011) *Pharmacol. Ther.* 129: 120; Hedlund & Sutcliffe (2004) *Trends Pharmacol. Sci.* 25: 481; Matthys et al., (2011) *Mol. Neurobiol.* 43: 228; Gasbarri et al., (2008) *Behav. Brain Res.* 195: 164). Interestingly, the 5-HT7R forms heterodimers with the 5-HT1AR in mostbrain regions, producing a cross-talk that has been implicated in depression and other CNS disorders. Both receptors share over 40% sequence similarity that may account for the cross reactivity seen among ligands that interact at both receptors (Naumenko et al., (2014) *CNS Neurosci. Ther.* 20: 582; Hoyer et al., (2002) *Pharmacol. Biochem. Behav.* 71: 533; Renner et al., (2012) *J. Cell Sci.* 125: 2486). Accordingly, agents with dual binding affinities to both receptors may be beneficial as treatment options for depression and other cognitive impairment disorders.

In general, the compounds evaluated were obtained by refluxing or carrying out a microwave-assisted reaction of THIQ with various alkylating agents in dimethoxyethane (DME) or acetonitrile ($CH_3CN$) in the presence of $K_2CO_3$ as a base and a catalytic amount of KI. The target compounds 1-3 (FIGS. 1 and 7), were prepared by first N-alkylating potassium phthalimide with 1,4-dibromobutane to produce alkyl bromide 1b (FIG. 1) that was separately reacted with THIQ, decahydroisoquinoline, and isoindoline to afford compounds 1, 2 and 3 (FIGS. 1 and 7), respectively.

Figure 2:
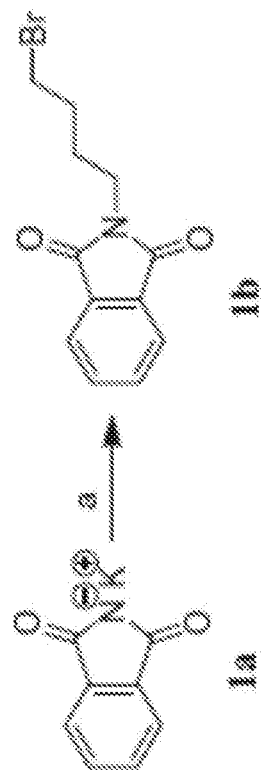
FIG. 2 illustrates scheme 2: Synthesis of 3-substituted-1H-indole analog. Reagents and condition: (a) $LiAlH_4$ in dry THF, rt, 12 h; (b) $I_2$/$PPh_3$, imidazole; (c) THIQ, $K_2CO_3$/KI, DME, reflux, 12 h.
Figure 2:
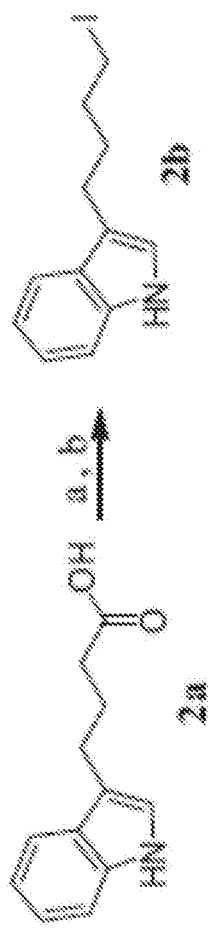

A three-step reaction procedure was used to synthesize compound 4 (Scheme 2 (FIG. 2)). Commercially available 4-(1H-indol-3-yl)butanoic acid, 2a (FIG. 2) was reduced using LAH in dry THF to produce the corresponding alcohol that was subsequently converted to the iodo intermediate 2b (FIG. 2) via an Appel reaction (Smith & Takacs (2010) *Am. Chem. Soc.* 132: 1740; Appel, R. (1975) *Angew. Chem., Int. Ed. Engl.* 14: 801). The obtained alkylating agent was then coupled to THIQ to afford 4 (FIG. 2). Deoxygenation of the previously reported indanone 3a (FIG. 3) (Peprah et al., (2012) *Bioorg. Med. Chem.* 20: 1671) under Clemmenson reduction conditions yielded 3b (FIG. 3) which was then used to alkylate THIQ and afforded compound 5 (FIG. 3) as shown in Scheme 3, FIG. 3.

The chloride 4a (FIG. 4), mesylate 4b (FIG. 4), and tosylate 4c (FIG. 4) salts were synthesized by literature procedures and subsequently used to alkylate THIQ to yield compounds 6 (FIG. 4), 7 (FIG. 4), and 8 (FIG. 4), respectively using the general alkylating conditions described in Scheme 1 (FIG. 1). Sulfoxide 9 (FIG. 5) was prepared by oxidation of 8 (FIG. 5) using the previously reported meta-peroxybenzoic acid (m-CPBA) mediated oxidative conditions depicted in Scheme 5, (FIG. 4) (Peprah et al., (2012) *Bioorg. Med. Chem.* 20: 1671).

Figure 6:
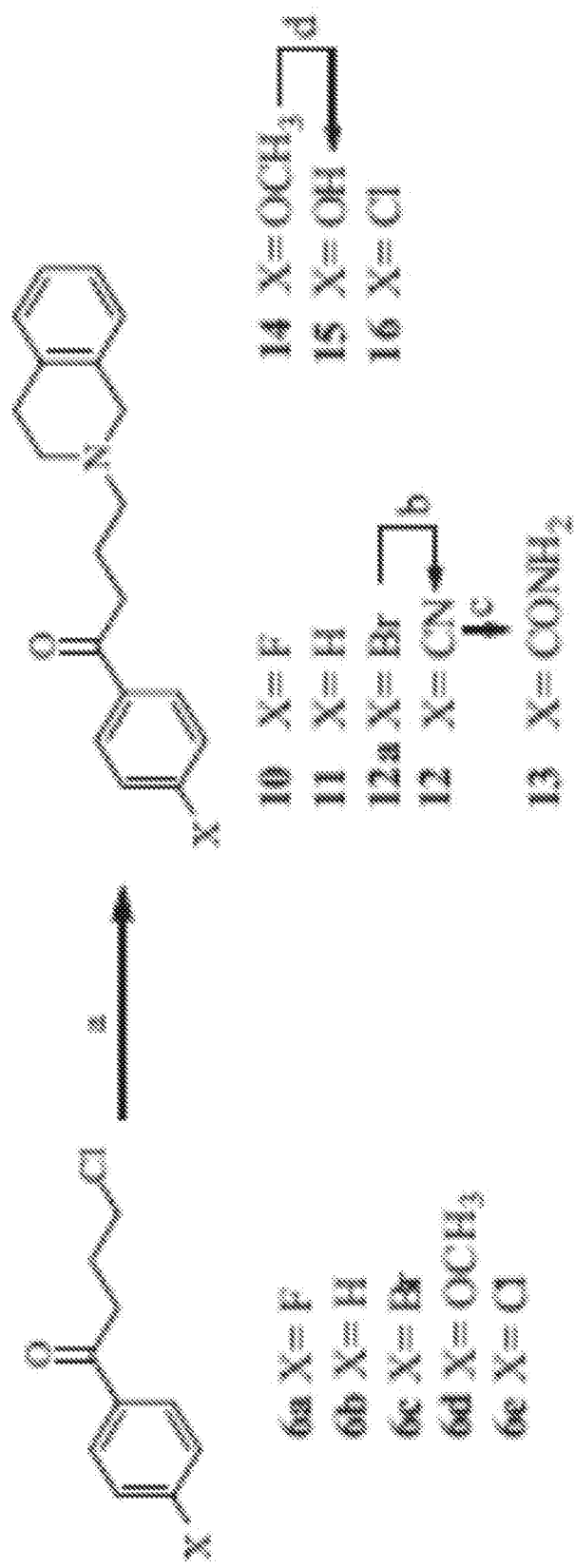
FIG. 6 illustrates scheme 6: Synthesis of 4-substituted-butyrophenone analogs. Reagents and conditions: (a) THIQ, $K_2CO_3$/KI, DME, 120° C., MW; (b) $K_4[Fe(CN)_6]\cdot 3H_2O$, $Pd(OAc)_2$, KI, $Na_2CO_3$, $N_2$, DMA, 120° C., 12 h; (c) KOH, t-butyl alcohol, reflux, 12 h; (d) aq HBr 48%, NaI, 110° C., MW.

Alkylating agents 6a (FIG. 6), 6b (FIG. 6), and 6e (FIG. 6) were obtained commercially and were used to synthesize compounds 10 (FIG. 6), 11 (FIG. 6), and 16 (FIG. 6) respectively whereas 6c (FIG. 6) and 6d (FIG. 6) were prepared following Friedel-Crafts acylation reaction as reported (Chowdhury et al., (2012) *Photochem. Photobiol. B* 115: 25) and subsequently used to obtain compounds 12a (FIG. 6) and 14 (FIG. 6), respectively by scheme 6 (FIG. 6). Finally, using potassium ferrocyanide ($K_4[Fe(CN)_6]$-$3H_2O$) as the cyanide source, palladium-catalyzed cyanation (Weissman et al., (2005) *Org. Chem.* 70: 1508) of 12a (FIG. 6) afforded compound 12 (FIG. 6). Base-catalyzed hydrolysis of the cyano group (Hall & Gisler (1976) *Org. Chem.* 41: 3769) in 12 (FIG. 6) afforded the corresponding amide 13 (FIG. 6). Demethylation of 14 with hydrobromic acid afforded compound 15 (FIG. 6).

The THIQ moiety has been the subject of several recent publications (Silvano et al., (2010) *Mol. Pharmacol.* 78: 925; Liu et al., (2014) *ACS Med. Chem. Lett.* 5: 760; Wasik et al., (2014) *Neurotox. Res.* 26: 240; Canale et al., (2014) *Eur. J. Med. Chem.* 78: 10; Mozdzen et al., (2014) *Eur. J. Pharmacol.* 729: 107; Zajdel et al., (2011) *Bioorg. Med. Chem.* 19: 6750; Vermeulen et al., (2004) *J. Med. Chem.* 47: 5451). In a campaign to synthesize new drugs with selective affinity for the 5-HT7 receptor, 2-(4-(3,4-dihydroisoquinolin-2(1H)-yl)butyl)isoindoline-1,3-dione (1, (FIG. 7)) was synthesized and evaluated its affinity for key 5-HTR subtypes, including the 5-HT7R. As shown in Table 1, compound 1 (FIG. 7) demonstrated a low nanomolar potency at the 5-HT7R and little affinity to the other key 5-HTR subtypes including 5-HT1AR where it is over 50-fold less potent.

TABLE 1

Binding affinity of analogs at selected serotonin receptors

| Compound** | $K_i$ nM ($pK_i$) | | | | |
|---|---|---|---|---|---|
| | 5-HT$_{1A}$ | 5-HT$_{2A}$ | 5-HT$_7$ | 5-HT$_{2B}$ | 5-HT$_{2C}$ |
| 1 | 499 | MTA | 8.6 | MTA | MTA |
| | (6.3 ± 0.05) | | (8.07 ± 0.05) | | |
| 2 | 533 | >10,000 | 330 | 400 | 37 |
| | (6.27 ± 0.07) | | (6.48 ± 0.07) | (6.4 ± 0.08) | (7.43 ± 0.07) |
| 3 | MTA | MTA | MTA | MTA | 151 |
| | | | | | (6.82 ± 0.07) |
| 4 | 1689 | 926 | 52 | MTA | MTA |
| | (5.77 ± 0.06) | (6.03 ± 0.08) | (7.29 ± 0.07) | | |
| 5 | 193 | 522.5 | 86.0 | 1247 | MTA |
| | (6.72 ± 0.04) | | | (5.9 ± 0.09) | |
| 6 | 141 | 726 ±117 | 27 | 1713 | 4440 |
| | (6.85 ± 0.06) | | (7.57 ± 0.08) | (5.77 ± 0.08) | (5.4 ± 0.1) |
| 7 | 244 | 322 ± 61.9 | 100 | 561 | MTA |
| | (6.61 ± 0.05) | | (7.00 ± 0.06) | (6.25 ± 0.09) | |
| 8 | 217 | 317 | 49 | 204 | 2623 |
| | (6.66 ± 0.06) | (6.43 ± 0.07) | (7.31 ± 0.05) | (6.69 ± 0.07) | (5.58 ± 0.09) |
| 9 | 41 | 1779 | 22.5 | 1166 | MTA |
| | (7.39 ± 0.05) | (5.75 ± 0.09) | (7.64 ± 0.07) | (5.93 ± 0.08) | |
| 10* | 12 ± 1.0 | 14 ± 1.0 | 364 ± 12 | 614 ± 36 > 10,000 | 710 |
| | | | | | (6.15 ± 0.08) |
| 11 | 3.9 | 358 | 273 | 603 | 295 |
| | (8.41 ± 0.05) | (6.45 ± 0.05) | (6.56 ± 0.06) | (6.22 ± 0.05) | (6.53 ± 0.06) |
| 12 | 23 | 755 | 152 | 443 | 38 |
| | (7.64 ± 0.05) | (6.12 ± 0.06) | (6.82 ± 0.08) | (6.12 ± 0.06) | (7.42 ± 0.07) |
| 13 | 404 | 12 | 587 | 1892 | 23 |
| | (6.39 ± 0.04) | (7.91 ± 0.08) | (6.23 ± 0.07) | (5.72 ± 0.05) | (7.54 ± 0.07) |
| 14 | 2993 | 17 | 723 | 1404 | 33.50 |
| | (5.67 ± 0.05) | (7.77 ± 0.08) | (6.14 ± 0.05) | (5.85 ± 0.07) | (7.46 ± 0.07) |
| 15 | 851 | 10 | 358 | MTA | 8.2 |
| | (6.14 ± 0.05) | (7.99 ± 0.08) | (6.45 ± 0.05) | | (8.09 ± 0.07) |
| 16 | MTA | 3.6 | 232 | 2976 | Aripiprazole** |
| | | (8.45 ± 0.07) | (6.63 ± 0.07) | (5.53 ± 0.06) | |
| Aripiprazole | 5.6 ± 0.8 | 8.7 ± 2.0 | 10.3 ± 3.7 | 0.36 ± 0.11 | 76 ± 8.0 |

Figure 7:
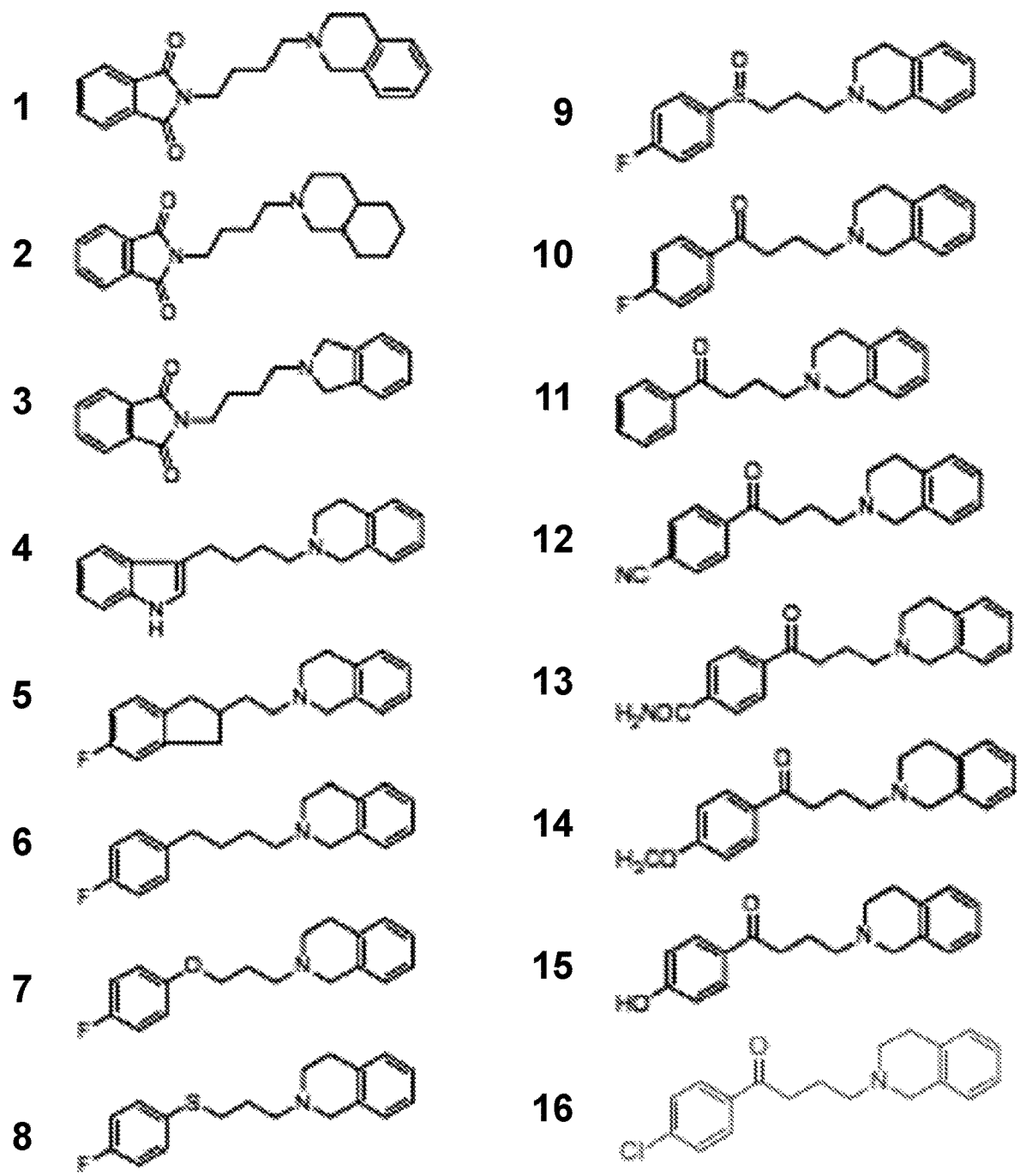
FIG. 7 illustrates seretonin receptor ligand analogs 1-15.
Figure 8:
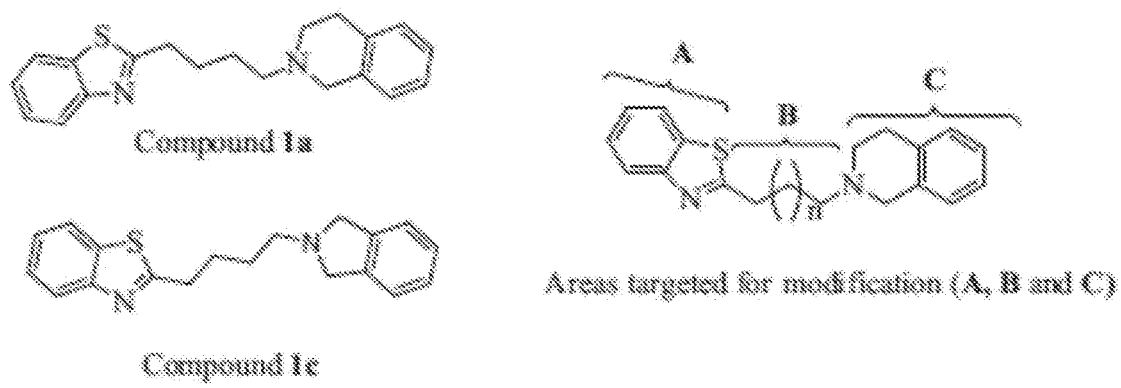
FIG. 8 illustrates structures of the benzothiazole compounds depicting the various segments of modification.

**Structures as shown in FIG. 7

Replacement of the THIQ ring in 1 with decahydroisoquinoline to yield 2 (FIG. 7) resulted in about a 40-fold decrease in binding affinity to the 5-HT7R, with binding affinity at 5-HT1AR and 5-HT2AR remaining essentially unchanged. Compound 2 (FIG. 7), however, displays selectivity towards the 5-HT2CR (Ki=37 nM). Further modification of 1 (FIG. 7) by replacing the tetrahydroisoquinoline ring with isoindoline ring to obtain 3 (FIG. 7) resulted in significant loss of activity at all receptor subtypes except the 5-HT2CR where there was moderate affinity (Ki=151 nM).

Based on the results of the binding affinities for compounds 1-3 (FIG. 7), it is clear that the THIQ ring serves as an important pharmacophore for binding affinity to the 5-HT7R in these compounds. This observation informed the next design strategy to keep the THIQ group and to focus on modifications elsewhere in the molecule, including that of the isoindoline-1,3-dione moiety. Replacement of the isoindoline-1,3-dione moiety in 3 (FIG. 7) with indole to obtain 4 (FIG. 7) restored nanomolar binding affinity to the 5-HT7R, while replacement with 5-fluoro-2,3-dihydro-1H-indene to form 5 (FIG. 7) led to significant binding affinity to both 5-HT1AR and 5-HT7R (Ki=193 and 86 nM, respectively).

Excision of a methylene group from the indene moiety in compound 5 (FIG. 7) led to ring-opened 6 (FIG. 7) with improved affinity for both 5-HT1AR and 5-HT7R. Replacement of the benzylic methylene group in 6 (FIG. 7), with oxygen (7 (FIG. 7)), and sulfur (8 (FIG. 7)) did not result in significant changes. However, oxidation of the sulfide to obtain the sulfoxide 9 (FIG. 7), increased affinity for both 5-HT1AR (Ki=41 nM) and 5-HT7R (Ki=22.5 nM).

Next, the sulfoxide group in 9 (FIG. 7) was replaced by a carbonyl to form 4-(3,4-dihydroisoquinolin-2(1H)-yl)-1-(4-fluorophenyl)butan-1-one (10 (FIG. 7)) which resulted in a 3-fold increase in binding affinity at the HT1AR (Ki=12 nM) but a decrease of 16-fold at the 5-HT7R (Ki=364 nM). Affinity at the 5-HT2AR was found to have improved drastically to 14 nM. Similar low nanomolar binding affinities are observed for compounds 11 (FIG. 7) (the defluorinated analog) and 12 (FIG. 7) (replacement of the fluoro with the electron withdrawing and hydrophilic cyano substituent) at the 5-HT2AR while significant loss of affinities are noted at the 5-HT1AR and 5-HT7R. However, changing the p-cyano substituent in 12 (FIG. 7) to the carboxamide 13 (FIG. 7), the methoxy group 14 (FIG. 7), or its hydroxy analog 15 (FIG. 7), produced the desired dual 5-HT1AR and 5-HT7R binding affinity ligands with low nanomolar affinity constants. Thus, it would appear that various substituents covering at least three quadrants of the Craig plot did not yield a clearly defined structure affinity relationship trend. Finally, compound 16 (FIG. 7) was evaluated, with the p-fluoro atom of compound 10 (FIG. 7) replaced by a chloro atom which yielded the most potent dual 5-HT1AR (Ki=8.2 nM) and 5-HT7R (Ki=3.6 nM) binding affinity ligand in the series.

Comparing compound 16 (FIG. 7) and aripiprazole (7-{4-[4-(2,3-dichlorophenyl)piperazin-1-yl]butoxy}-3,4-dihydroquinolin-2(1H)-one), both have high affinities at 5-HT1AR (5.6 vs 8.2 nM), and 5-HT7R (3.6 vs 10.3 nM), but differ significantly at the other serotonin receptors evaluated, with compound 16 (FIG. 7) having little or no binding at 5-HT2AR and 5-HT2CR (Ki=2976 nM) and moderate binding at 5-HT2BR (Ki=232 nM), while aripiprazole has high affinity for 5-HT2AR (Ki=8.7 nM) and 5-HT2BR (Ki=0.36 nM) and moderate affinity to 5-HT2CR (Ki=76 nM).

The target compounds were also screened at additional CNS receptors with clinical significance including the D2R, D3R, D4R, H1R, and SERT and the results reported in Table 2.

TABLE 2

Binding affinities of analogs at dopamine subtype receptors, histamine H1 receptor, and SERT

| Compound | $K_i$ nM ($pK_i$) | | | | |
|---|---|---|---|---|---|
| | D2 | D3 | D4 | H1 | SERT |
| 1** | MTA | 491 (6.3 ± 0.10) | 240 (6.62 ± 0.08) | MTA | MTA |
| 2 | >10,000 | 630 (6.2 ± 010) | >10,000 (<5.0) | 3632 (5.44 ± 0.06) | >10,000 (<5.0) |
| 3 | MTA | MTA | 1,361 (5.87 ± 0.09) | MTA | MTA |
| 4 | 170 (6.8 ± 0.10) | 469 (6.33 ± 0.09) | 35 (7.46 ± 0.06) | 836 (6.08 ± 0.08) | 113.0 |
| 5* | 1150 | 162 | 123 | NA | 163.0 |
| 6 | 319 (6.5 ± 0.07) | 6007 ± 1491 NA | 160 (6.8 ± 0.05) | 738 (6.13 ± 0.06) | 4284 |
| 7 | 166 (6.78 ± 0.05) | 769 ± 161 NA | 83 (7.08 ± 0.05) | 382 (6.42 ± 0.08) | MTA |
| 8 | 123 (6.91 ± 0.04) | 118 (6.93 ± 0.04) | 146 (6.84 ± 0.06) | NA | MTA |
| 9 | 422 (6.37 ± 0.08) | 161 (6.79 ± 0.04) | 460 (6.39 ± 0.06) | NA | MTA |
| 10* | 49 ± 3 | 72 ± 5 | 2.3 ± 0.2 | 86.3 ± 7.26 | MTA |
| 11 | 646 (6.19 ± 0.06) | 161 (6.79 ± 0.04) | MTA | 68 (7.2 ± 0.20) | 1534 |
| 12 | 1456 (5.84 ± 0.09) | 336 (6.47 ± 0.04) | 345 (6.46 ± 0.04) | 177 (6.8 ± 0.10) | 895 |
| 13 | 218 (6.66 ± 0.05) | 18 (7.75 ± 0.06) | 205 (6.69 ± 0.04) | 1427 (5.8 ± 0.10) | MTA |
| 14 | 249 (6.6 ± 0.07) | 38 (7.42 ± 0.05) | 210 (6.68 ± 0.05) | 216 (6.7 ± 0.10) | 2442 |
| 15 | 366 (6.44 ± 0.08) | 143 (6.84 ± 0.05) | 773 (6.11 ± 0.04) | MTA | MTA |
| 16 | 126 (6.9 ± 0.06) | 17 (7.77 ± 0.04) | 86 8.09 ± 0.07 | 597 (6.22 ± 0.05) | MTA |
| Aripiprazole | 3.3 ± 1.1 | 9.7 ± 5.4 | 510 ± 93 | 25.1 ± 2.6 | 1080 ± 180 |

**Structures as shown in FIG. 7
MTA = Missed 50% of threshold inhibition.
*Only Ki values reported. NA = Not available. Ki values without the associated SEM, are within 20% of the mean value.

Compounds 1-3 (FIG. 7) showed little if any affinities at the aforementioned receptors/transporter. Compound 4 (FIG. 7), the indolealkyl substituted analog of 1, produced moderate affinities for D2R, D4R and SERT while the dihydroindene analog 5 (FIG. 7) had moderate affinities for D3R, D4R and SERT. Opening the dihydroindene ring in 5 (FIG. 7) with excision of a methylene group (6 (FIG. 7)), or replacing the benzylic carbon with oxygen, sulfur, or sulfoxide (7-9 (FIG. 7)) resulted in significant loss of affinity for SERT with no clear SAR features at the other receptors in Table 2.

Replacement of the sulfoxide with a carbonyl (10 (FIG. 7)) produced significant increase in binding at the dopamine receptors, suggesting that perhaps the butyrophenone THIQ scaffold could constitute a useful hit for further development as ligands for multiple receptor targeting. However, probing the electron donating or withdrawing nature and/or the hydrophilic/hydrophobic nature of substituents at the para position of the phenyl ring (10-16 (FIG. 7)) according to the Craig plot procedure did not produce an increase in potency at the dopamine receptors and did not reveal any notable SAR trend. Regarding their histamine binding affinities, only 10 (FIG. 7) and 11 (FIG. 7) have affinity constants below 100 nM suggesting that these compounds may have low propensity for interacting at the histamine H1 receptor and hence less sedative effect. Of the sixteen compounds reported, three, compounds 13 (FIG. 7), 14 (FIG. 7), and 16 (FIG. 7) (13: Ki=13 nM, 14: Ki=38 nM, 16: Ki=17 nM respectively) showed significant binding affinities to the D3R.

Given their concentration in limbic and cortical regions of the brain, D3Rs have been hypothesized to be potential targets for the design of new antipsychotics with limited extrapyramidal side effects. However, there have been reports that selective D3R blockade only resulted in marginal antipsychotic effects. This has led to the demonstration that dual D2/D3 receptor blockade produces effective antipsychotic actions (Depoortere et al., (2007) *Br. J. Pharmacol.* 151: 253; Butini et al., (2009) *J. Med. Chem.* 52: 151; Dutta et al., (2004) *Bioorg Med. Chem.* 12: 4361). The moderate binding affinities of these compounds for the D2 receptors (13 (FIG. 7): Ki=218 nM; 14 (FIG. 7): Ki=249 nM; and 16 (FIG. 7) Ki=126 nM), combined with their serotonin binding profiles make them potential drug leads. In particular, the preferential and more potent binding of 16 (FIG. 7) at D3R (Ki=17 nM) compared to D2R (7-fold) suggests evaluation for intrinsic activities and subsequent exploitation in the treatment of CNS conditions including the negative and cognitive symptoms of schizophrenia and bipolar mania (Agai-Csongor et al., (2012) *Bioorg. Med. Chem. Lett.* 22: 3437; Neill et al., (2016) *N. Eur. Neuropsychopharmacol.* 26, 3; Adham et al., (214) *N. Eur. Neuropsychopharmacol.* 24: S233). Interestingly, the D3R binding of compound 16 (FIG. 7) is similar to that of aripiprazole (Ki=17 vs 9.7 nM), while the D2R binding affinity is similar to that of clozapine[41] (Ki=126 nM vs pKi=6.87 or Ki=130 nM). Strong binding to the D3R may also be associated with procognitive effects, as reported.[42]

Thus, using compound 1 (FIG. 7) which showed significant selectivity (>50 fold) for 5-HT7 receptor compared to the 5-HT1AR as the starting hit, and guided by results from the SAR studies, it was possible to obtain very potent dual 5-HT1A and 5-HT7 receptor affinity ligands. In addition, compound 16 (FIG. 7) showed moderate binding affinity at D2R, high affinity at D3R, and a 7-fold selectivity for D3R over D2R, which portends treating the negative and cognitive symptoms of schizophrenia, as well as bipolar mania.

Figure 9:
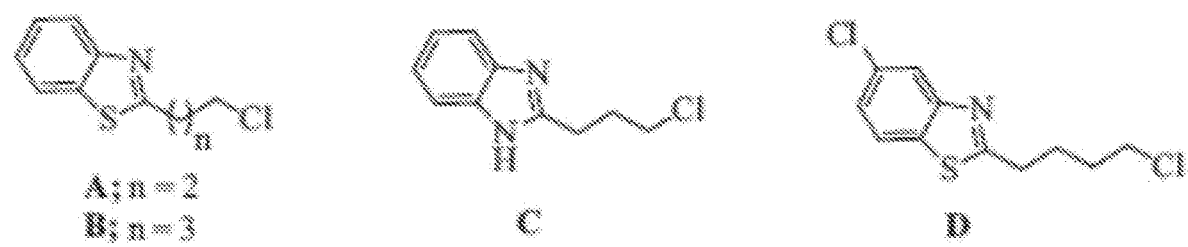
FIG. 9 illustrates alkylating agents used in the syntheses of compounds in group 1 (1a-1i).
Figure 10:
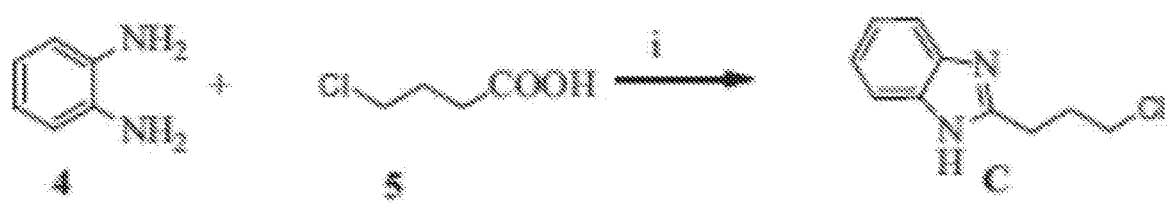
FIG. 10 illustrates scheme 7: Synthesis of alkylating agent C. Reagents and conditions: 5N HCl, reflux.
Figure 11:
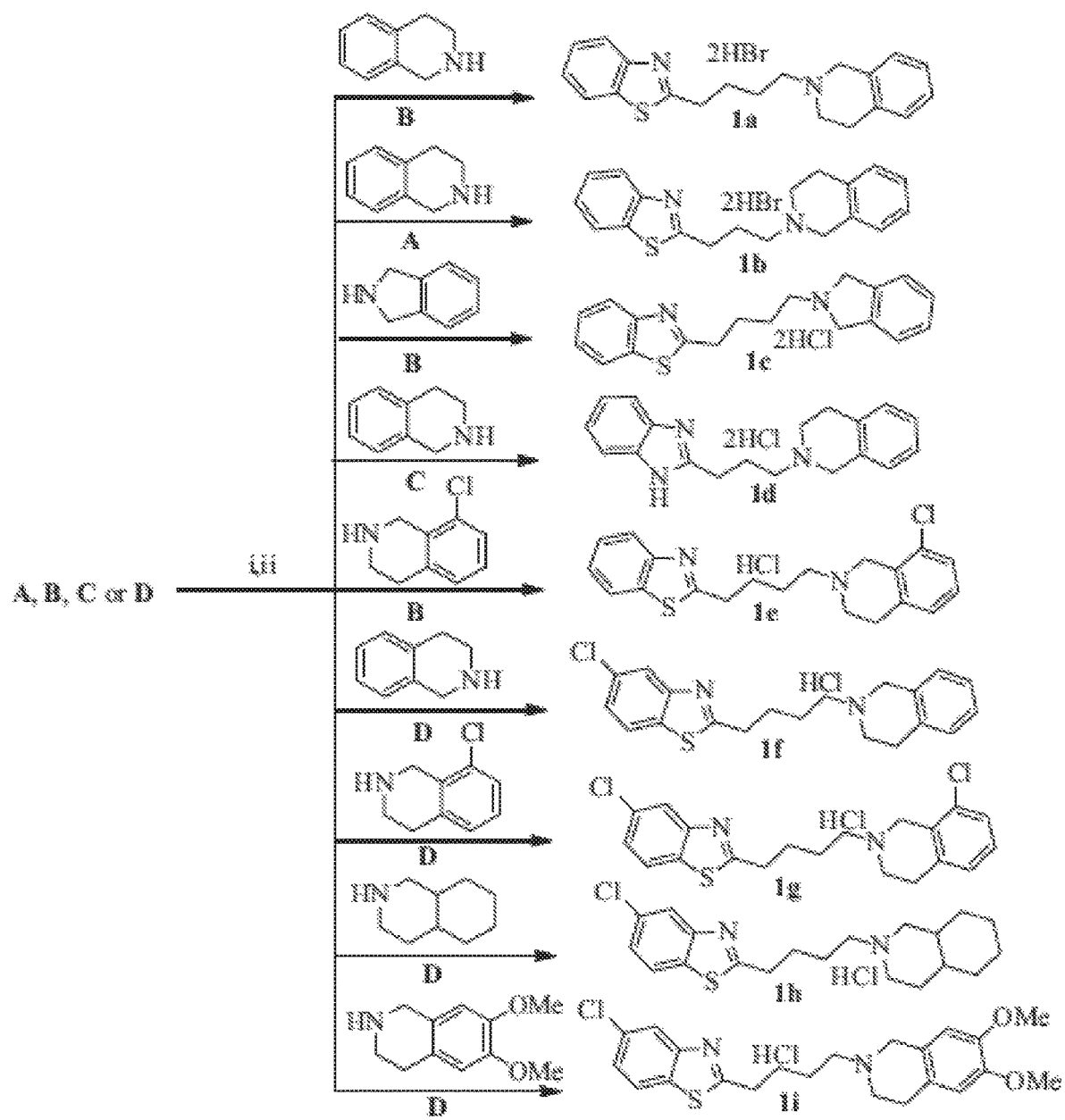
FIG. 11 illustrates scheme 8: Synthesis of compounds in Group 1 (Compounds 1a-1i). Reagents and conditions: (i) $K_2CO_3$ ($Et_3N$ for 1d), KI, DME, $CH_3CN$, or DMF (for 1d), reflux or rt (for 1d), 12-18 h.; (ii) ethereal HCl or HBr.

Compound 1b (FIG. 11) was prepared by coupling 2-(3-chloropropyl)benzo[d]thiazole (A, (FIG. 9)) as previously reported (Zhu et al., (2012) *Eur. J. Med. Chem.* 53: 124; Sampson et al., (2014) *Bioorg. Med. Chem.* 22: 3105; Peprah et al., (2012) *Bioorg. Med. Chem.* 20: 1671) to 1,2,3,4-tetrahydroisoquinoline (THIQ) under the general alkylation condition B that used $K_2CO_3$ as the base, KI as a catalyst and either acetonitrile ($CH_3CN$) or dimethoxyethane (DME) as the refluxing solvent. Alkylating agent C was synthesized according to a modified method (Bachman & Heisey (1949) *Am. Chem. Soc.* 71: 1985) outlined in FIG. 10 and was reacted with THIQ to afford compound 1d (FIG. 11). Compound 1e (FIG. 11) was prepared in a similar manner as 1b (FIG. 11) except that 8-chloro-1,2,3,4-tetrahydroisoquinoline was used in place of THIQ, and B was the alkylating agent. The alkylating agent D (FIG. 9) was obtained using a similar approach as was used to obtain alkylating agents A and B and was reacted with the various amines (THIQ, aromatic substituted THIQs and decahydroisoquinoline) as depicted in FIG. 11 to afford the corresponding compounds 1f-i (as shown in FIG. 11).

Figure 12:
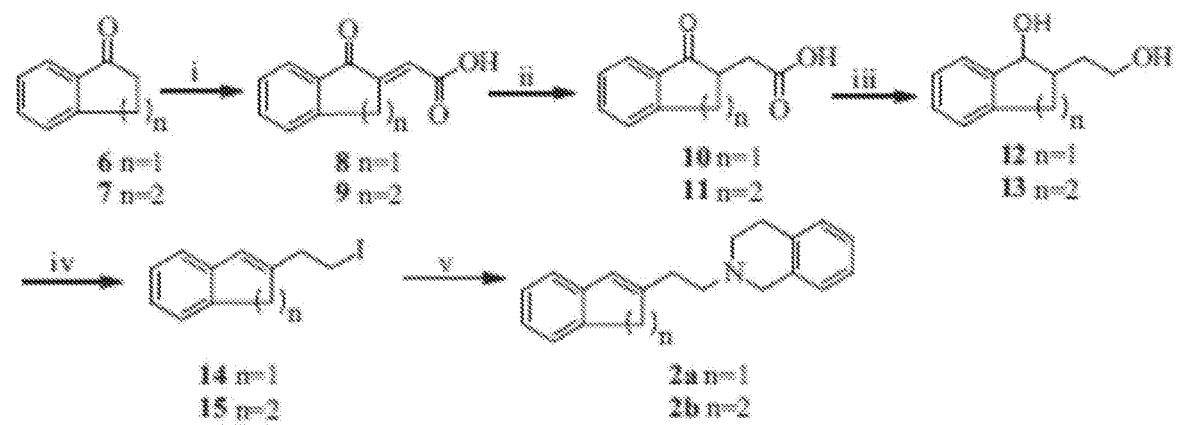
FIG. 12 illustrates scheme 9: Synthesis of the indene and dialin derivatives of THIQ. Reagents and conditions: (i) glyoxylic acid, $H_2SO_4$—$H_2O$ (1:4), dioxane, reflux; (ii) Pd/C ($H_2$), 40 psi, 48 h; (iii) $LiAlH_4$, toluene/ether, reflux; (iv) $PPh_3$, $I_2$, imidazole, DCM; (v) $K_2CO_3$, KI, $CH_3CN$, reflux.

To synthesize the indene 2a (FIG. 12) and the 1,2-dihydronapthalene analog 2b (FIG. 12) in group 2, the alkylating agents 14 and 15 were prepared following a four-step procedure (Scheme 9, FIG. 12). First, the commercially available indanone 6 (FIG. 12) and the α-tetralone 7 (FIG. 12) were separately refluxed with glyoxylic acid in an aqueous acid in a cross-aldol condensation reaction to produce the α,β-unsaturated ketones 8 and 9 (FIG. 12) respectively. The α,β-unsaturated keto function in 8 and 9 (FIG. 12) was then reduced using a palladium-carbon catalyzed hydrogenation reaction to afford the corresponding keto-acids 10 (FIG. 12) and 11 (FIG. 12) which were subsequently converted to the alcohols 12 (FIG. 12) and 13 (FIG. 12) under reductive conditions using $LiAlH_4$. The primary hydroxyl group was converted to an iodo group under Appel reaction conditions (Appel, R. (1975) *Angew. Chem. Int. Ed. Engl.* 14: 801). Interestingly, the Appel reaction also led to the generation of a styrene-like double bond seen in intermediates 14 (FIG. 12) and 15 (FIG. 12).

Figure 13:
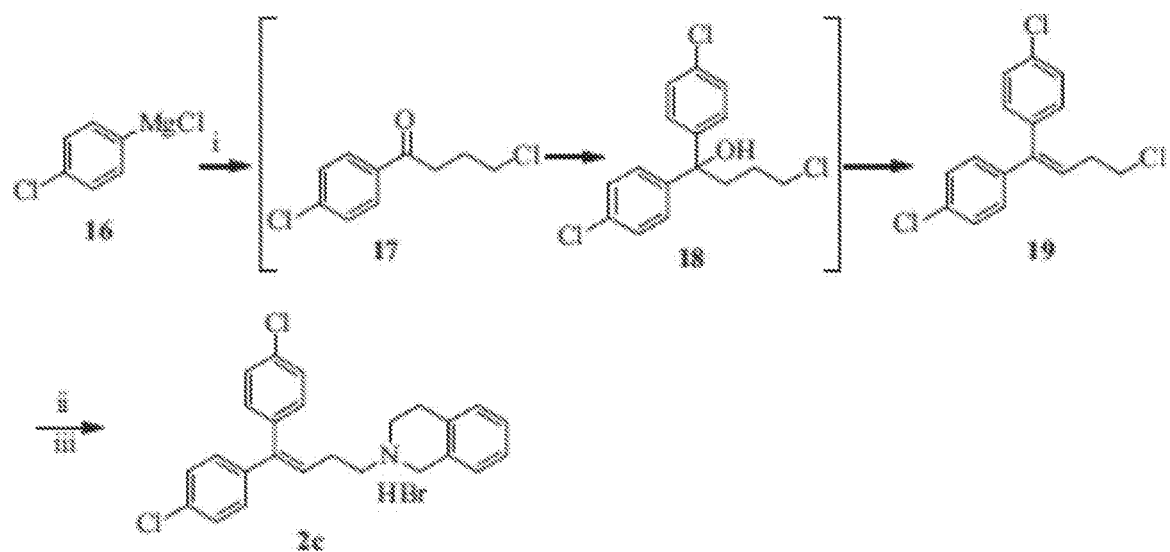
FIG. 13 illustrates scheme 10: Synthesis of bis-p-chlorophenyl analog of THIQ. Reagents and conditions: (i) 4-chlorobutyryl chloride, dry THF, rt; (ii) THIQ, $K_2CO_3$, KI, DME; (iii) ethereal HBr.

The bis-p-chlorobenzene alkylating agent 19 (FIG. 13) used to prepare compound 2c (FIG. 13) was serendipitously isolated in a previous attempt to form intermediate 17 (FIG. 13) from a reaction of the commercially available Grignard reagent 16 (FIG. 13) and 4-chlorobutyryl chloride (Scheme 10, FIG. 13). A plausible mechanism to explain the formation of this product is that the intended product 17 (FIG. 13) underwent further 1,2 addition of the Grignard reagent (4-chlorophenyl)magnesium chloride 16 (FIG. 13) to the carbonyl function to generate the tertiary alcohol 18 (FIG. 13) that dehydrated in the presence of $MgCl_2$ acting as a Lewis acid (catalyst) to produce 19 (FIG. 13). The isolated alkylating agent 19 (FIG. 13) was then coupled to THIQ under the general alkylation condition B to afford 2c (FIG. 13).

Figure 14:
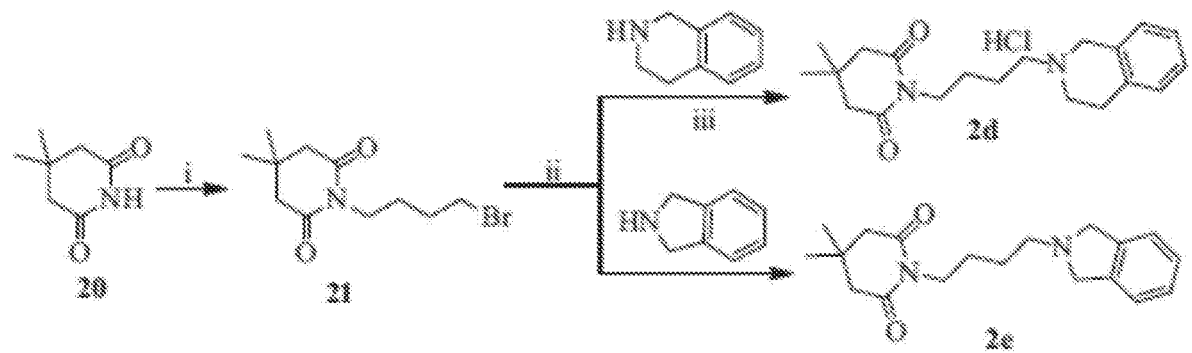
FIG. 14 illustrates scheme 11: Synthesis of dimethylglutarimide analogs of THIQ. Reagents and conditions: (i) 1,4-dibromobutane, $CH_3CN$, reflux; (ii) amine (THIQ for 2d, and isoindoline for 2e), $K_2CO_3$, $CH_3CN$, reflux; (iii) ethereal HCl.

In Scheme 11, (FIG. 14), the dimethylglutarimide analogs 2d (FIG. 14) and 2e (FIG. 14) were obtained through a simple two-step reaction. Commercially available dimethylglutarimide 20 (FIG. 14) was N-alkylated using dibromobutane and the resulting alkylbromide 21 (FIG. 14) coupled separately to THIQ and isoindoline to afford compounds 2d (FIG. 14) and 2e (FIG. 14), respectively.

Figure 15:
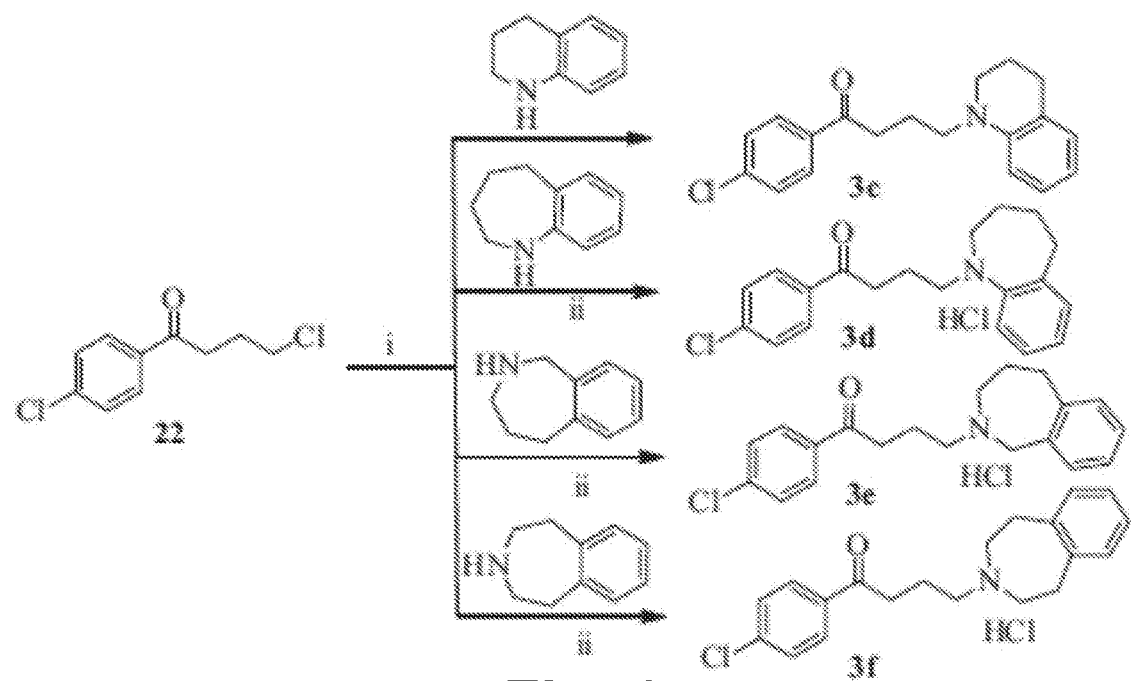
FIG. 15 illustrates scheme 12: Synthesis of p-chlorobutyrophenone analogs. Reagents and conditions: (i) appropriate amine, $K_2CO_3$, KI, DME, MW; (ii) ethereal HCl.
Figure 16:
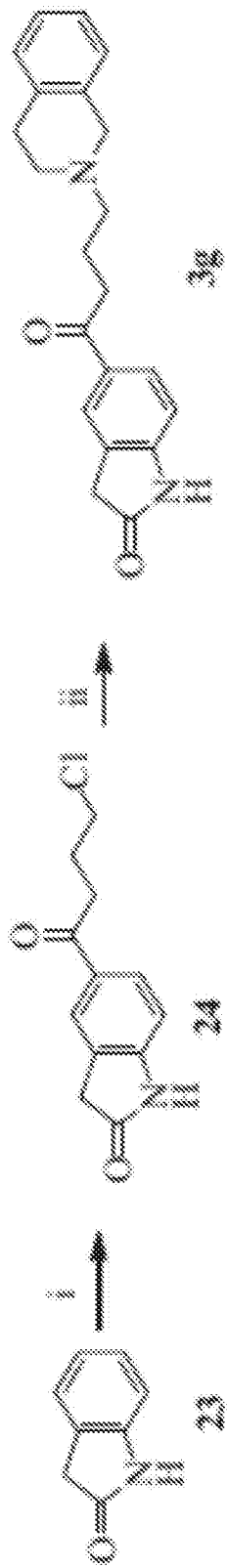
FIG. 16 illustrates scheme 13: Synthesis of the oxindole analog of THIQ. Reagents and conditions: (i) 4-chlorobutyryl chloride, $AlCl_3$, $CS_2$, 0°-rt; (ii) THIQ, $K_2CO_3$, KI, DME, MW.

Compounds 3c-3f (FIG. 15) were obtained via a one-step N-alkylation with the commercially available 4-chloro-1-(4-chlorophenyl)butane-1-one, 22 (FIG. 15) of the various amines (tetrahydroquinoline and tetrahydrobenzazepines) as depicted in Scheme 12, FIG. 15. To prepare compound 3g (FIG. 15), oxindole 23 (FIG. 16) was acylated under Friedel-Crafts acylation conditions to obtain the ketone 24 (FIG. 16) that was subsequently used to react with THIQ to obtain compound 3g (FIG. 16) (Scheme 13, (FIG. 16)). Preparation of compounds 3c-3g (FIG. 15) and 3i (FIG. 15) utilized microwave heating (general alkylation method A) that led to reduced reaction time (up to 60 min) and higher yields compared to conventional heating (general alkylation method B) (24-48 h). Compounds 3h-3j (FIG. 17) were prepared by N-alkylating THIQ using the indanone alkylating agents 25-27 (FIG. 17) (Scheme 14, FIG. 17)) (Sampson et al., (2014) *Bioorg. Med. Chem.* 22: 3105; Peprah et al., (2012) *Bioorg. Med. Chem.* 20: 1671).

2-(4-(3,4-dihydroisoquinolin-2(1H)-yl)butyl)benzo[d]thiazole (compound 1a (FIG. 18)) was previously reported (Zhu et al., (2012) *Eur. J. Med. Chem.* 53: 124) and serves as a lead compound for modification to better understand the structure affinity relationship (SAFIR) associated with binding to key CNS receptors. The binding affinity data of compound 1a (FIG. 18) at the D2-like receptors (Ki: D2=167 nM, D3=8.7 nM and D4=67 nM), 5-HT1A (Ki=10 nM) and the 5-HT7 receptor (Ki=22 nM) are reported in Table 3 (Example 61).

Figure 18:
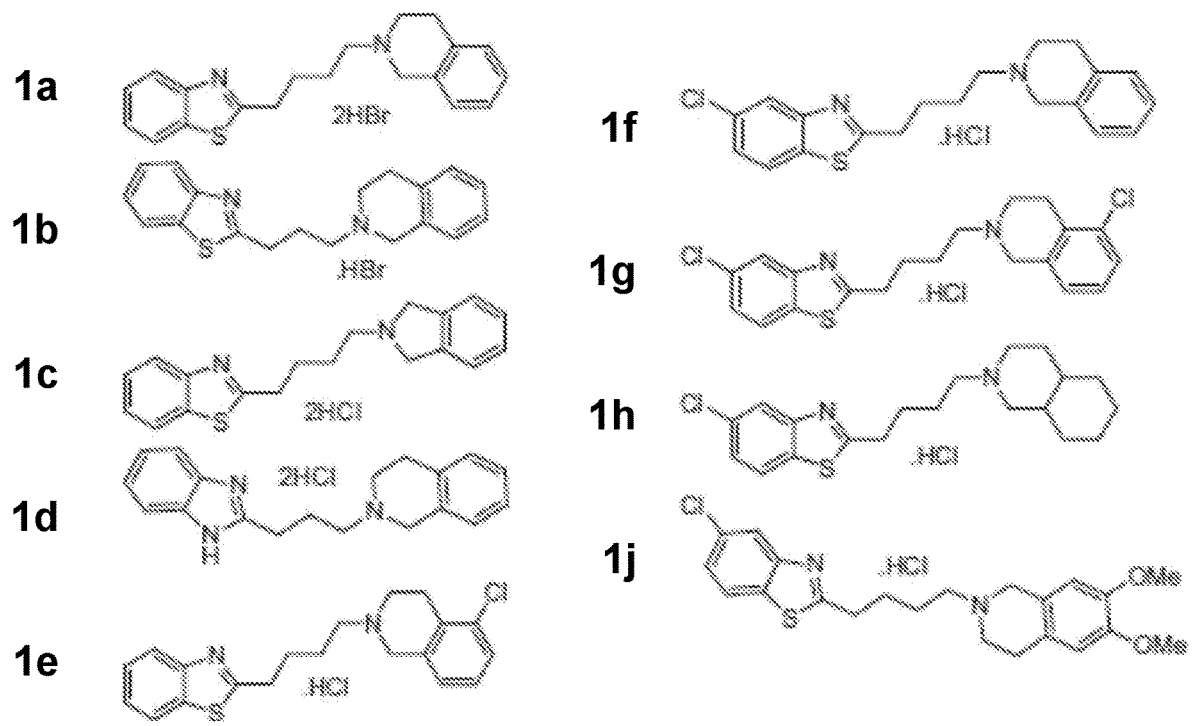
FIG. 18 illustrates structures of Group 1 compounds 1a-1i.
Figure 19:
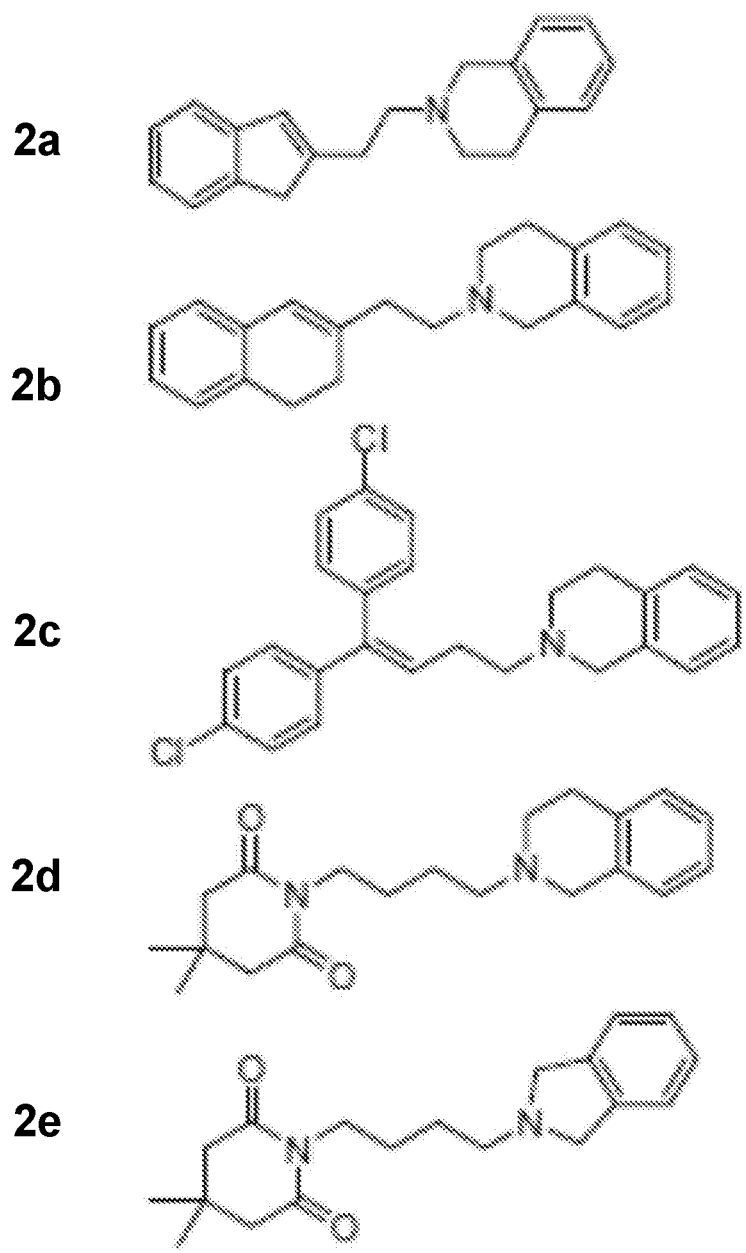
FIG. 19 illustrates structures of Group 2 compounds 2a-2e.
Figure 20:
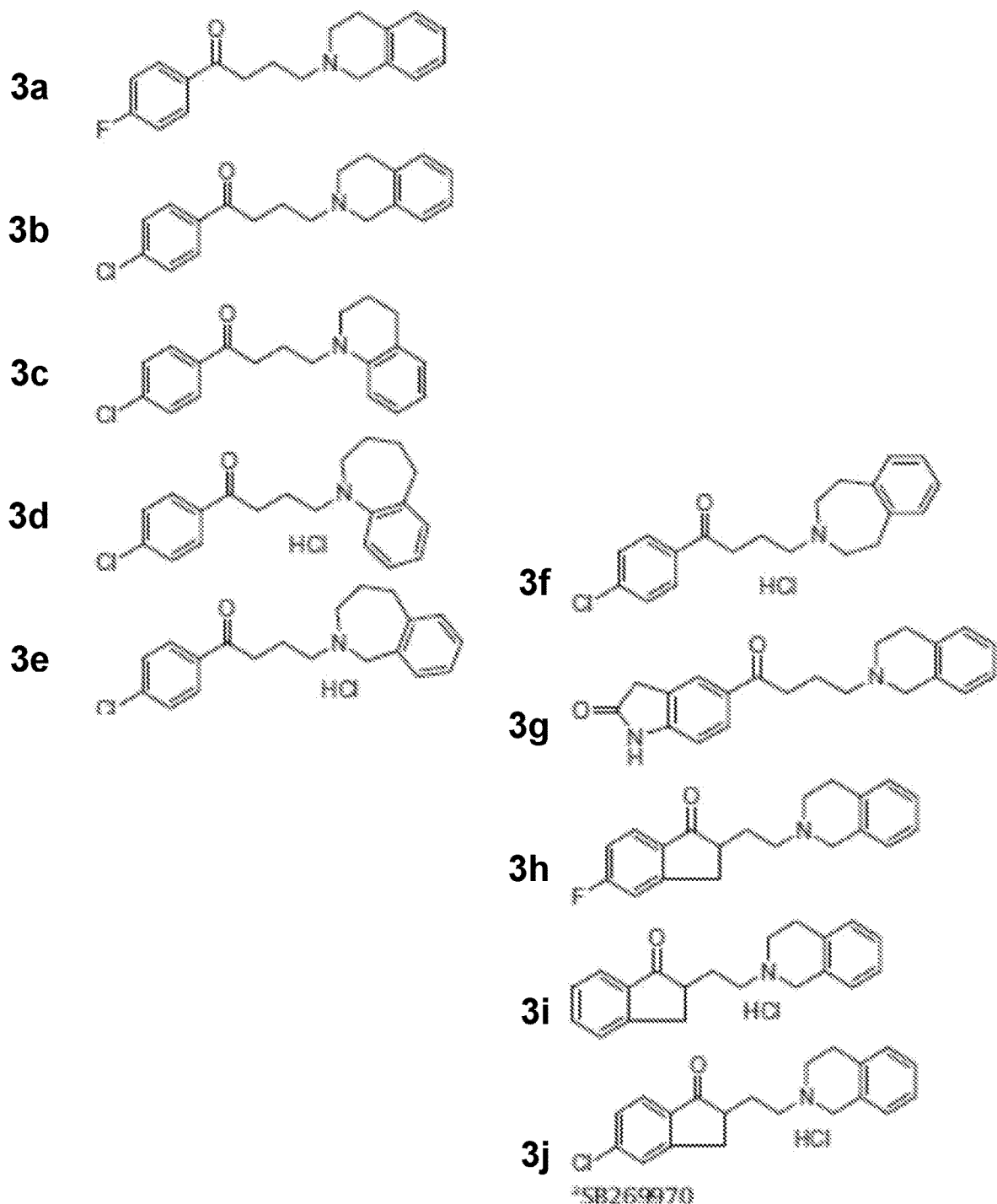
FIG. 20 illustrates the structures of the Group 3 compounds 3a-3j.
Figure 21:
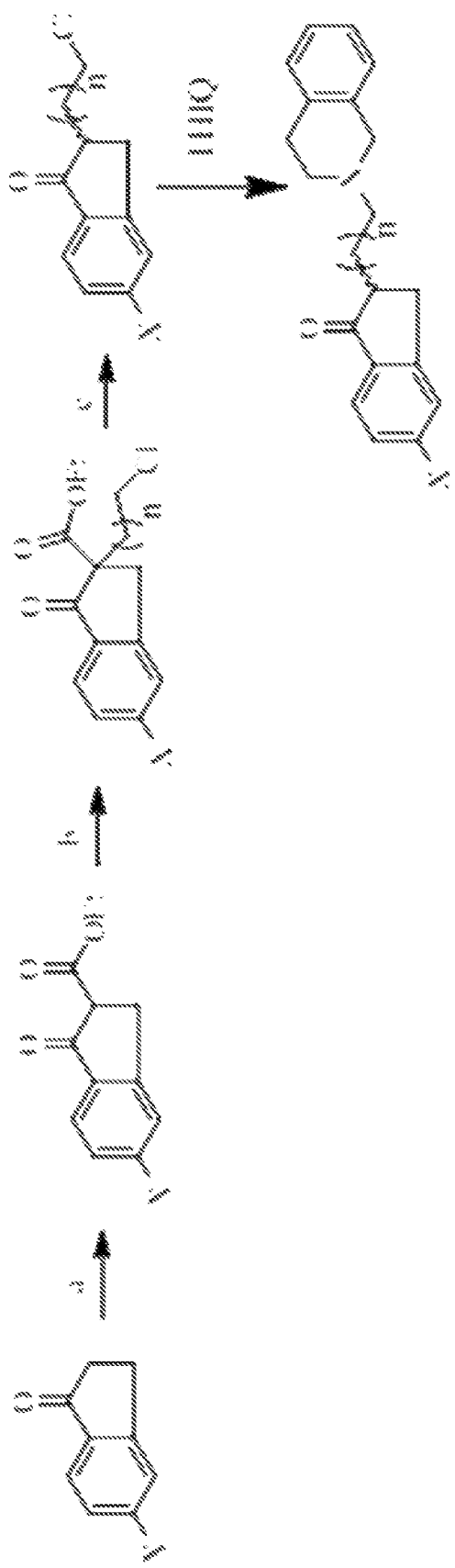
FIG. 21 illustrates the general scheme for the synthesis of agents. (a) NaH, DEC, 0° C.-rt, 12 h, (b) NaH, DMF, 1-bromo-2-chloroethane (for 6e) or 1-bromo-4-chlorobutane (for 6f), rt, 18-24 h. c. Conc. HCl in AcOH (glacial), MW.
Figure 22:
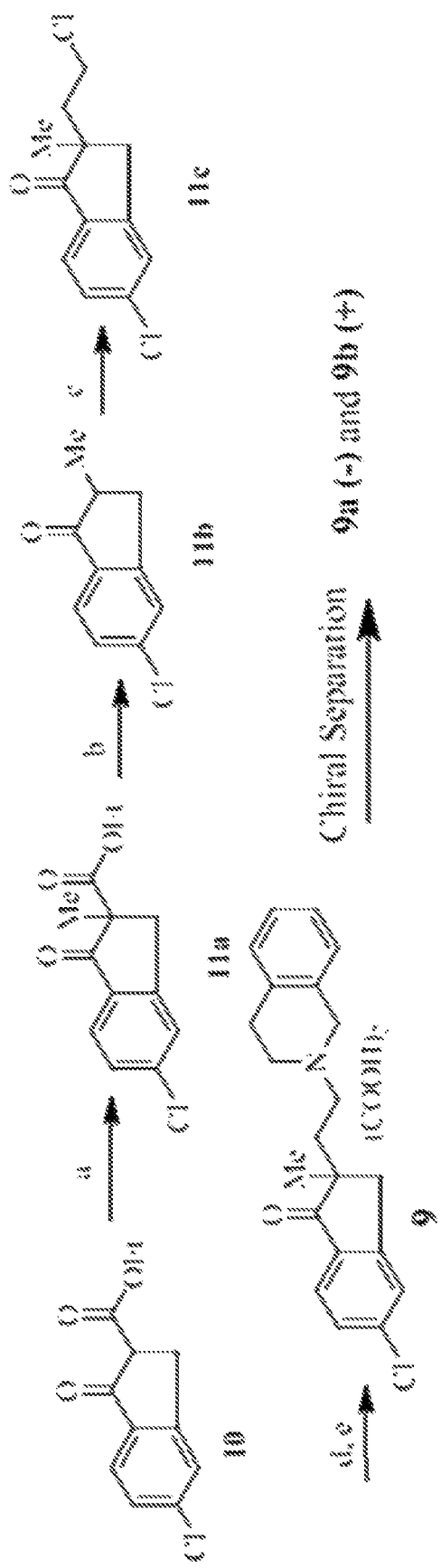
FIG. 22 illustrates scheme: Synthesis of compound 9. Reagents and conditions: (a) NaH, DMF, MeI, rt, 24 h, (b) Conc. HCl in AcOH (glacial), MW, (c) NaH, DMF, 1-bromo-2-chloroethane, rt, 24 h, (d) THIQ, $K_2CO_3$/KI, toluene, MW, (e) ethereal oxalic acid.

To this end, a SAFIR study was initiated to explore the effect of structural changes in the benzothiazole moiety (segment A), the alkyl linker (segment B), and the tetrahydroisoquinoline moiety (segment C) of 1a (FIG. 18) on binding affinity at the various CNS receptors. This study led to the generation of three structural types of compounds, the benzothiazoles, cycloalkyl/cycloalkylamines and butyrophenone analogs classified as Group 1, 2, and 3 agents respectively, as shown in FIGS. 18-20.

Shortening the butyl linker in segment B of 1a (FIG. 18) to a three-carbon chain (1b (FIG. 18)), led to a lower affinity for all the DA and 5-HT receptors investigated except at the D4 receptor where a moderate increase in affinity was observed. Replacing the THIQ ring in 1a (FIG. 18) with isoindoline (1c (FIG. 18)) also resulted in decreased binding affinity to all the receptors under consideration. Compound 1d (FIG. 18) was prepared to explore the effect of replacing benzothiazole moiety (segment A) of compound 1b (FIG. 18) with benzimidazole on binding affinity. The binding data suggest that the benzothiazole was preferred at all the receptors evaluated. Thus, the data (Table 3, Example 61) for compounds 1a-1d (FIG. 18) suggests a benzothiazole with a 4-carbon spacer attached to THIQ is preferred for the DA and 5-HT receptors explored.

Compound 1e (FIG. 18), with an 8-chloro substitution on segment C of 1a (FIG. 18) did not result in significant changes in binding affinities suggesting substitution on the THIQ ring is tolerated at least at the 8-position. Similarly, a 5-chloro substitution on the benzothiazole moiety (1f (FIG. 18)) was tolerated at all the receptors except for the D3 and D4 receptors. However, substituting the same substituents simultaneously on the benzothiazole and the THIQ moieties (1g (FIG. 18)) resulted in diminished affinities for all the receptors. Compound 1h (FIG. 18) was synthesized to explore the need for the aromatic ring in THIQ for binding to the receptors under consideration. While the D2 and D3 receptors suffered significant reductions in affinity, the 5-HT1A, 5-HT2A, 5-HT2C and 5-HT7 were essentially unaffected. Similarly, introducing the 9,10-dimethoxy group on 1f (FIG. 18) to form 1i (FIG. 18), ill-affected binding affinity to the D2-like receptors but not the serotonin receptors under consideration. None of the benzothiazole analogs displayed high affinity Ki values for the receptors H1 and 5-HT2C that have been associated with metabolic and sedative side effects (Rothman et al., (2000) Circulation 102: 2836; Kroeze et al., (2003) Neuropsychopharmacol. 28: 519; Miller, D. D. (2004) Prim. Care Companion J. Clin. Psychiatry 6: 3; Opgen-Rhein et al., (2010) Pharmacogenomics 11: 773). On the other hand, there is high affinity binding and significant variability in the binding to the 5-HT2B receptors with a range of 7.0-327 nM.

To further evaluate the structural requirements for segment A/B binding affinity, four analogs, 2a-d (FIG. 19) were synthesized and the binding affinity constants are reported in Table 4, Example 61. Compounds 2a (FIG. 19) and 2b (FIG. 19) can be viewed as partially restricted butyl spacers using cyclopentene and cyclohexene rings. Both compounds displayed diminished binding affinity for the D2R and showed no definitive trends at other clinically relevant receptors. Compounds 2c (FIG. 19), 2d (FIG. 19) and 2e (FIG. 19) generally showed no significant binding affinities for any of the receptors under consideration.

Compounds with the butyrophenone alkyl group (group 3) are analogs of either compound 3a (FIG. 20) or 3b (FIG. 20).

Because of the promising binding affinity profiles of these butyrophenones at the relevant CNS receptors (Table 3, Example 61), the SAFIR of these compounds was explored. To begin with, the role of the position of the nitrogen in segment C was examined. The THIQ moiety in 3b (FIG. 20) was replaced with tetrahydroquinoline and 2,3,4,5-tetrahydro-1Hbenzo[b]azepine to produce compounds 3c (FIG. 20) and 3d (FIG. 20) respectively, resulting in the formation of aromatic nitrogen atoms in both analogs. Significantly, this change resulted in no apparent receptor binding affinity at the selected CNS receptors. While not wishing to be bound by any one theory, it is possible that an aliphatic nitrogen atom with a higher pKa is more desirable in these compounds for binding to the receptors. Alternatively, the positioning of the nitrogen atom proximal to the phenyl ring may have prevented optimal interaction with the complementary functional group at the receptors.

Compounds 3e (FIG. 20) and 3f (FIG. 20) were synthesized to further explore the above. Thus, moving the nitrogen away from a direct interaction with the phenyl ring resulted in a minor improvement in the binding potencies at the DA and 5-HT receptor subtypes when compared to 3c (FIG. 20) and 3d (FIG. 20) but fell short of the original affinities seen with 3b (FIG. 20). Replacing the 4-chlorophenyl group with an oxindole bicyclic moiety to form 3g (FIG. 20) produced no significant improvements in binding affinity at the various receptors.

Compounds 3h-3j (FIG. 20) were the partially restrained analogs of the butyrophenone analogs 3a (FIG. 20) or 3b (FIG. 20). Restricting the keto group into an indanone led to some rather interesting observations as reported in Table 5, Example 61. First, compound 3h (FIG. 20), the restrained analog of 3a (FIG. 20), records over 15-fold decrease in potency at the D2R (Ki=750 nM), compared to 3a (FIG. 20) (Ki=49 nM), retained activity at the 5-HT1A (Ki=19 nM) and an awe-inspiring low nanomolar binding affinity at the 5-HT7 receptor (Ki=1.6 nM). This is of biological significance because of the paucity of selective dual 5-HT1A and 5-HT7 receptor ligands in the literature (Canal et al., (2014) FASEB J. 28: 1059). Also, a growing body of knowledge suggests that the 5-HT7 receptor controls normal circadian rhythm, sleep, mood, memory and learning, and cognition (Horiguchi et al., (2011) J. Pharmacol. Exp. Ther. 338: 605; Hedlund & Sutcliffe (2004) Trends Pharmacol. Sci. 25: 481; Nikiforuk, A. (2015) CNS Drugs 29: 265) and may, therefore, serve as a plausible target for treating neuropsychiatric disorders such as schizophrenia and mood disorders. Having obtained 3h (FIG. 20) as a possible lead, the effect of removing the fluoro group in 3h (FIG. 20) to produce compound 3i (FIG. 20) was investigated. This resulted in over 165-fold decrease in binding affinity at the 5-HT7 receptor, which suggested that a halo-phenyl moiety may be required for this 5-HT7 affinity. Further confirmation of this thought was observed by replacing the fluoro atom with a chloro atom to form compound 3j (FIG. 20) with a sub-nanomolar binding affinity constant (Ki=0.5 nM) at the 5-HT7 receptor. Compound 3j (FIG. 20) compares favorably with the binding affinity of SB269970 (pKi=1.3 nM), the selective 5-HT7 antagonist, albeit it has a dual binding affinity profile (Lovell et al., (2000). J. Med. Chem. 43: 342). Similarly, when compared to the most potent analogs from modifications to the lead compound, UCM-5600 (Medina et al., (2009) J. Med. Chem. 52: 2384) and a recently reported arylindole series,1-(naphthyl)indole derivative (Sagnes et al., (2014) Eur. J. Med. Chem. 75: 159) 30 compound 3j (FIG. 20) is about 9 to 14-fold more potent at the 5-HT7 receptor and over 4 to 10-fold higher affinity at the 5-HT1A receptor. Overall, the binding affinity constants of the indanone analogs fared poorly at the D2-like receptors as well as the culprit 5-HT receptors.

Accordingly, beginning with compound 1a (FIG. 18) as an initial lead molecule of the benzothiazole series, several alkylated THIQ analogs with potent and desirable multi-receptor binding features especially at the 5-HT1A and 5-HT7 receptors have been obtained. The 5-chloro-indanone analog 3j (FIG. 20), displaying low nanomolar and a sub-nanomolar affinity values at the 5-HT1A and the 5-HT7 receptors respectively, is an addition to the rather scarce group of dual 5-HT1A and 5-HT7 receptor selective ligands in the literature that can be used to probe the role of these receptors in treating the affective and cognitive diseases of CNS origin.

One aspect of the disclosure, therefore, encompasses embodiments of a serotonin receptor ligand having the formula:

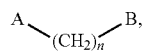

or a salt thereof, wherein: n=2, 3, or 4; A can be selected from the group consisting of:

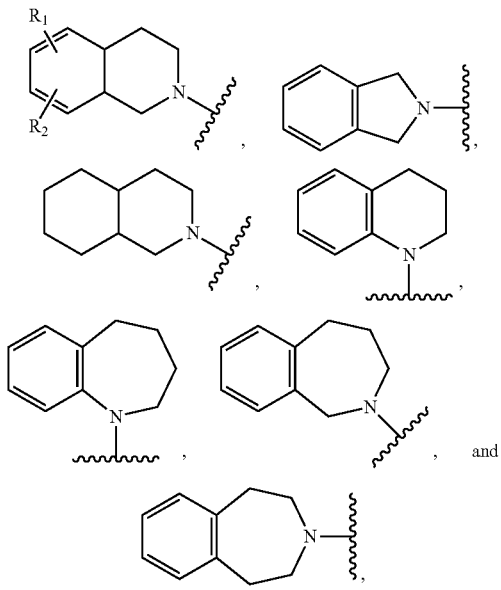

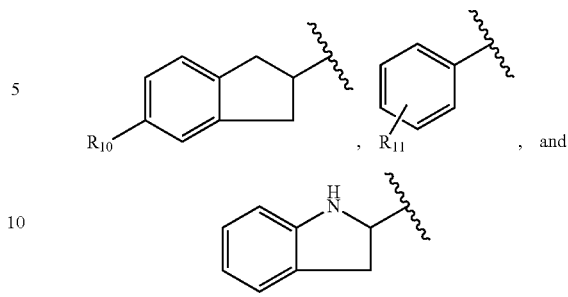

, and

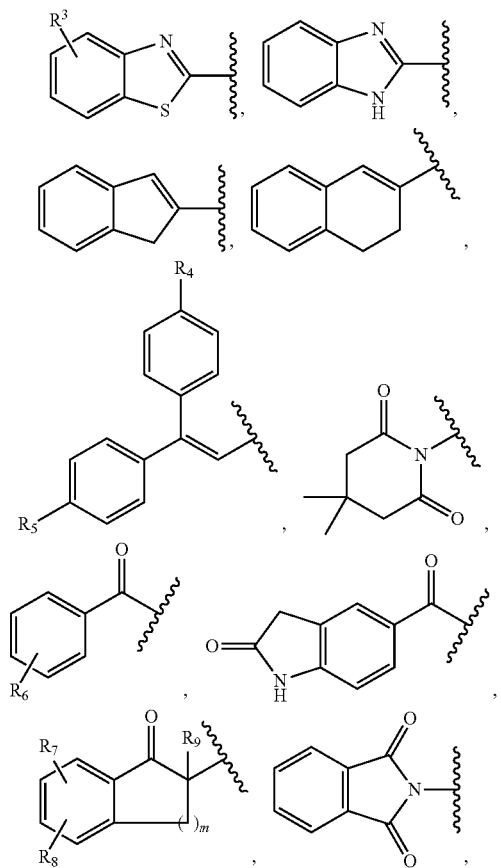

wherein if $R_1$ is H or a halogen, $R_2$ is H, and if $R_1$ is a methoxy, $R_2$ is an H or a methoxy; and B is selected from the group consisting of:

wherein: $R_3$ is H or a halogen; $R_4$ and $R_5$ are each independently H or a halogen; $R_6$ is H, CN, CONH2, H3CO, OH, or a halogen; $R_7$ and $R_8$ are each independently H or a halogen; $R_9$ is H, an alkyl group, or a terminally substituted alkyl group having a polar functional group, and $R_{10}$, and $R_{11}$ are each H or a halogen, and m=1, 2, 3, or 4.

In some embodiments of this aspect of the disclosure the serotonin receptor ligand can be selected from the group consisting of:

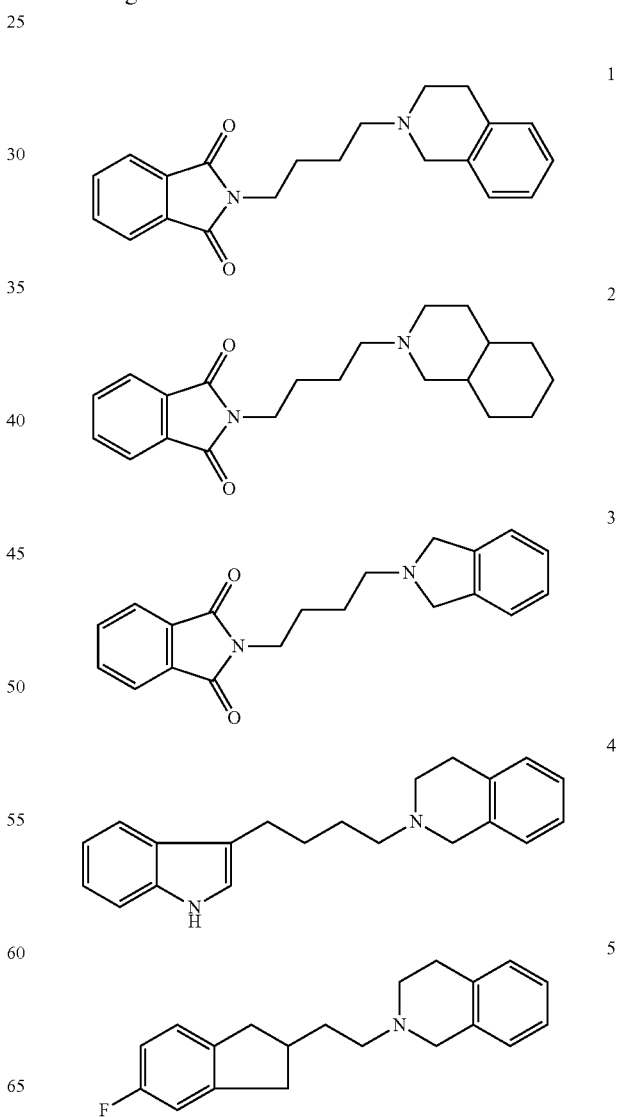

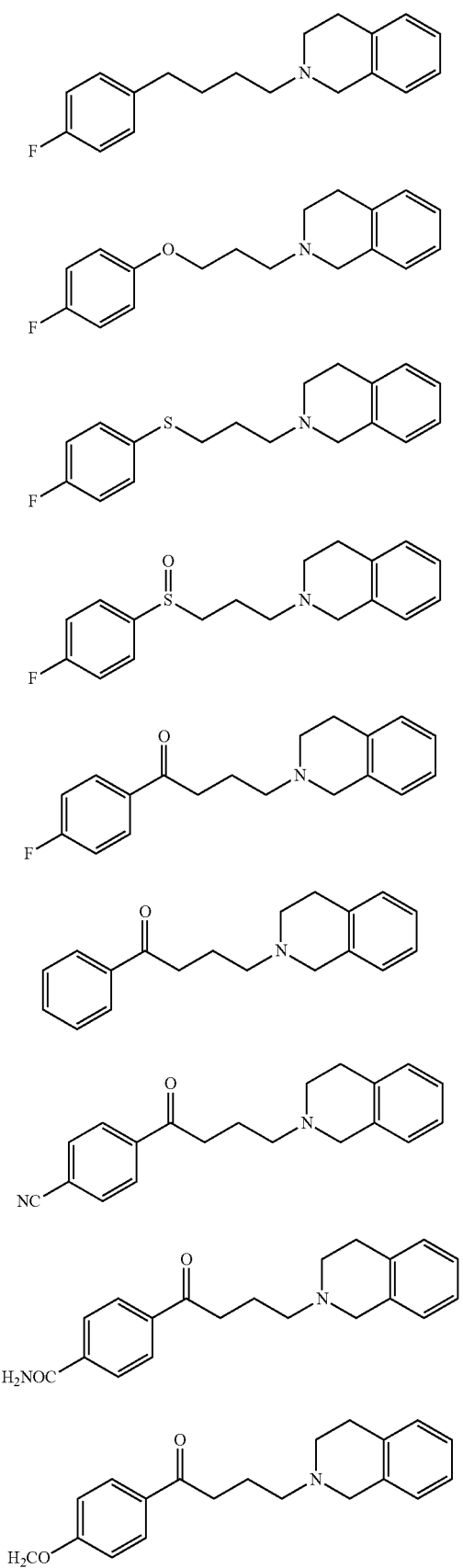
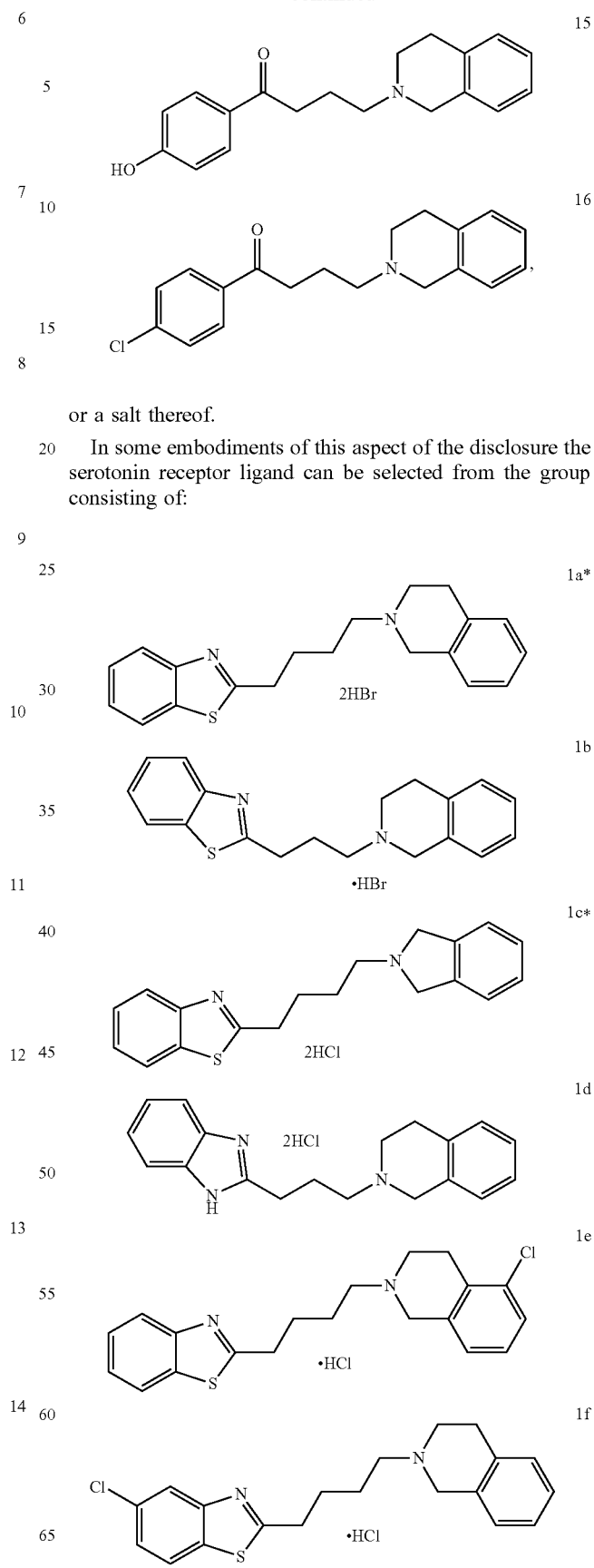
or a salt thereof.
In some embodiments of this aspect of the disclosure the serotonin receptor ligand can be selected from the group consisting of:

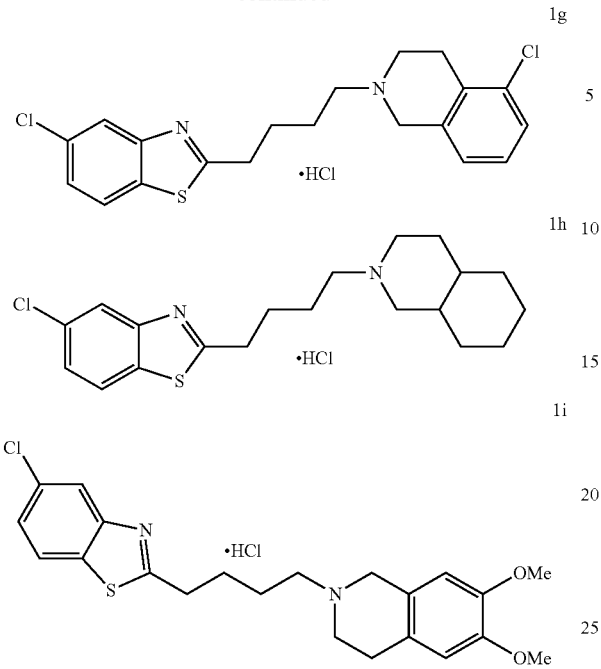
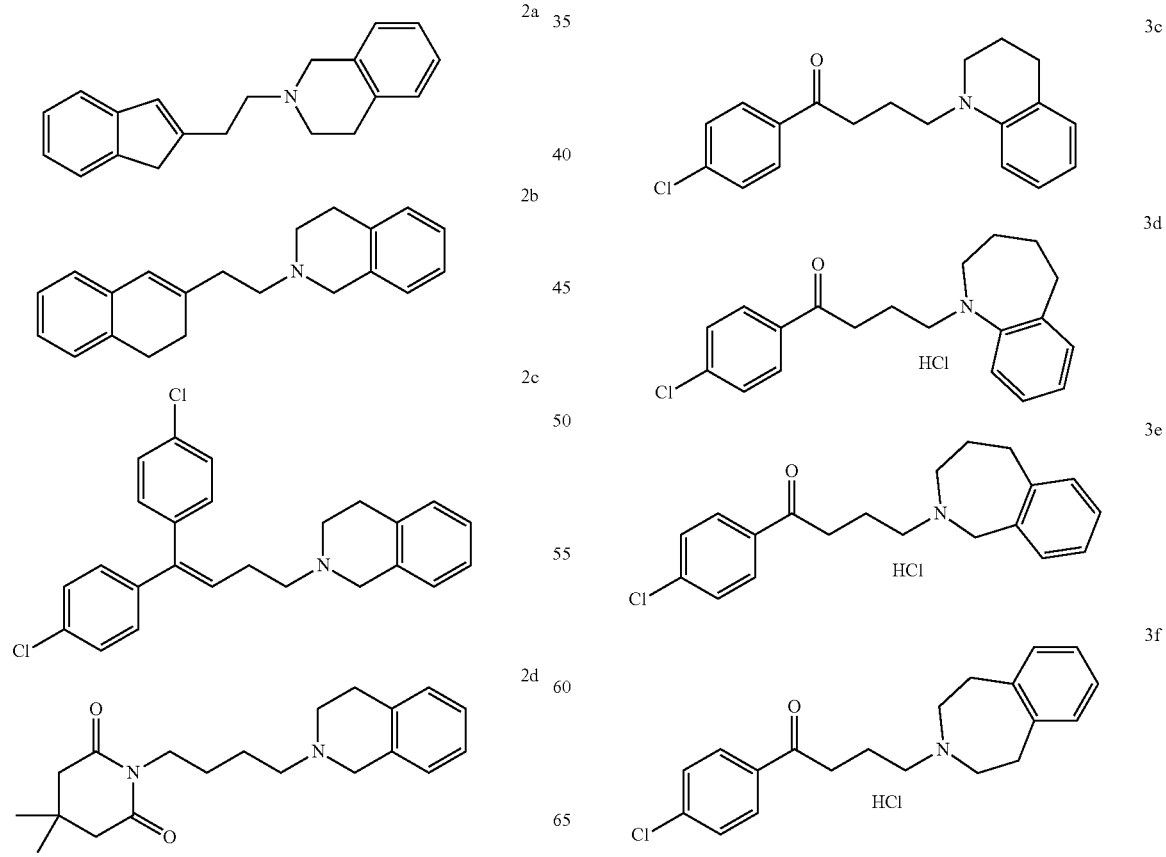
or a salt thereof.
In some embodiments of this aspect of the disclosure the serotonin receptor ligand can be selected from the group consisting of:

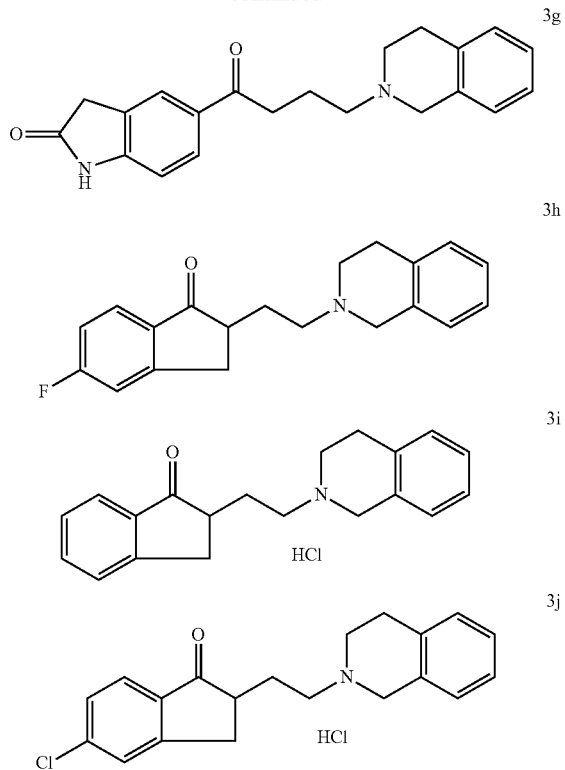

or a salt thereof.

In some embodiments of this aspect of the disclosure the serotonin receptor ligand can be selected from the group consisting of wherein n=2, 3, or 4, p=1, 2, 3, or 4, X and Z are each independently H or a halogen, and Y is $CH_3$ or OH, or a salt of any thereof.

In one embodiment of this aspect of the disclosure the serotonin receptor ligand has the formula:

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Experimental: Melting points were determined on a Gallenkamp (UK) apparatus and are uncorrected. All NMR spectra were obtained on a Varian 300 MHz Mercury Spectrometer and the free induction decay (FID) data were processed using Mestrelab's Mnova NMR software (version 8.1) to obtain the reported NMR data. Elemental analyses were carried out by Atlantic Microlab, Inc., Norcross, Ga., and are within 0.4% of theory unless otherwise noted. Flash chromatography was performed using COMBIFLASH® with Davisil grade 634 silica gel. Starting materials were obtained from Sigma-Aldrich and were used without further purification. All microwave-assisted syntheses (MW) were carried out using a BIOTAGE INITIATOR®.

Example 2

Synthesis of 2-(4-Bromobutyl)isoindoline-1,3-dione, 1b (FIG. 1): A mixture of potassium phthalimide 1a (0.93 g, 5 mmol) and 1,4-dibromobutane (5.4 g, 25 mmol) was stirred in dry DMF (10 mL) at 100° C. for 12 h. The condenser was then set for distillation, and the excess of 1,4-dibromobutane and DMF was removed under reduced pressure. The crude product obtained was purified by column chromatography (silica gel, ethyl acetate/light petroleum 1:50) to afford intermediate 1b (FIG. 1) as a colorless solid. $^1$H NMR (CDCl$_3$): δ 7.87-7.84 (2H, m), 7.74-7.71 (2H, m), 3.73 (2H, t, J=6.9 Hz), 3.45 (2H, t, J=6.3 Hz), 1.90-1.88 (4H, m).

Example 3

General alkylation procedure for compounds 1-3 (FIG. 1): A mixture of 1b (FIG. 1) (1 equiv), an appropriate amine (1.2 equiv), KI (100 mg), and K$_2$CO$_3$ (10 equiv), in CH$_3$CN (15 mL) or DME was refluxed for 12-24 h. The reaction progress was monitored by TLC and at completion, the mixture was cooled to room temperature, solvent removed, the resulting residue loaded onto a cartridge and purified by flash chromatography using an EtOAc/hexane gradient up to 80% EtOAc to give the pure desired products.

Example 4

2-(4-(3,4-Dihydroisoquinolin-2(1H)-yl)butyl)isoindoline-1,3-dione, 1 (FIG. 1): Following the general alkylation procedure described in Example 39 and using THIQ as the amine, compound 1 (FIG. 1) was obtained as the free base. Yield: 22%, mp: 68-69° C. $^1$H NMR (DMSO-d$_6$): δ 7.86-7.79 (4H, m), 7.07-6.98 (4H, m), 3.58 (2H, t, J=6.9 Hz), 3.47 (2H, s), 2.75 (2H, t, J=5.4 Hz), 2.58 (2H, t, J=6.0 Hz), 2.43 (2H, t, J=6.9 Hz), 1.68-1.48 (4H, m). Calculated for C$_{21}$H$_{22}$N$_2$O$_2$.0.2H$_2$O; C, 74.62; H, 6.68; N, 8.29; Found: C, 74.55; H, 6.55; N, 8.25.

Example 5

2-(4-(Octahydroisoquinolin-2(1H)-yl)butyl)isoindoline-1,3-dione, 2 (FIG. 1): Using decahydroisoquinoline as the amine, compound 2 (FIG. 1) was prepared similarly to 1 above. Yield: 12%, mp: 64-65° C. $^1$H NMR (CDCl$_3$): δ 7.84-7.82 (2H, dd, J=3.0, 8.7 Hz), 7.70 (2H, dd, J=3.0, 9.0 Hz), 3.70 (2H, t, J=7.2 Hz), 2.91 (1H, d, J=8.1 Hz), 2.75 (1H, d, J=9.0 Hz), 2.31 (2H, s), 1.77 (1H, t, J=7.2 Hz), 1.71-1.48 (1H, m), 1.26-1.19 (4H, m), 0.98-0.87 (2H, m). Calculated for C$_{21}$H$_{28}$N$_2$O$_2$; C, 74.08; H, 8.29; N, 8.23; Found: C, 73.82; H, 8.09; N, 8.19.

Example 6

2-(4-(Isoindolin-2-yl)butyl)isoindoline-1,3-dione, 3 (FIG. 1): Following the general alkylation procedure in Example 39 and using isoindoline as the amine, compound 3 (FIG. 1) was obtained as the free base. Yield: 21%, mp: 95-96° C. $^1$H NMR (DMSO-d$_6$): δ 7.88-7.78 (m, 4H), 7.20-7.12 (m, 4H), 3.76 (s, 4H), 3.59 (t, 2H, J=5.7 Hz), 2.63 (t, 2H, J=7.2 Hz), 1.70-1.44 (m, 4H). Calculated for C$_{20}$H$_{20}$N$_2$O$_2$-0.11 H$_2$O; C, 72.78; H, 6.11; N, 8.49; Found: C, 72.75; H, 6.16; N, 8.12.

Example 7

Synthesis of 3-(4-iodobutyl)-1H-indole, 2b (FIG. 2): To a solution of indole-3-butyric acid 2a (FIG. 2) (2 g, 9.8 mmol) dissolved in dry THF (30 mL) and cooled to 0° C. was added portion-wise LiAlH$_4$ (2.2 g, 59 mmol, 6 equiv) in dry THF. The mixture was allowed to warm to room temperature (rt) with stirring for 18 h. The reaction mixture was cooled to 0° C. and a saturated solution of Na$_2$SO$_4$ (20 mL) was added in a dropwise manner over the period of 30 min. The resulting white precipitate was filtered, the filtrate washed with EtOAc (2×100 mL), the pooled organic phase washed with water (50 mL) and saturated brine solution (50 mL), dried over anhydrous Na$_2$SO$_4$ and the solvent removed under reduced pressure to obtain the crude product. The crude 3-(4-hydroxybutyl)-1H-indole was used for the next step without further purification.

The crude obtained was converted to compound 2b (FIG. 2) following a reported procedure (Smith & Takacs (2010) Am. Chem. Soc. 132). Briefly, to a stirred solution of PPh$_3$ (4.46 g, 17.0 mmol) and imidazole (1.58 g, 17.0 mmol) in DCM (45 mL) at 0° C., was added I$_2$ (4.32 g, 17.0 mmol) and the reaction mixture was stirred at this temperature for 30 min. Thereafter, a solution of crude 3-(4-hydroxybutyl)-1H-indole (2.30 g, 12.2 mmol) in DCM (5 mL) was added, the reaction mixture was allowed to warm to rt and stirred for 12 h. The crude product was directly purified using silica gel on CombiFlash with gradient up to 40% EtOAc in hexanes to afford compound 2b (FIG. 2) (2.40 g) as an oily liquid. Yield: 66%. $^1$H NMR (CDCl$_3$): δ 7.91 (1H, s). 7.59 (1H, d, J=8.1 Hz), 7.35 (1H, d, J=8.1 Hz), 7.22-7.17 (1H, t, J=6.9 Hz), 7.12 (1H, m), 6.97 (1H, d, J=2.1 Hz), 3.22 (2H, t, J=6.9 Hz), 2.84 (2H, t, J=6.9 Hz), 1.96-1.76 (4H, m).

Example 8

2-(4-(1H-Indol-3-yl)butyl)-1,2,3,4-tetrahydroisoquinoline, 4 (FIG. 2): Following the general alkylation procedure described in Example 39 and using the obtained 2b (FIG. 2) as the alkylating agent, compound 4 (FIG. 2) was obtained. Yield: 52%, mp: 139-140° C. $^1$H NMR (CDCl$_3$): δ 7.96 (1H, s), 7.62-7.60 (1H, d, J=8.4 Hz), 7.35 (1H, d, J=7.8 Hz), 7.21-7.15 (1H, m), 7.13-7.07 (4H, m), 7.01-6.98 (2H, m), 2.90 (2H, t, J=5.7 Hz), 2.81 (2H, t, J=6.9 Hz), 2.73 (2H, t, J=6.0 Hz), 2.56 (2H, t, J=7.2 Hz), 1.80-1.69 (6H, m). Calculated for $C_{21}H_{24}N_2$; C, 82.85; H, 7.97; N, 9.20; Found: C, 82.65; H, 7.97; N, 8.97.

Example 9

Synthesis of 2-(2-chloroethyl)-5-fluoro-2,3-dihydro-1H-indene, 3b (FIG. 3): Amalgamated zinc was prepared by stirring a mixture of zinc (1.2 g), $HgCl_2$ (0.12 g) in 5 mL water with conc. HCl (0.1 mL) at room temperature. After stirring for 5 min, the mixture was decanted and followed by adding in order water (1 mL), conc HCl (1.75 mL), toluene (10 mL), and then 2-(2-Chloro-ethyl)-5-fluoro-indan-1-one 3a (FIG. 3) (2 g, 9.43 mmol), synthesis of which was previously reported[23] The mixture was refluxed with stirring for 12 h. The solid was filtered off, aqueous layer was diluted with EtOAc (200 mL), washed with water, and then saturated $NaHCO_3$ (50 mL). The organic layer was dried over $Na_2SO4$, and filtered. The filtrate was concentrated in vacuo followed by column chromatography on silica gel to afford 3b (FIG. 3), 1.68 g, Yield 90%. $^1$H NMR ($CDCl_3$): δ 7.09 (1H, dd, J=4.8, 7.8 Hz), 6.85 (2H, m), 7.2 Hz), 3.04 (2H, m), 2.70 (1H, m), 2.56 (2H, m), 1.98 (2H, m)

Example 10

2-(2-(5-Fluoro-2,3-dihydro-1H-inden-2-yl)ethyl)-1,2,3,4-tetrahydroisoquinoline hydrochloride, 5 (FIG. 3): Alkylating agent 3b (FIG. 3) was reacted with THIQ following the general alkylation procedure described in Example 39 to obtain compound 5 (FIG. 3) as its HCl salt. Yield: 42%, mp: 211-212° C. $^1$H NMR (DMSO-$d_6$): 10.85 (1H, s), 7.19 (5H, m), 7.02 (1H, d, J=9.0 Hz), 6.92 (1H, t, J=9.0 Hz), 4.51 (1H, m), 4.27 (1H, m), 3.67 (1H, m), 3.40 (1H, m), 3.23 (4H, m), 3.02 (4H, m), 2.60 (1H, m), 1.98 (2H, m). Calculated for $C_{20}H_{23}ClFN$: C, 72.00; H, 6.95; N, 4.20; Found: C, 71.89; H, 6.97; N, 4.28.

Example 11

General alkylation procedure for compounds 6-8, 10-12a, 14, and 16: A mixture of alkylating agent (1 equiv), THIQ (1.1 equiv) $K_2CO_3$ (1.1 equiv), and KI (catalytic) in DME (10 mL) was placed in a 20 mL microwave vial with a stirrer and tightly sealed. The mixture was subjected to microwave heating at 120° C. for 60 min. The mixture was directly purified on silica by flash chromatography (gradient up to 70% EtOAc in hexanes) to afford compound 7 (FIG. 4). The free base where necessary, was converted to the HCl salt and crystallized out of a MeOH-$Et_2$O solvent mixture.

Example 12

2-(4-(4-Fluorophenyl)butyl)-1,2,3,4-tetrahydroisoquinoline hydrochloride, 6 (FIG. 4): The synthesis of 1-(4-chlorobutyl)-4-fluorobenzene 4a (FIG. 4) was previously reported (Peprah et al., (2012) Bioorg. Med. Chem. 20: 1671) and following the procedure described in Example 11, 4a (FIG. 4) was reacted with THIQ to afford compound 6 (FIG. 4) as its HCl salt form. Yield: 75%, mp: 205-206° C. $^1$H NMR (DMSO-$d_6$): d 7.30-7.06 (6H, m); 6.99-6.92 (2H, m); 4.60-4.55 (1H, m); 4.01-3.94 (1H, m), 3.65-3.59 (1H, m), 3.51-3.42 (1H, m), 3.27-3.17 (1H, m), 3.07-2.93 (4H, m), 2.66 (2H, t, J=7.5); 2.08-1.96 (2H, m), 1.75-1.63 (2H, m). Calculated for $C_{19}H_{23}ClFN.0.2H_2O$: C, 70.55; H, 7.17; N, 4.33; Found: C, 70.73; H, 7.36; N, 4.45.

Example 13

2-(3-(4-Fluorophenoxy)propyl)-1,2,3,4-tetrahydroisoquinoline hydrochloride, 7 (FIG. 4): Following the general alkylation procedure described in Example 11, previously reported alkylating agent 3-(4-fluorophenoxy)propyl methanesulfonate 4b (FIG. 4) (Peprah et al., (2012) Bioorg. Med. Chem. 20: 1671) was reacted with THIQ to give compound 7 (FIG. 4) as a white crystalline HCl salt. Yield: 30%, mp: 196-197° C. $^1$H NMR (DMSO-$d_6$): d 11.23 (1H, br s), 7.25 (4H, m), 7.15 (2H, m), 6.95 (2H, m), 4.54 (1H, d, J=15.6 Hz), 4.28 (1H, dd, J=8.4, 15.6 Hz), 4.06 (2H, t, J=6.0 Hz), 3.69 (1H, m), 3.24 (2H, m), 3.34 (2H, m), 3.00 (1H, m), 2.28 (2H, m). Calculated for $C_{18}H_{21}ClFNO$: C, 67.18; H, 6.58; N, 4.35; Found: C, 67.10; H, 6.55; N, 4.38.

Example 14

3-((4-Fluorophenyl)thio)propyl 4-methylbenzenesulfonate, 4c (FIG. 4): To a solution of 3-(4-fluorophenylthio)propan-1-ol (Peprah et al., (2012) Bioorg. Med. Chem. 20: 1671) (1 g, 5.4 mmol), $Et_3N$ (2 mL) in $CH_2Cl_2$ (10 mL) was added at room temperature TsCl (1.54 g, 8.1 mmol). The mixture was stirred at room temperature for 12 h, followed by direct purification using column chromatography on silica gel to provide 4c (FIG. 4), 1.72 g, Yield 94%. $^1$H NMR ($CDCl_3$): δ 7.77 (2H, J=8.4 Hz), 7.34 (2H, J=8.4 Hz), 7.30 (2H, dd, J=5.4, 8.4 Hz), 6.97 (2H, J=8.7 Hz), 4.13 (2H, t, J=8.0 Hz), 2.86 (2H, J=7.2 Hz), 1.89 (2H, m).

Example 15

2-(3-((4-Fluorophenyl)thio)propyl)-1,2,3,4-tetrahydroisoquinoline hydrochloride, 8 (FIG. 4): Reacting alkylating agent 4c (FIG. 4) and THIQ under the general alkylation conditions (Example 11) produced compound 8 (FIG. 4) as an HCl salt. Yield: 29%, mp: 172-173° C. $^1$H NMR (DMSO-$d_6$): δ 11.31 (1H, m), 7.44 (2H, m), 7.22 (6H, m), 4.46 (1H, d, J=15.3 Hz), 4.22 (1H, dd, 7.44 (2H, m), 7.22 (6H, m), 4.46 (1H, d, J=15.3 Hz), 4.22 (1H, dd, J=7.5, 15.3 Hz), 3.61 (1H, m), 3.27 (4H, m), 3.04 (2H, t, J=6.0 Hz), 2.95 (1H, m), 2.08 (2H, m). Calculated for $C_{18}H_{21}ClFNS$: C, 63.98; H, 6.26; N, 4.15; Found: C, 63.77; H, 6.27; N, 4.18.

Example 16

2-(3-((4-Fluorophenyl)sulfinyl)propyl)-1,2,3,4-tetrahydroisoquinoline hydrochloride, 9 (FIG. 5): To a solution of 8 (FIG. 4) (0.2 g, 0.59 mmol) in MeOH (5 mL) was added with stirring m-CPBA (0.2 g) at 0° C. After stirring for 1 h. at room temperature, the mixture was diluted with $Et_2$O (10 mL). A solid precipitate was collected by filtration. Further crystallization from MeOH-$Et_2$O gave 0.15 g of 9 as an HCl salt. 73% Yield: 73%, mp: 177-178° C. $^1$H NMR (DMSO-$d_6$): δ 10.53 (1H, br s), 7.74 (2H, dd, J=4.8, 8.4 Hz), 7.45 (2H, t, J=8.7 Hz), 7.22 (4H, m), 4.50 (1H, d, J=15.3 Hz), 4.25 (1H, dd, J=7.5, 15.3 Hz), 3.63 (1H, m), 3.27 (3H, m), 3.14 (2H, m), 3.98 (1H, m), 2.88 (1H, m), 2.15 (1H, m), 2.00 (1H, m). Calculated for $C_{18}H_{21}ClFNOS\cdot 0.3H_2O$: C, 60.17; H, 5.89; N, 3.90; Found: C, 60.09; H, 5.82; H, 3.94.

Example 17

4-(3,4-Dihydroisoquinolin-2(1H)-yl)-1-(4-fluorophenyl) butan-1-one, 10 (FIG. 6): Using 4-chloro-1-(4-fluorophenyl) butan-1-one 6a (FIG. 6) as the alkylating agent, compound 10 (FIG. 6) was obtained as a white solid (free base)

following the general alkylation method (Example 11). Yield: 38%, mp: 104-105° C. $^1$H NMR (CDCl$_3$): 7.96 (2H, dd, J=5.4, 9.0 Hz), 6.98-7.11 (6H, m), 3.61 (2H, m), 3.03 (2H, t, J=7.2 Hz), 2.86 (2H, t, J=6.0 Hz), 2.72 (2H, t, J=6.0 Hz), 2.58 (2H, t, J=6.9 Hz), 2.03 (2H, q, J=6.9 Hz). Calculated for C$_{19}$H$_{20}$FNO: C, 76.74; H, 6.78; N, 4.71; Found: C, 76.51; H, 6.83; N, 4.69.

Example 18

4-(3,4-Dihydroisoquinolin-2(1H)-yl)-1-phenylbutan-1-one, 11 (FIG. 6): Following the general alkylation procedure (Section 4.7), 4-chloro-1-phenylbutan-1-one 6b (FIG. 6) was reacted with THIQ to produce compound 11 (FIG. 6) as its HCl salt to afford a white crystalline solid (1.2 g). Yield: 69%, mp: 185-187° C. $^1$H NMR (DMSO-d$_6$) δ 11.39 (s, 1H), 7.98 (2H, d, J=7.6 Hz), 7.63 (1H, d, J=7.3 Hz), 7.53 (2H, dd, J=7.5 Hz), 7.28-7.17 (4H, m), 4.53 (1H, dd, J=3.1, 15.4 Hz), 4.27 (1H, dd, J=7.7, 15.6 Hz), 3.68 (1H, s), 3.35-3.17 (6H, m), 2.98 (1H, dd, J=3.3, 12.6 Hz), 2.24-2.07 (2H, m). $^{13}$C NMR (75 MHz, DMSO-d$_6$) d 199.18, 136.82, 133.77, 131.96, 129.19, 129.01, 128.95, 128.36, 127.95, 127.09, 127.00, 54.97, 51.91, 48.93, 35.68, 25.19, 18.40. Calculated for C$_{19}$H$_{22}$ClNO: C, 72.25; H, 7.02; N, 4.43; Found: C, 71.97; H, 7.01; N, 4.30.

Example 19

1-(4-Bromophenyl)-4-(3,4-dihydroisoquinolin-2(1H)-yl)butan-1-one hydrochloride, 12a (FIG. 6): Following the procedure in Example 11, the alkylating agent 1-(4-bromophenyl)-4-chlorobutan-1-one 6c (FIG. 6) was reacted with THIQ to obtain 12a (FIG. 6) as its HCl salt. Yield: 54%, mp: 211-212° C. $^1$H NMR (DMSO-d$_6$) d 11.44 (1H, s), 7.90 (2H, dd, J=8.5, 1.9 Hz), 7.73 (2H, dd, J=8.5, 1.9 Hz), 7.29-7.16 (4H, m), 4.51 (1H, d, J=15.5 Hz), 4.34-4.19 (1H, m), 3.69-3.62 (1H, m), 3.36-3.19 (6H, m), 2.97 (1H, d, J=13.1 Hz), 2.13 (2H, q, J=7.5 Hz). $^{13}$C NMR (75 MHz, DMSO-d$_6$) δ 198.43, 135.84, 132.23, 131.96, 130.38, 128.99, 128.93, 127.94, 127.81, 127.07, 126.99, 54.90, 51.90, 48.92, 35.74, 25.17, 18.32. Calculated for C$_{19}$H$_{21}$BrClNO: C, 57.81; H, 5.36; N, 3.55; Found: C, 57.67; H, 5.29; N, 3.65.

Example 20

4-(4-(3,4-Dihydroisoquinolin-2(1H)-yl)butanoyl)benzonitrile, 12 (FIG. 6): To a 25 mL flask equipped with a stirrer was added 12a (FIG. 6) (0.79 g, 2.6 mmol) in its free base form, dimethylacetamide (DMAC) (15 mL), K$_4$[Fe(CN)$_6$].3H$_2$O (0.93 g, 2.2 mmol); Na$_2$CO$_3$ (0.23 g, 2.2 mmol), KI (73.0 mg, 20 mol %), and Pd(OAc)$_2$ (0.4 mol %). The flask was evacuated and filled with N$_2$ and heated to 120° C. for 12 h. Reaction conversion was monitored by TLC. Upon completion, the reaction mixture was cooled to rt, 5% NH$_4$OH (20 mL) was added, extracted with 3×20 mL of EtOAc, the pool of organic layers was washed with brine (20 mL), dried over Na$_2$SO$_4$ and the filtrate was concentrated in vacuo. The crude was purified on silica by flash chromatography (Hexanes/EtOAc gradient up to 80% EtOAc) to afford 12 (FIG. 6) which was converted to the HCl salt (0.508 g) as white crystals. Yield: 68%, mp: 199-200° C. $^1$H NMR (DMSO-d$_6$) δ 11.11 (1H, s), 8.12 (2H, dd, J=1.8, 8.5 Hz), 8.03 (2H, dd, J=2.1, 8.5 Hz), 7.31-7.16 (4H, m), 4.55 (1H, dd, J=3.2, 14.7 Hz), 4.28 (1H, dd, J=7.7, 15.5 Hz), 3.70 (1H, d, J=9.7 Hz), 3.36-3.21 (6H, m), 3.02 (1H, d, J=3.6 Hz), 2.15 (2H, q, J=6.9, 7.9 Hz). $^{13}$C NMR (75 MHz, DMSO-d$_6$) d 198.70, 140.17, 134.68, 134.28, 132.29, 128.58, 128.38, 126.52, 126.13, 125.56, 118.10, 115.77, 57.15, 55.93, 50.81, 36.51, 28.96, 22.03. Calculated for C$_{20}$H$_{21}$ClN$_2$O: C, 70.48; H, 6.21; N, 8.22. Found: C, 70.30; H, 6.36; N, 8.15.

Example 21

4-(4-(3,4-Dihydroisoquinolin-2(1H)-yl)butanoyl)benzamide, 13 (FIG. 6): A mixture of 12 (FIG. 6) (0.3 g, 1 mmol) and KOH (0.22 g, 4 mmol) in t-BuOH (10 mL) was refluxed for 12 h. The reaction was allowed to cool to room temperature and extracted with EtOAc (15 mL×2). The organic layers were pooled and washed with brine (20 mL), dried over Na$_2$SO$_4$, filtered, and the filtrate reduced in vacuo. The crude was purified by flash chromatography (Hexanes/EtOAc gradient up to 80% EtOAc) to obtain 13 (FIG. 6) (0.40 g) as white crystals. Yield: 46%, mp: 177-178° C. $^1$H NMR (DMSO-d$_6$) δ 8.11 (1H, s), 7.97 (2H, dd, J=2.5, 8.8 Hz), 7.92 (2H, dd, J=2.5, 8.8 Hz), 7.54 (1H, s), 7.10-6.95 (4H, m), 3.48 (2H, s), 3.06 (2H, t, J=7.0 Hz), 2.71 (2H, t, J=5.8 Hz), 2.59 (2H, t, J=5.8 Hz), 2.48 (2H, t, J=7.1 Hz), 1.86 (2H, q, J=7.1 Hz). $^{13}$C NMR (75 MHz, DMSO-d6) d 200.07, 167.50, 139.17, 138.25, 135.30, 134.61, 128.75, 128.17, 128.15, 126.80, 126.28, 125.80, 57.32, 55.86, 50.85, 36.46, 29.06, 21.79. Calculated for C$_{20}$H$_{22}$N$_2$O$_2$: C, 74.51; H, 6.88; N, 8.69. Found: C, 74.59; H, 6.70; N, 8.58.

Example 22

4-(3,4-Dihydroisoquinolin-2(1H)-yl)-1-(4-methoxyphenyl)butan-1-one hydrochloride, 14 (FIG. 6): Following the alkylation procedure described in Example 11 above and using 4-chloro-1-(4-methoxyphenyl)butan-1-one 6d (FIG. 6) as the alkylating agent, compound 14 (FIG. 6) was obtained as the HCl salt. Yield: 60%, mp: 194-195° C. $^1$H NMR (DMSO-d$_6$) δ 11.57 (1H, s), 7.97 (2H, dd, J=2.1, 8.8 Hz), 7.31-7.19 (4H, m), 7.05 (2H, dd, J=2.0, 8.7 Hz), 4.53 (1H, d, J=15.5 Hz), 4.29 (1H, d, J=11.1 Hz), 3.84 (3H, s), 3.67 (1H, s), 3.35-3.11 (6H, m), 2.99 (1H, d, J=12.7 Hz), 2.16 (2H, q, J=7.9 Hz). $^{13}$C NMR (75 MHz, DMSO-d$_6$) d 197.55, 163.63, 132.01, 130.69, 129.83, 129.03, 128.94, 127.95, 127.10, 127.00, 114.35, 56.04, 55.06, 51.89, 48.89, 35.32, 25.19, 18.56. Calculated for C$_{20}$H$_{24}$ClNO$_2$: C, 69.45; H, 6.99; N, 4.05. Found: C, 69.28; H, 6.87; N, 4.09.

Example 23

4-(3,4-Dihydroisoquinolin-2(1H)-yl)-1-(4-hydroxyphenyl)butan-1-one hydrochloride, 15 (FIG. 6): To a dry microwave vial equipped with a stirrer and charged with NaI (0.17 g, 1.10 mmol) in HBr solution (48% aq, 10 mL) was added compound 14 (FIG. 6) in its free base form (0.31 g, 1.0 mmol). The mixture was subjected to microwave heating at 110° C. for 30 min. The reaction vial was allowed to cool to room temperature (rt) and the mixture directly purified using flash column chromatography (gradient elution up to 80% EtOAc in hexane). The product obtained was converted to its HCl salt to obtain compound 15 (FIG. 6) as a white flaky solid (0.21 g). Yield: 63%, mp: 218-219° C. $^1$H NMR (DMSO-d$_6$) δ 11.13 (1H, s), 10.51 (1H, s), 7.84 (2H, d, J=8.0 Hz), 7.33-7.15 (4H, m), 6.87 (2H, d, J=7.9 Hz), 4.48 (1H, s), 4.28 (1H, s), 3.66 (1H, s), 3.35-2.93 (7H, m), 2.11 (2H, t, J=7.8 Hz). $^{13}$C NMR (75 MHz, DMSO-d$_6$) d 197.24, 162.69, 131.95, 130.85, 128.94, 128.40, 127.98, 127.09, 127.01, 115.69, 55.20, 52.14, 49.06, 35.00, 25.28, 18.74.

Calculated. for $C_{19}H_{22}ClNO_2 \cdot 0.75H_2O$; C, 66.08; H, 6.86; N, 4.06; Found: C, 66.17; H, 6.49; N, 4.03.

Example 24

1-(4-Chlorophenyl)-4-(3,4-dihydroisoquinolin-2(1H)-yl) butan-1-one hydrochloride, 16 (FIG. 6): THIQ was alkylated with 4-chloro-1-(4-chlorophenyl)butan-1-one 6e (FIG. 6) and the product converted to its HCl salt to afford compound 16 (FIG. 6) as its HCl salt. Yield: 61%, mp: 209-210° C. $^1$H NMR (DMSO-$d_6$): δ 11.00 (br s, 1H), 7.97 (2H, d, J=9.0 Hz), 7.62 (2H, d, J=9.0 Hz), 7.27-7.18 (4H, m), 5.4 (1H, d, J=14.4 Hz), 4.31-4.23 (1H, m), 3.74-3.64 (1H, m), 3.50-3.38 (2H, m), 3.36-3.25 (4H, m), 3.08-2.90 (1H, m), 2.17-2.10 (2H, m). $^{13}$C NMR (75 MHz, DMSO-d6): d 198.25, 138.62, 135.55, 131.96, 130.29, 129.29, 128.97, 128.94, 127.97, 127.08, 127.08, 127.01, 54.93, 51.94, 48.95, 35.75, 25.17, 18.34. Calculated. $C_{19}H_{21}Cl_2NO$; C, 65.15; H, 6.04; N, 4.00; Found: C, 65.03; H, 6.16; N, 3.99.

Example 25

General alkylation procedure A: A mixture of alkylating agent (1 equiv), appropriate amine (1.1 equiv) $K_2CO_3$ (1.1 equiv), and KI (catalytic) in DME or $CH_3CN$ (10 mL) was placed in a 20 mL microwave vial (for MW) with a stirrer and tightly sealed. The mixture was subjected to microwave (MW) heating at 120° C. for 60 min. The resulting crude mixture was directly purified on silica gel by flash chromatography (gradient up to 70% EtOAc in hexanes) to afford the final compounds. The free base where necessary, was converted to the HCl or HBr salt and crystallized out of a mixture of MeOH-$Et_2O$.

Example 26

General alkylation procedure B: A mixture of alkylating agent (1 equiv), appropriate amine (1.1 equiv) $K_2CO_3$ (1.1 equiv), and KI (catalytic) in DME or $CH_3CN$ (50 mL) was placed in a round bottomed flask with a stirrer was heated to reflux on a heating plate for 24-28 h. The reaction was monitored by TLC for product formation. After reaction was complete, the resulting crude mixture was directly purified on silica gel by flash chromatography (gradient up to 70% EtOAc in hexanes) to afford the final compounds. The free base where necessary, was converted to the HCl or HBr salt and crystallized out of a mixture of MeOH-$Et_2O$.

Example 27

2-(3-(3,4-dihydroisoquinolin-2(1H)-yl)propyl)benzo[d] thiazole hydrobromide, 1b (FIG. 11): Previously reported alkylating agent 2-(3-chloropropyl)benzo[d]thiazole[18] was reacted with THIQ under the general alkylation conditions B to produce the hygroscopic compound 1b (FIG. 11) as the HBr salt in 20% yield. $^1$H NMR (DMSO-$d_6$): 9.96 (br s, 1H), 8.08 (d, J=7.5 Hz, 1H), 7.93 (d, J=7.5 Hz, 1H), 7.50 (t, J=7.5 Hz, 1H), 7.42 (t, J=7.5 Hz, 1H), 7.20-7.30 (m, 4H), 4.61 (d, J=13.8 Hz, 1H), 4.34 (dd, J=7.8, 15.6 Hz, 1H), 3.74-3.79 (m, 1H), 3.34-3.42 (m, 3H), 3.23-3.28 (m, 2H), 3.02-3.18 (m, 2H), 2.30-2.40 (m, 2H). Anal. Calculated for $C_{19}H_{22}Br_2N_2S$: C, 48.53; H, 4.72; N, 5.96. Found: C, 48.61; H, 4.72; N, 5.89.

Example 28

2-(3-Chloro-propyl)-1H-benzoimidazole, D (FIG. 11): To a mixture of 1,2-diaminobenzene,4 (FIG. 10) (0.5 g, 4.6 mmol) and 4-chlorobutanoic acid, 5 (FIG. 10) (0.86 g, 7 mmol) in a schlenk tube was added 5N HCl solution (25 mL) and heated to boil for 5 h. The reaction mixture was then cooled and added to water (25 mL). The precipitate obtained was filtered and vacuum dried to give a white solid (1.25 g, 56%) which was used in the next step without further purification.

Example 29

2-(3-(1H-benzo[d]imidazol-2-yl)propyl)-1,2,3,4-tetrahydroisoquinoline, 1d (FIG. 11): A mixture of 2-(3-chloropropyl)-1H-benzoimidazole, D (FIG. 11), (1.2 g, 6.15 mmol), THIQ (1.2 g, 9.0 mmol), KI (100 mg) and $Et_3N$ (4 mL, 28.5 mmol) in DMF (5 mL) was stirred for 56 h at room temperature (rt). The mixture was diluted with EtOAc (200 mL), washed with brine (3×50 mL). The organic layer was dried over $Na_2SO_4$, and filtered. The filtrate was concentrated in vacuo to dry and followed by column chromatography on silica gel to afford 2-[3-(1Hbenzoimidazol-2-yl)-propyl]-1,2,3,4-tetrahydro-isoquinoline, 1d (FIG. 11) as the HCl salt (0.32 g, 14%) and crystallized from MeOH-$Et_2O$ mixture. Mp: 234-235° C.; 1H NMR (DMSO-$d_6$): 7.77 (m, 2H), 7.50 (m, 2H), 7.22 (m, 4H), 4.45 (br s, 2H), 3.52 (br s, 2H), 3.34 (m, 4H), 3.15 (br s, 2H), 2.52 (m, 2H). Anal. Calculated for $C_{19}H_{23}Cl_2N_3 \cdot 0.3H_2O$: C, 61.72; H, 6.27; N, 11.37. Found: C, 61.40; H, 6.48; N, 11.35.

Example 30

2-(4-(8-Chloro-3,4-dihydroisoquinolin-2(1H)-yl)butyl) benzo[d]thiazole hydrochloride, 1e (FIG. 11): Using the previously reported alkylating agent 2-(4-chlorobutyl)-benzo[d]thiazole (Zhu et al., (2012) *Eur. J. Med. Chem.* 53: 124), the amine 8-chloro-1,2,3,4-tetrahydroisoquinoline was N-alkylated under the general alkylation reaction condition B, described above to produce compound 1e as a white HCl salt in 45% yield. Mp: 192-194° C. $^1$H NMR (300 MHz, DMSO-$d_6$): δ 11.01 (br s, 1H), 8.19 (d, J=7.8 Hz, 1H), 8.07 (d, J=7.8 Hz, 1H), 7.62-7.54 (m, 3H), 7.45 (t, J=6.9 Hz, 1H), 7.35 (d, J=7.8 Hz, 1H), 5.05-4.95 (m, 1H), 4.69 (d, J=1.5 Hz, 1H), 4.47-4.40 (m, 1H), 3.89-3.85 (m, 1H), 3.48-3.32 (m, 4H), 3.22 (t, J=5.1 Hz, 2H), 2.05 (s, 4H). Anal. Calculated for; $C_{20}H_{22}Cl_2N_2S \cdot 0.9.H_2O$: C, 58.65, H; 5.41, N; 6.84, Found; C; 58.43, H; 5.81, N; 6.36.

Example 31

Alkylating agent, 5-Chloro-2-(4-chlorobutyl)benzo[d]thiazole, C (FIG. 10): Using similar cyclization reaction procedure previously described (Zhu et al., (2012) *Eur. J. Med. Chem.* 53: 124), 2-amino-4-chlorobenzenethiol was reacted with 5-chloropentanoyl chloride in toluene at rt to afford alkylating agent C (FIG. 11). $^1$H NMR (300 MHz, CDCl$_3$): δ 7.85 (d, J=2.1 Hz, 1H), 7.75 (d, J=8.1 Hz, 1H), 7.34 (dd, J=1.8 Hz, 6.6 Hz, 1H), 3.59 (t, J=6.6 Hz, 2H), 3.15 (t, J=7.2 Hz, 2H), 2.08-2.01 (m, 2H), 1.96-1.89 (m, 2H).

Example 32

5-Chloro-2-(4-(3,4-dihydroisoquinolin-2(1H)-yl)butyl) benzo[d]thiazole hydrochloride, 1f (FIG. 11): Alkylating agent C (FIG. 10) was reacted with THIQ under the general alkylation condition B described above to afford compound 1f (FIG. 11) as the HCl salt in 75% yield. Mp: 229-231° C., $^1$H NMR (300 MHz, DMSO-$d_6$): δ 10.68 (s, 1H), 8.10 (d, J=8.4 Hz, 1H), 8.00 (d, J=1.5 Hz, 1H), 7.47-7.44 (dd, J=2.1, 8.4 Hz, 1H), 7.27-7.17 (m, 4H), 4.52-4.47 9d, J=15.6 Hz, 1H), 4.28-4.21 (dd, J=7.8, 15.3 Hz, 1H), 3.70-3.64 (m, 1H), 3.37 (s, 2H), 3.24-3.16 (m, 4H), 3.02-2.97 (m, 1H), 1.96-1.89 (m, 4H). Anal. Calculated for $C_{20}H_{22}Cl_2N_2S$: C, 61.07; H, 5.64; N, 7.12. Found: C, 60.89; H, 5.65; N, 6.94.

Example 33

5-Chloro-2-(4-(5-chloro-3,4-dihydroisoquinolin-2(1H)-yl)butyl)benzo[d]thiazole hydrochloride, 1g (FIG. 11): Using method B of the general alkylation reaction condition, 8chloro-1,2,3,4-tetrahydroisoquinoline was N-alkylated with alkylating agent C (FIG. 10) to afford compound 1g (FIG. 11) as a white solid HCl salt in 73% yield. Mp: 218-220° C., $^1$H NMR (300 MHz, DMSO-$d_6$): δ 11.70 (br s, 1H), 8.08 (d, J=8.7 Hz, 1H,), 7.99 (d, J=2.1 Hz, 1H), 7.47-7.42, (m, 2H), 7.30 (t, J=7.8 Hz, 1H), 7.19 (d, J=7.8 Hz, 1H), 4.55-4.5 (m, 1H), 4.32-4.24 (m, 1H), 4.02-3.97 (m, 2H), 3.36-3.18 (m, 4H), 3.06 (t, J=5.1 Hz, 2H), 1.89 (s, 4H). Anal. Calculated for $C_{20}H_{21}Cl_3N_2S.0.24.H_2O$: C, 55.58; H, 4.90; N, 6.48. Found: C, 55.57; H, 5.10; N, 6.19.

Example 34

5-Chloro-2-(4-(octahydroisoquinolin-2(1H)-yl)butyl) benzo[d]thiazole hydrochloride, 1h (FIG. 11): General alkylation method B was used. Alkylating agent C (FIG. 10) was reacted with decahydroisoquinoline to afford compound 1h (FIG. 11) in 85% yield. Mp: 141-143° C. $^1$H NMR (300 MHz, DMSO-$d_6$): δ (9.93 (s, 1H), 8.11-8.08 (d, J=8.4 Hz, 1H), 8.00 (d, J=1.8 Hz, 1H), 7.47-7.44 (dd, J=2.1, 11.4 Hz, 1H) 3.50-3.30 (m, 4H), 3.25 (d, J=10.2 Hz 1H), 3.18-3.13 (t, J=7.2 Hz, 2H), 3.06-3.300 (m, 2H), 2.90-2.80 (m, 1H), 1.86-1.78 (m, 4H), 1.70-1.66 (m, 2H), 1.60-1.43 (m, 4H), 1.24-1.18 (t, J=10.2 Hz, 2H), 1.00-0.87 (t, J=12.0 Hz, 2H). Anal. Calculated for $C_{20}H_{28}Cl_2N_2S.0.95.H_2O$: C, 57.67; H, 6.78; N, 6.73. Found: C, 57.66; H, 7.08; N, 6.51.

Example 35

5-Chloro-2-(4-(6,7-dimethoxy-3,4-dihydroisoquinolin-2(1H)-yl)butyl)benzo[d]thiazole hydrochloride, 1i (FIG. 11): Compound 1i (FIG. 11) in its HCl salt form was prepared similarly to 1h (FIG. 11) above using 6,7-dimethoxy-1,2,3,4-tetrahydroisoquinoline as the amine in a 79% yield. Mp: 180-182° C., $^1$H NMR (300 MHz, DMSO-$d_6$): δ 10.60 (s, 1H), 8.09 (d, J=9.0 Hz, 1H), 8.00 (d, J=1.8 Hz, 1H), 7.47-7.44 (dd, J=2.1, 8.4 Hz, 1H), 6.78 (d, J=8.4 Hz, 2H), 3.80-3.74 (m, 5H), 3.30-3.16 (m, 5H), 1.90-1.86 (m, 4H). Anal. Calculated for $C_{20}H_{28}Cl_2N_2S.0.32EtOAc$: C, 54.91; H, 5.45; N, 5.82. Found: C, 54.76; H, 5.84; N, 5.54.

Example 36

(E)-2-(1-Oxo-1H-inden-2(3H)-ylidene)acetic acid, 8 (FIG. 12): A mixture of 1-indanone, 6 (FIG. 12) (3 g, 22.7 mmol), glyoxylic acid (50% aqueous solution, 5.9 g, 54.5 mmol), and conc. $H_2SO_4$ (0.74 mL) in dioxane (5 mL) were stirred at refluxing temperature for 12 h. The mixture was cooled, the product filtered off, washed with water and dried to give the acid (E)-2-(1-oxo-1H- inden-2(3H)-ylidene) acetic acid 8 (FIG. 12) (3.68 g, 86.2%) as a white solid. Mp: 202-204° C. (lit. mp 205-206° C.), $^1$H NMR (300 MHz, DMSO-$d_6$): δ 12.00 (br s, 1H), 7.73-7.80 (m, 2H), 7.68 (d, J=7.7 Hz, 1H), 7.49 (t, J=7.9 Hz, 1H), 6.55 (t, J=2.4 Hz, 1H), 4.08 (d, J=1.8, 2H).

Example 37

(E)-2-(1-Oxo-3,4-dihydronaphthalen-2(1H)-ylidene)acetic acid, 9 (FIG. 12): Intermediate 9 (FIG. 12) was prepared similarly to 8 (FIG. 12) above using a-tetra-lone instead of 1-indanone (Scheme 3, FIG. 12). The crude product obtained after filtration was used for the next step without further purification. Yield (3.5 g, 84%). $^1$H NMR (300 MHz, DMSO-$d_6$): 12.96 (br s, 1H), 7.95-7.92 (m, 1H), 7.83-7.57 (m, 1H), 7.43-7.38 (m, 2H), 6.65-6.64 (m, 1H), 3.31-3.27 (m, 2H), 2.98 (t, J=6.6 Hz, 2H).

Example 38

2-(1-Oxo-2,3-dihydro-1H-inden-2-yl)acetic acid, 10 (FIG. 12): (E)-2-(1-Oxo-1H-inden-2(3H)-ylidene) acetic acid, 8 (FIG. 12) (10 g, 53 mmol) in MeOH (45 mL) and dioxane (150 mL) with Pd/C (10%, 1 g) was stirred under $H_2$ (40 psi) for 48 h. The mixture was filtered through celite and the solvent evaporated to give 2(1-oxo-2,3-dihydro-1H-inden-2-yl)acetic acid 7 (FIG. 12) as an off-white solid. Mp 85-88° C., $^1$H NMR (300 MHz, DMSO-$d_6$): δ 8.47 (br s, 1H, enol OH), 7.08-7.18 (m, 4H, H-4, H-5, H-6, H-7), 2.99-3.06 (m, 2H, H-1, H-3), 2.69-2.74 (m, 1H, H-2), 2.53-2.60 (m, 2H, H-1, H-3), 2.48 (d, J=7.4 Hz, 2H, $CH_2CO_2$).

Example 39

2-(1-Hydroxy-3,4-dihydronaphthalen-2-yl)acetic acid, 11 (FIG. 12): Intermediate 11 (FIG. 12) was prepared similarly to 10 (FIG. 12) above using (E)-2(1-oxo-3,4-dihydronaphthalen-2(1H)-ylidene)acetic acid 9 (FIG. 12) as the precursor (FIG. 12). $^1$H NMR (300 MHz, DMSO-$d_6$): δ 12.13 (br s, 1H), 7.85 (d, J=8.1 Hz, 1H), 7.56-7.5 (m, 1H), 7.35-7.31 (m, 2H), 3.13-3.02 (m, 1H), 2.95 (m, 2H), 2.74-2.66 (m, 1H), 2.44-2.37 (m, 1H), 2.17-2.09 (m, 1H), 2.0-1.85 (m, 1H).

Example 40

2-(2-Hydroxyethyl)-2,3-dihydro-1H-inden-1-ol, 12 (FIG. 12): A solution of 2-(3-Hydroxy-1H-inden-2-yl)acetic acid (3.4 g, 19.8 mmol) in dry THF (100 mL) was added dropwise to a suspension of $LiAlH_4$ (1.5 g, 39.6 mmol) in dry THF (50 mL) at 0° C. and the resulting mixture was stirred at refluxing temperature for 12 h. EtOAc was added to quench excess $LiAlH_4$ and then aqueous HCl solution (10%, 50 mL) was added and the organic fraction separated. The aqueous solution was extracted with EtOAc (3×50 mL), and the combined organic fraction dried and the solvent evaporated to give alcohol 2-(2-hydroxyethyl)-2,3-dihydro-1H-inden-1-ol 12 (FIG. 12) (2.18 g) as a yellow oil which was used for the next step without further purification. $^1$H NMR (300 MHz, CDCl$_3$): δ 7.43-7.35 (m, 1H), 7.26-7.18 (m, 3H), 4.9 (br d, J=6.6 Hz, 1H), 3.91-3.73 (m, 2H), 3.4 (s, 1H), 3.1-2.92 (m, 1H), 2.6-2.46 (m, 1H), 2.29-2.2 (m, 1H), 1.95-1.86 (m, 2H).

Example 41

2-(2-hydroxyethyl)-1,2,3,4-tetrahydronaphthalen-1-ol, 13 (FIG. 12): Synthesis of intermediate 13 (FIG. 12) followed the same procedure as 12 (FIG. 12) above and was used for the next step without further purification.

Example 42

2-(2-Iodoethyl)-1H-indene, 14 (FIG. 12): A solution of triphenylphosphine (5.28 g, 20.2 mmol) and imidazole (1.37 gm, 20.2 mmol) in CH$_2$Cl$_2$ was cooled to 0° C., and iodine (5.09 g, 20.15 mmol) was added. The mixture was stirred for 30 min and then a CH$_2$Cl$_2$ solution (20 mL) of the crude 2-(2hydroxyethyl)-1H-inden-3-ol, 12 (FIG. 12) (2.18 g, approximately 13.43 mmol) obtained above was added in a dropwise manner. The reaction mixture was stirred for 12 h at rt, filtered, the organic layer washed with H$_2$O and then by aqueous sodium thiosulfate (50 mL), H$_2$O 950 mL) and brine 950 mL). The organic layer was dried over sodium sulfate, excess solvent removed under reduced pressure and the residue purified on combiflash column using EtOAc/hexane (1:9) as eluent to afford 2-(2-iodoethyl)-1H-indene 14 (FIG. 12) as a brown solid. $^1$H NMR (300 MHz, CDCl$_3$): δ 7.4 (d, J=7.5 Hz, 1H), 7.32 (d, J=7.5 Hz, 1H), 7.26-7.21 (m, 1H), 7.17-7.11 (m, 1H), 6.62 (s, 1H), 3.4-3.35 (m, 4H), 3.11-3.07 (m, 2H)

Example 43

3-(2-Iodoethyl)-1,2-dihydronaphthalene, 15 (FIG. 12): Under the same Appel reaction conditions described for 14 (FIG. 12) above, the alkylating agent 15 (FIG. 12) was prepared in 26% yield using 2-(2-hydroxyethyl)-1,2,3,4-tetrahydronaphthalen-1-ol, 13 (FIG. 12) as the precursor. $^1$H NMR (300 MHz, CDCl$_3$): δ 7.15-7.1 (m, 3H), 7.03-7.0 (m, 1H), 6.28 (s, 1H), 3.31 (t, J=7.8 Hz, 2H), 2.86-2.75 (m, 4H), 2.27 (t, J=8.4, 2H).

Example 44

2-(2-(1H-inden-2-yl)ethyl)-1,2,3,4-tetrahydroisoquinoline, 2a (FIG. 12): Using method B, the alkylating agent 2-(2-iodoethyl)-1H-indene 11 (FIG. 12) was used to alkylate THIQ to afford compound 2a (FIG. 12) as a white solid in 29% yield. Mp: 87-89° C., $^1$H NMR (300 MHz, CDCl$_3$): δ 7.38 (d, 1H, J=7.2 Hz), 7.29-7.19 (m, 2H), 7.15-7.02 (m, 5H), 6.59 (s, 1H), 3.74 (s, 2H), 3.38 (s, 2H), 2.95 (t, J=6.0 Hz, 2H), 2.83 (s, 6H). Anal. Calculated for C$_{20}$H$_{21}$N: C, 87.23; H, 7.69; N, 5.09; Found: C, 86.97; H, 7.74; N, 4.99.

Example 45

2-(2-(3,4-dihydronaphthalen-2-yl)ethyl)-1,2,3,4-tetrahydroisoquinoline, 2b (FIG. 12): Using the alkylating agent 12 (FIG. 12), THIQ was alkylated under the general alkylation method B to produce compound 2b (FIG. 12) as a hygroscopic solid in 35% yield, $^1$H NMR (300 MHz, CDCl$_3$): δ 7.18-6.96 (m, 8H), 6.29 (s, 1H), 3.7 (s, 2H), 2.93 (t, J=6 Hz, 2H), 2.86-2.77 (m, 4H), 2.76-2.68 (m, 2H), 2.51 (t, J=8.7 Hz, 2H), 2.31 (t, J=8.1 Hz, 2H). $^{13}$C NMR (75 MHz, CDCl$_3$): δ 140.18, 134.74, 134.39, 134.23, 128.66, 127.18, 126.6, 126.42, 126.2, 126.12, 125.6, 125.38, 123.4, 56.92, 56.16, 51.02, 35.41, 29.14, 28.15, 27.58. Anal. Calculated. for C$_{21}$H$_{23}$N: C, 87.15; H, 8.01; N, 4.84; Found: 87.04, 7.96, 4.78.

Example 46

(4-Chlorobut-1-ene-1,1-diyl)bis(chlorobenzene), 19 (FIG. 13): To a solution of 4-chlorobutyryl chloride (5 mL, 44 mmol) in dry THF (50 mL) was added dropwise to a solution of 4-chlorophenyl-magnesium bromide (100 mL, 1.0 M in Et$_2$O, 100 mmol) at −5° C. in 1 h. After addition was complete, the reaction mixture was stirred at rt overnight, and then quenched with saturated NH$_4$Cl solution followed by extraction with EtOAc (400 mL). The organic layer was separated and washed with brine (2×200 mL), then dried with anhydrous Na$_2$SO$_4$ and filtered. The filtrate was concentrated in vacuo, and the residue purified directly on silica gel using flash chromatography to give the pure product, 4,4'-(4-chlorobut-1-ene-1,1-diyl)bis(chlorobenzene) 19 (FIG. 13), 9.3 g, yield 68%. $^1$H NMR (300 MHz, CDCl$_3$): 7.36 (d, J=6.0 Hz, 2H), 7.24 (d, J=6.6 Hz, 2H), 7.12 (d, J=6.0 Hz, 2H), 7.09 (d, J=6.0 Hz, 2H), 6.10 (t, J=7.2 Hz, 1H), 3.57 (t, J=6.6 Hz, 2H), 2.56 (m, 2H).

Example 47

2-(4,4-Bis(4-chlorophenyl)but-3-en-1-yl)-1,2,3,4-tetrahydroisoquinineol hydrobromide, 2c (FIG. 13): Compound 2c (FIG. 13) was prepared by reacting the alkylation agent 4,4'-(4-chlorobut-1-ene-1,1-diyl)bis(chlorobenzene) 19 (FIG. 13) and THIQ under the general alkylation B conditions to afford 2c (FIG. 13) in 56% yield. Mp 215-216° C., $^1$H NMR (DMSO-d6): 9.69 (br s, 1H), 7.51 (d, J=8.1 Hz, 2H), 7.38 (d, J=8.1 Hz, 2H), 7.15-7.28 (m, 8H), 6.18 (t, J=7.5 Hz, 1H), 4.46-4.50 (m, 1H), 4.23-4.31 (m,1H), 3.61-3.66 (m, 1H), 3.30-3.38 (m, 3H), 3.04-3.09 (m, 2H), 2.53-2.58 (m, 2H). Anal. Calculated for C$_{25}$H$_{24}$BrCl$_2$N: C, 61.37; H, 4.94; N, 2.86. Found: C, 61.33; H, 5.05; N, 2.95.

Example 48

1-(4-Bromobutyl)-4,4-dimethylpiperidine-2,6-dione, 21 (FIG. 14): A mixture of 4,4-dimethylpiperidine-2,6-dione, 20 (FIG. 14) (0.93 g, 5 mmol) and 1,4-dibromobutane (5.4 g, 25 mmol) was stirred under reflux in dry CH$_3$CN (20 mL) for 12 h. The reaction mixture was allowed to cool to room temperature and the excess solvent was removed under reduced pressure. The crude product obtained was directly purified on flash column chromatography (silica gel, ethyl acetate/light petroleum 1:3) to afford 1-(4-bromobutyl)-4,4-dimethylpiperidine-2,6-dione 21 (FIG. 14) as a colorless oil which was used in the next stage without further purification. $^1$H NMR (300 MHz, CDCl$_3$): δ 3.8 (t, J=7.2, 2H), 3.42 (t, J=6.6 Hz, 2H), 2.51 (s, 4H), 1.91-1.82 (m, 2H), 1.73-1.62 (m, 2H), 1.08 (s, 6H).

Example 49

1-(4-(3,4-dihydroisoquinolin-2(1H)-yl)butyl)-4,4-dimethylpiperidine-2,6-dione hydrochloride, 2d (FIG. 14): Under the general alkylation method B described above, the alkylating agent 21 (FIG. 14) was reacted with THIQ to afford compound 2d (FIG. 14) as a highly hydroscopic HCl salt in 76% yield. $^1$H NMR (300 MHz, DMSO-d$_6$): δ 9.82 (br s, 1H), 7.66-7.60 (m, 1H), 7.47-7.38 (m, 2H), 7.15 (dd, J=5.4, 10.8 Hz, 1H), 3.59 (t, J=7.4 Hz, 2H), 3.40 (s, 2H), 2.97 (s, 2H), 2.50 (s, 8H), 1.70-1.60 (m, 2H), 1.35 (t, J=7.5 Hz, 2H), 9.95 (s, 6H). Anal. Calculated for C$_{20}$H$_{29}$ClN$_2$O$_2$. 0.15 EtOAc: C; 63.53, H; 7.73, N; 7.41. Found: C; 63.41, H; 8.10, N; 7.02.

Example 50

1-(4-(Isoindolin-2-yl)butyl)-4,4-dimethylpiperidine-2, 6dione, 2e (FIG. 14): Using isoindoline as the amine, compound 2e (FIG. 14) was prepared in its free base form similarly to compound 2d (FIG. 14) above in 23% yield. Mp: 84-85° C., $^1$H NMR (300 MHz, CDCl$_3$): δ 7.18 (s, 4H), 3.83 (s, 4H), 3.81-3.75 (t, J=3.9 Hz, 2H), 2.76-2.71 (t, J=6.9 Hz, 2H), 2.49 (s, 4H), 1.62-1.58 (t, J=7.7 Hz, 4H), 1.06 (s, 6H).

Anal. Calculated for $C_{19}H_{26}N_2O_2 \cdot 0.15\ H_2O$: C, 71.96; H, 8.26; N, 8.83. Found: C, 71.93; H, 8.25; N, 8.81.

Example 51

Synthesis of compounds 3c-3f (FIG. 15): In general, compounds 3c-3f (FIG. 15) were synthesized following the general alkylation method A using the common alkylating agent 4-chloro-1-(4-chlorophenyl)butan-1-one 22 (FIG. 15) to obtain the respective final compounds as HCl salts, except for 3c (FIG. 15), which was obtained as a free base (FIG. 15).

Example 52

1-(4-Chlorophenyl)-4-(3,4-dihydroquinolin-1(2H)-yl) butan-1-one, 3c (FIG. 15): Using 1,2,3,4-tetrahydroquinoline as the amine and 4-chloro-1-(4-chlorophenyl)butan-1-one 22 (FIG. 15) as the alkylating agent, compound 3c (FIG. 15) was produced as a white crystalline solid in 33% yield. Mp: 192-193° C. $^1$H NMR (300 MHz, DMSO-d$_6$) δ 7.97 (d, J=8.3 Hz, 2H), 7.59 (d, J=8.2 Hz, 2H), 7.07-6.91 (m, 2H), 6.85 (d, 1H), 6.66 (d, 1H), 3.38-3.25 (m, 4H), 3.11 (t, J=6.9 Hz, 2H), 2.71 (t, J=6.2 Hz, 2H), 1.97-1.83 (m, 4H). $^{13}$C NMR (75 MHz, DMSO-d$_6$) δ 198.54, 145.25, 139.46, 135.16, 129.44, 129.22, 128.92, 127.15, 122.34, 115.64, 110.65, 50.64, 49.49, 35.66, 28.15, 22.22, 20.87. Anal. Calculated for $C_{19}H_{20}ClNO$: C, 72.72; H, 6.42; N, 4.46. Found: C, 72.48; H, 6.30; N, 4.35.

Example 53

1-(4-Chlorophenyl)-4-(2,3,4,5-tetrahydro-1H-benzo[b] azepin-1-yl)butan-1-one hydrochloride, 3d (FIG. 15): Using 2,3,4,5tetrahydro-1H-benzo[b]azepine as the amine and reacting it with 22 (FIG. 15), compound 3d (FIG. 15) was obtained as a white crystalline HCl salt. Yield: 35%, mp: 192-193° C. $^1$H NMR (300 MHz, Methanol-d$_4$) δ 7.95 (d, J=8.1 Hz, 2H), 7.68 (d, J=7.3 Hz, 1H), 7.54-7.35 (m, 5H), 4.86 (t, J=2.6 Hz, 2H), 4.03-3.44 (m, 4H), 3.32-3.02 (m, 4H), 2.36-1.79 (m, 4H). $^{13}$C NMR (75 MHz, CD$_3$OD) δ 197.63, 139.28, 138.80, 136.67, 134.94, 133.19, 130.46, 129.43, 128.59, 127.72, 123.75, 56.70, 52.39, 34.45, 33.51, 25.45, 23.68, 19.47. Anal. Calculated for $C_{20}H_{23}Cl_2NO$: C, 65.94; H, 6.36; N, 3.84. Found: C, 65.66; H, 6.41; N, 3.74.

Example 54

1-(4-Chlorophenyl)-4-(4,5-dihydro-1H-benzo[c]azepin-2 (3H)-yl)butan-1-one hydrochloride, 3e (FIG. 15): Intermediate 22 (FIG. 15) was used to alkylate the amine 2,3,4,5-tetrahydro-1H-benzo[c]azepine to obtain compound 3e (FIG. 15) as a white solid crystal. Yield: 52%, mp: 201-202° C. $^1$H NMR (300 MHz, DMSO-d$_6$) δ 11.24 (s, 1H), 7.93 (d, J=8.8 Hz, 2H), 7.56 (dd, J=8.5 Hz, 2H), 7.42 (d, J=7.3 Hz, 1H), 7.34-7.21 (m, 3H), 4.56 (d, J=14.1 Hz, 1H), 4.38 (dd, J=5.1, 14.1 Hz, 1H), 3.52-3.42 (m, 2H), 3.35 (s, 2H), 3.12 (td, J=2.4, 6.9 Hz, 2H), 2.88 (t, J=18.8 Hz, 2H), 2.02 (q, J=7.6 Hz, 2H), 1.94-1.84 (m, 2H). $^{13}$C NMR (75 MHz, DMSO-d$_6$) δ 198.15, 143.47, 138.59, 135.44, 132.21, 130.48, 130.25, 129.93, 129.62, 129.24, 127.10, 56.85, 55.95, 35.66, 33.38, 22.40, 18.39. Anal. Calculated for C20H23Cl2NO: C, 65.94; H, 6.36; N, 3.84. Found: C, 65.67; H, 6.44; N, 3.72.

Example 55

1-(4-Chlorophenyl)-4-(4,5-dihydro-1H-benzo[d]azepin-3 (2H)-yl)butan-1-one hydrochloride, 3f (FIG. 15): Amine 2,3,4,5-tetrahydro-1H-benzo[d]azepine was reacted with 22 to produce compound 3f (FIG. 15) as a white solid crystal. Yield: 59%, mp: 240-242° C. $^1$H NMR (300 MHz, DMSO-d$_6$) d 11.31 (s, 1H), 7.98 (dd, J=8.3 Hz, 2H), 7.59 (dd, J=8.4 Hz, 2H), 7.22-7.15 (m, 4H), 3.72-3.59 (m, 2H), 3.53-3.41 (m, 2H), 3.18 (dt, J=6.6, 14.4 Hz, 4H), 2.95 (dt, J=6.8, 16.9 Hz, 4H), 2.09 (q, J=7.6 Hz, 2H). $^{13}$C NMR (75 MHz, DMSO-d$_6$) δ 198.18, 139.80, 138.62, 135.52, 130.28, 129.53, 129.29, 127.40, 56.86, 53.70, 35.87, 31.16, 18.34. Anal. Calculated for $C_{20}H_{23}Cl_2NO$: C, 65.94; H, 6.36; N, 3.84. Found: C, 65.83; H, 6.44; N, 3.90.

Example 56

5-(4-Chlorobutanoyl)indolin-2-one, 24 (FIG. 16): A modified acylation reaction [31] was followed to access intermediate 3b (FIG. 15). Briefly, to a dry 100 mL round-bottomed flask equipped with a stirrer was added 5 g (37.5 mmol) of $AlCl_3$, 30 mL of carbon disulfide ($CS_2$), and 2.5 mL (22.5 mmol) of 4-chlorobutyryl chloride at 0° C. with stirring. To the mixture obtained was added 2 g (15 mmol) of oxindole 23 (FIG. 16) in a portion-wise manner over 20 mins. After the addition was completed, the reaction mixture was allowed to warm to rt and stirred overnight to produce a red precipitate. The content was dumped into a beaker containing 100 g of ice with 5 mL conc. HCl and stirred thoroughly. The brick red precipitate obtained was dissolved in methanol and loaded onto silica column and subsequently separated by combiflash (gradient elution up to 50% EtOAc in hexanes) to afford 2.6 g (73%) of 5-(4-chlorobutanoyl) indolin-2-one, 24 (FIG. 15). $^1$H NMR (300 MHz, DMSO-d$_6$) δ 10.75 (s, 1H), 7.84 (dd, J=1.9, 8.2 Hz, 1H), 7.78 (s, 1H), 6.88 (d, J=8.2 Hz, 1H), 3.68 (t, J=6.7 Hz, 2H), 3.52 (s, 2H), 3.07 (t, J=7.1 Hz, 2H), 2.03 (q, J=6.9 Hz, 2H). $^{13}$C NMR δ 197.83, 177.19, 148.82, 130.53, 129.41, 126.55, 124.52, 109.19, 45.39, 35.95, 35.16, 27.48.

Example 57

5-(4-(3,4-dihydroisoquinolin-2(1H)-yl)butanoyl)indolin-2-one, 3g (FIG. 15): Using the alkylating agent 24 (FIG. 15), THIQ was alkylated under the general alkylation method A condition to afford compound 3g (FIG. 15) as a free base in 59% yield. Mp: 166-168° C. $^1$H NMR (300 MHz, CDCl$^3$) δ 9.23 (s, 1H),7.84 (d, J=4.7 Hz, 1H), 7.87 (d, J=8.2 Hz, 1H), 7.16-6.96 (m, 4H), 6.85 (s, 1H), 3.61 (s, 2H), 3.51 (s, 2H), 3.02 (t, J=7.2 Hz, 2H), 2.86 (t, J=5.9 Hz, 2H), 2.75 (t, J=5.9 Hz, 2H), 2.59 (t, J=7.1 Hz, 2H), 2.04 (q, J=7.2 Hz, 2H). $^{13}$C NMR (75 MHz, CDCl3) δ 199.01, 177.77, 146.77, 134.74, 134.31, 131.90, 129.38, 128.60, 126.55, 126.11, 125.57, 125.34, 124.63, 109.16, 57.34, 55.97, 50.78, 35.97, 35.90, 29.01, 21.92. Anal. Calculated for $C_{21}H_{22}N_2O_2$: C, 75.42; H, 6.63; N, 8.38; Found: C, 75.12; H, 6.74; N, 8.16.

Example 58

Figure 17:
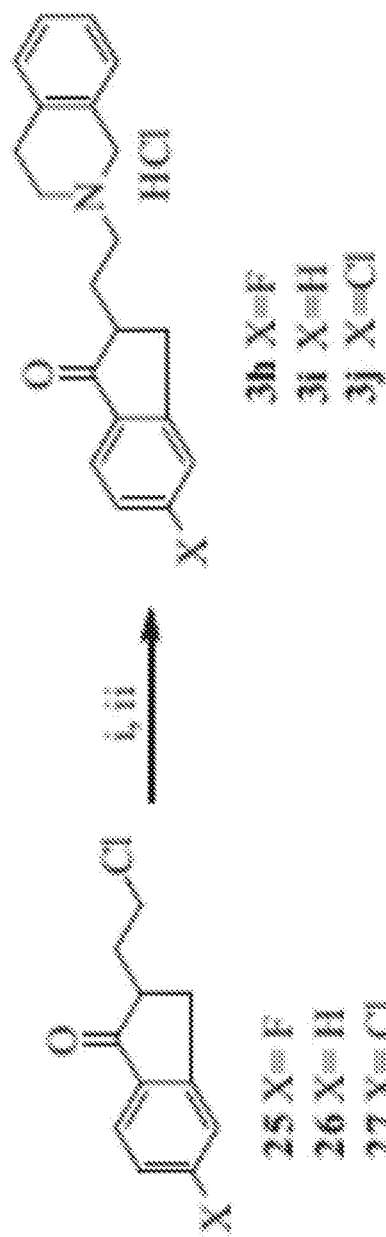
FIG. 17 illustrates scheme 14: Synthesis of indanone analogs of THIQ. Reagents and conditions: (i) THIQ, $K_2CO_3$, KI, toluene, MW (for 3i) or reflux (for 3h and 3j); (ii) ethereal HCl for 3i and 3j.

2-(2-(3,4-dihydroisoquinolin-2(1H)-yl)ethyl)-5-fluoro-2, 3-dihydro-1H-inden-1-one, 3h (FIG. 17); Using the previously reported alkylating agent 2-(2-chloroethyl)-5-fluoro-2,3-dihydro-1H-inden-1-one 25 (FIG. 17). THIQ was alkylated under alkylation method B to afford compound 3h (FIG. 17) in 23% yield. Mp 240-241° C.; $^1$H NMR (DMSO-d$_6$): 7.73 (dd, J=5.8, 8.4 Hz, 1H), 7.45 (d, J=9.0 Hz, 1H), 7.24 (m, 5H), 4.52 (m, 2H), 4.28 (m, 2H), 3.68 (m, 1H), 3.34 (m, 6H), 2.99 (m,1H), 2.89 (m, 2H), 2.31 (m, 1H), 1.99 (m, 1H). Anal. Calculated for $C_{20}H_{21}ClFNO$: C, 69.46; H, 6.12; N, 4.05; Found: C, 69.18; H, 6.08; N, 4.60.

Example 59

2-(2-(3,4-dihydroisoquinolin-2(1H)-yl)ethyl)-2,3-dihydro-1H-inden-1-one hydrochloride, 3i (FIG. 17): Under the general alkylation method B, the previously described alkylating agent 2-(2-chloroethyl)-2,3-dihydro-1H-inden-1-one 26 (FIG. 17) was coupled to THIQ to afford compound 3i (FIG. 17) as the HCl salt in 65% yield. Mp: 201-203° C. $^1$H NMR (300 MHz, DMSO-$d_6$) δ 11.18 (s, 1H), 7.74-7.63 (m, 2H), 7.60 (d, J=7.6 Hz, 1H), 7.48-7.40 (m, 1H), 7.29-7.15 (m, 4H), 4.49 (s, 1H), 4.31 (s, 1H), 3.68 (s, 1H), 3.40 (t, J=8.4 Hz, 3H), 3.01 (s, 1H), 2.92 (d, J=4.1 Hz, 1H), 2.89-2.77 (m, 2H), 2.41-2.28 (m, 1H), 1.99 (d, J=9.8 Hz, 1H). $^{13}$C NMR (75 MHz, DMSO-$d_6$) δ 207.35, 154.03, 136.27, 135.65, 131.92, 128.97, 128.07, 128.00, 127.38, 127.04, 123.76, 53.85, 52.05, 49.10, 44.65, 32.59, 25.42. Anal. Calculated for $C_{20}H_{22}ClNO$ 0.2 $H_2O$: C, 72.47; H, 6.81; N, 4.23. Found: C, 72.55; H, 6.56; N, 4.29.

Example 60

5-Chloro-2-(2-(3,4-dihydroisoquinolin-2(1H)-yl)ethyl)-2,3-dihydro-1H-inden-1-one hydrochloride, 3j (FIG. 17): The previously reported alkylating agent 27 (FIG. 17) was reacted with THIQ under the general alkylation method B condition to afford compound 3j (FIG. 17) as the HCl salt in 41% yield. Mp 239-240° C., $^1$H NMR (DMSO-$d_6$): 11.10 9 (br s, 1H), 7.72 (s,1H), 7.67 (d, J=8.1 Hz, 1H), 7.49 (d, J=8.1 Hz, 1H), 7.17-7.27 (m, 4H), 4.51 (d, J=12.6 Hz, 1H), 4.25-4.32 (m,1H), 3.65-3.2 (m,1H), 3.23-3.42 (m, 5H), 2.92-3.02 (m,1H), 2.86-2.92 (m, 2H), 2.29-2.37 (m,1H), 1.95-2.05 (m,1H). Anal. Calculated for $C_{20}H_{21}Cl_2NO$: C, 66.30; H, 5.84; N, 3.87. Found: C, 66.29; H, 5.94; N, 3.93.

Example 61

Receptor binding studies: Binding affinities reported in Tables 3-5 were conducted by the National Institute of Mental Health Psychoactive Drug Screening Program (NIMH-PDSP). Details of the methods and radioligands used for the binding assays were previously reported (Shapiro et al., (2003) *Neuropsychopharmacol.* 28: 1400).

TABLE 3

Group 1 analogs (FIG. 18) binding affinity constants at clinically relevant CNS receptors

| Compd | $K_i$ (nM) (p$K_i$ ± SEM) | | | | |
|---|---|---|---|---|---|
| | D2 | D3 | D4 | 5-HT$_{1A}$ | 5-HT$_{2A}$ |
| 1a* | 167 | 8.7 | 67.0 | 10.0 | 1681 |
| | (6.78 ± 0.09) | (8.5 ± 0.1) | (7.17 ± 0.05) | (8 ± 0.03) | (5.77 ± 0.06) |
| 1b | MTA | 80.0 | 41.0 | 95.0 | 2051 |
| | | (7.1 ± 0.10) | (7.39 ± 0.04) | (7.02 ± 0.03) | (5.69 ± 0.06) |
| 1c* | 990 | 259 | 141 | 111 | >10,000 |
| | (6 ± 0.04) | (6.59 ± 0.06) | 6.85 ± 0.07 | (6.95 ± 0.07) | |
| 1d | 915.0 | 2176 | 127.0 | 65.0 | >10K |
| | 6.09 ± 0.09 | 5.66 ± 0.07 | 6.9 ± 0.07 | 7.19 ± 0.07 | |
| 1e | 272 | 31.0 | 129 | 29.0 | 258 |
| | (6.57 ± 0.08) | (7.52 ± 0.04) | (6.89 ± 0.08) | (7.53 ± 0.08) | (6.6 ± 0.10) |
| 1f | 138 | 447 | 572 | 15.0 | 702 |
| | (6.86 ± 0.08) | (6.35 ± 0.07) | (6.24 ± 0.09) | (7.84 ± 0.07) | (6.2 ± 0.10) |
| 1g | 853 | 91.0 | 279 | 42.0 | 483 |
| | (6.07 ± 0.08) | (7.04 ± 0.05) | (6.55 ± 0.08) | (7.38 ± 0.08) | (6.3 ± 0.1) |
| 1h | 1087 | 526 | 37.0 | 11.0 | 1144 |
| | (5.96 ± 0.08) | (6.28 ± 0.08) | (7.43 ± 0.06) | (7.93 ± 0.06) | (5.9 ± 0.10) |
| 1i | 418 | 1083 | 272 | 9.9 | 667 |
| | (6.38 ± 0.09) | (5.97 ± 0.07) | (6.57 ± 0.07) | (8 ± 0.05) | (6.2 ± 0.1) |

| | 5-HT$_7$ | 5-HT$_{2B}$ | 5-HT$_{2C}$ | H1 |
|---|---|---|---|---|
| 1a* | 22.0 | 18.0 | 910 | 583 |
| | (7.66 ± 0.06) | (7.74 ± 0.05) | (6.04 ± 0.04) | (6.23 ± 0.08) |
| 1b | 37.0 | 18.0 | 1182 | 822 |
| | (7.43 ± 0.07) | (7.74 ± 0.04) | (5.93 ± 0.05) | (6.09 ± 0.08) |
| 1c* | 211 | 135 | MTA | 762 |
| | (6.68 ± 0.08) | (6.87 ± 0.06) | | (6.12 ± 0.08) |
| 1d | 91.0 | MTA | >10K | 290 ± 40 |
| | 7.04 ± 0.04 | | | |
| 1e | 45.0 | 239 | 675 | 293 |
| | (7.35 ± 0.04) | (6.62 ± 0.06) | (6.17 ± 0.09) | (6.53 ± 0.08) |
| 1f | 25.0 | 16.0 | 759 | 247 |
| | (7.6 ± 0.09) | (7.81 ± 0.07) | (6.12 ± 0.08) | (6.61 ± 0.06) |
| 1g | 144 | 327 | 820 | 560 |
| | (6.84 ± 0.04) | (6.49 ± 0.09) | (6.09 ± 0.09) | (6.25 ± 0.07) |
| 1h | 44.0 | 64.0 | 501 | 268 |
| | (7.36 ± 0.07) | (7.19 ± 0.09) | (6.3 ± 0.07) | (6.57 ± 0.06) |
| 1i | 67.0 | 7.0 | 329 | 327 |
| | (7.17 ± 0.06) | (8.15 ± 0.08) | (6.48 ± 0.08) | (6.49 ± 0.08) |

MTA = Missed 50% of threshold inhibition.
*Binding affinity data from [18].

TABLE 4

Group 2 analogs (FIG. 19) binding affinity constants at clinically relevant CNS receptors

| Compd | $K_i$ (nM) ($pK_i$ ± SEM) | | | | |
|---|---|---|---|---|---|
| | D2 | D3 | D4 | 5-$HT_{1A}$ | 5-$HT_{2A}$ |
| 2a | MTA | 88.0 | 194 | 1,109 | 1,867 |
| | | (7.05 ± 0.09) | (6.71 ± 0.04) | (5.96 ± 0.08) | (5.73 ± 0.04) |
| 2b | 5,647 | 184 | 140 | 138 | 975 |
| | (5.25 ± 0.06) | (6.73 ± 0.04) | (6.85 ± 0.05) | (6.86 ± 0.04) | (6.01 ± 0.09) |
| 2c | MTA | 150 | MTA | MTA | MTA |
| | | (6.8 ± 0.1) | | | |
| 2d | MTA | 1,645 | MTA | MTA | MTA |
| | | (5.8 ± 0.1) | | | |
| 2e | 2,933 | >10,000 | >10,000 | 339 | >10,000 |
| | (5.53 ± 0.09) | | | (6.47 ± 0.07) | |

| | 5-$HT_7$ | 5-$HT_{2B}$ | 5-$HT_{2C}$ | H1 |
|---|---|---|---|---|
| 2a | 132 | 149 | MTA | MTA |
| | (6.88 ± 0.07) | (6.83 ± 0.07) | | |
| 2b | 65.0 | 126 | 2,903 | 1437 |
| | (7.18 ± 0.07) | (6.9 ± 0.04) | (5.54 ± 0.07) | (5.84 ± 0.07) |
| 2c | 497 | MTA | 2,028 | 998 |
| | (6.3 ± 0.07) | | (5.69 ± 0.05) | (6 ± 0.07) |
| 2d | MTA | MTA | MTA | MTA |
| 2e | 739 | 531 | 305 | 3,867 |
| | (8.2 ± 0.1) | (6.28 ± 0.07) | (6.53 ± 0.07) | (5.41 ± 0.07) |

MTA = Missed 50% of threshold inhibition.

TABLE 5

Group 3 analogs (FIG. 20) binding affinity constants at clinically relevant CNS receptors

| Compd | $K_i$ (nM) ($pK_i$ ± SEM) | | | | |
|---|---|---|---|---|---|
| | D2 | D3 | D4 | 5-$HT_{1A}$ | 5-$HT_{2A}$ |
| 3a** | 49.0 ± 3.0 | 72.0 ± 5.0 | 2.3 ± 0.2 | 19.5 | 21.0 |
| 3b** | 126 | 17.0 | 86.0 | 8.2 | MTA |
| | (6.9 ± 0.06) | (7.77 ± 0.04) | (7.07 ± 0.04) | (8.09 ± 0.07) | |
| 3c | MTA | MTA | MTA | MTA | MTA |
| 3d | MTA | MTA | MTA | MTA | MTA |
| 3e | 3,578 | 342 | 442 | 1,712 | 120 |
| | (5.45 ± 0.08) | (6.47 ± 0.04) | (6.35 ± 0.04) | (5.77 ± 0.07) | (6.92 ± 0.03) |
| 3f | 1,170 | 106 | 82 | 214 | 281 |
| | (5.93 ± 0.08) | (6.97 ± 0.04) | (7.09 ± 0.04) | (6.67 ± 0.06) | (6.55 ± 0.03) |
| 3g | 5,399 | 66 | 3,335 | 122 | 1,022 |
| | (5.27 ± 0.09) | (7.18 ± 0.04) | (5.48 ± 0.04) | (6.91 ± 0.07) | (5.99 ± 0.03) |
| 3h | 750 | 223 | 251 | 19.0 | 1,204 |
| | (6.12 ± 0.07) | (6.65 ± 0.04) | (6.6 ± 0.06) | (7.73 ± 0.04) | (5.92 ± 0.09) |
| 3i | 2,583.5 | 866.0 | 1,102 | 48.3 | 391.3 |
| 3j | 946 | 783 | 50 | 16 | 748 |
| | (6.02 ± 0.08) | (6.11 ± 0.07) | (7.3 ± 0.06) | (7.81 ± 0.06) | (6.1 ± 0.1) |
| [a]SB 269970 | ND | ND | ND | <5 | <5 |
| [b]18 | ND | ND | ND | 219 ± 11 | ND |
| [c]3p | ND | ND | ND | 70 ± 12 | ND |

| | 5-$HT_7$ | 5-$HT_{2B}$ | 5-$HT_{2C}$ | H1 |
|---|---|---|---|---|
| 3a** | 381 | 519 | >10,000 | 86.3 ± 7.3 |
| 3b** | 3.6 | 232 | 2,976 | 597 |
| | (8.45 ± 0.07) | (6.63 ± 0.07) | (5.53 ± 0.06) | (6.22 ± 0.05) |
| 3c | MTA | MTA | >10,000 | MTA |
| 3d | MTA | MTA | MTA | MTA |
| 3e | 257 | 501 | 348 | 3,224 |
| | (6.59 ± 0.05) | (6.3 ± 0.05) | (6.46 ± 0.04) | (5.5 ± 0.1) |
| 3f | 138 | 549 | 611 | 1,087 |
| | (6.68 ± 0.05) | (6.26 ± 0.05) | (6.21 ± 0.07) | (6 ± 0.3) |
| 3g | 127 | 483 | 4,234 | MTA |
| | (6.9 ± 0.05) | (6.32 ± 0.05) | (5.37 ± 0.09) | |
| 3h | 1.6 | 294 | MTA | ND |
| | (8.8 ± 0.06) | | | |
| 3i | 265 | 391 | 1,184 | 24 |
| | | | (5.93 ± 0.06) | (7.6 ± 0.1) |

TABLE 5-continued

Group 3 analogs (FIG. 20) binding affinity constants at clinically relevant CNS receptors

| | | | | |
|---|---|---|---|---|
| 3j | 0.5 | 109 | 128 | 553 |
| | (9.33 ± 0.06) | (6.96 ± 0.07) | (6.89 ± 0.08) | (6.26 ± 0.06) |
| [a]SB 269970 | 1.3 | 5 | <5 | ND |
| | 8.9 ± 0.1 | | | |
| [b]18 | 7 ± 2 | ND | ND | ND |
| [c]3p | 4.5 ± 1 | ND | ND | ND |

MTA = Missed 50% of threshold inhibition, ND = Not determined.
*Ki values without the associated SEM, are within 20% of the mean value.
**Binding affinity data from Ofori et al., (2016) *Bioorg. Med. Chem.* 24: 3464
[a]Binding affinity data from Lovell et al., (2000) *J. Med. Chem.* 43: 342
[b]Binding affinity data from Medina et al., (2009) *J. Med. Chem.* 52: 2384
[c]Binding affinity data from Sagnes et al., (2014) *Eur. J. Med. Chem.* 75: 159

Example 62

TABLE 6

Compounds and their binding affinity at clinically relevant CNS receptors $K_i$ (nM) (p$K_i$ ± SEM)

| Compound[a] | D2 | D3 | D4 | 5-HT$_{1A}$ |
|---|---|---|---|---|
| 1** | 2,583.5 | 866.0 | 1,102 | 48.3 |
| 2** | 750 | 223 | 251 | 19.0 |
| | (6.12 ± 0.07) | (6.65 ± 0.04) | (6.6 ± 0.06) | (7.73 ± 0.04) |
| 3** | 946 | 783 | 50 | 16 |
| | (6.02 ± 0.08) | (6.11 ± 0.07) | (7.3 ± 0.06) | (7.81 ± 0.06) |
| 4 | 660 | 289 | 570.5 | 33.0 |
| | (6.18 ± 0.05) | (6.54 ± 0.04) | | (7.48 ± 0.04) |
| 5 | 885 | 476 | 570.5 | 66.0 |
| | (6.05 ± 0.05) | (6.32 ± 0.04) | | (7.18 ± 0.04) |
| 6 | MTA | 78.0 | 67.0 | 64 |
| | | (7.1 ± 0.1) | (7.17 ± 0.04) | (7.19 ± 0.03) |
| 7 | 1,084 | 822.5 | 193.0 | 146.5 |
| | | | | (6.71 ± 0.05) |
| 8 | 2,063 | 299 | 172 | 36.0 |
| | (5.69 ± 0.08) | (6.52 ± 0.08) | (6.77 ± 0.06) | (7.44 ± 0.07) |
| 9a (−) | MTA | MTA | 457.0 | 86.3 |
| | | | (6.34 ± 0.07) | |
| 9b (+) | MTA | 996 | MTA | 376 |
| | | (6 ± 0.05) | | (6.43 ± 0.06) |

| | 5-HT$_{2A}$ | 5-HT$_7$ | 5-HT$_{2C}$ | SERT |
|---|---|---|---|---|
| 2** | 391.3 | 265 | 1,184 | MTA |
| | | | (5.93 ± 0.06) | |
| 2** | 1,204 | 1.6 | MTA | 3192 |
| | (5.92 ± 0.09) | (8.8 ± 0.06) | | (5.5 ± 0.06) |
| 3** | 748 | 0.5 | 128 | >10,000 |
| | (6.1 ± 0.1) | (9.33 ± 0.06) | (6.89 ± 0.08) | (>5.0) |
| 4 | 916 | 7.5 | MTA | MTA |
| | (6 ± 0.1) | (8.12 ± 0.07) | | |
| 5 | 1,013 | 4.0 | 1,500 | MTA |
| | (5.99 ± 0.09) | (8.4 ± 0.07) | (5.82 ± 0.06) | |
| 6 | 1,329 | 4.9 | MTA | 1,564 |
| | (5.88 ± 0.04) | (8.31 ± 0.06) | | (5.81 ± 0.05) |
| 7 | 962.3 | 14.5 | 618.0 | 2,061 |
| | | | (6.21 ± 0.06) | |
| 8 | 525 | 26.0 | 2,847 | ND |
| | (6.28 ± 0.04) | (7.59 ± 0.05) | | |
| 9a (−) | 834 | 3.7 | MTA | MTA |
| | (6.08 ± 0.06) | | | |
| 9b (+) | 729 | 66.5 | 3,130 | MTA |
| | (6.14 ± 0.06) | | (5.5 ± 0.08) | |

Figure 23:
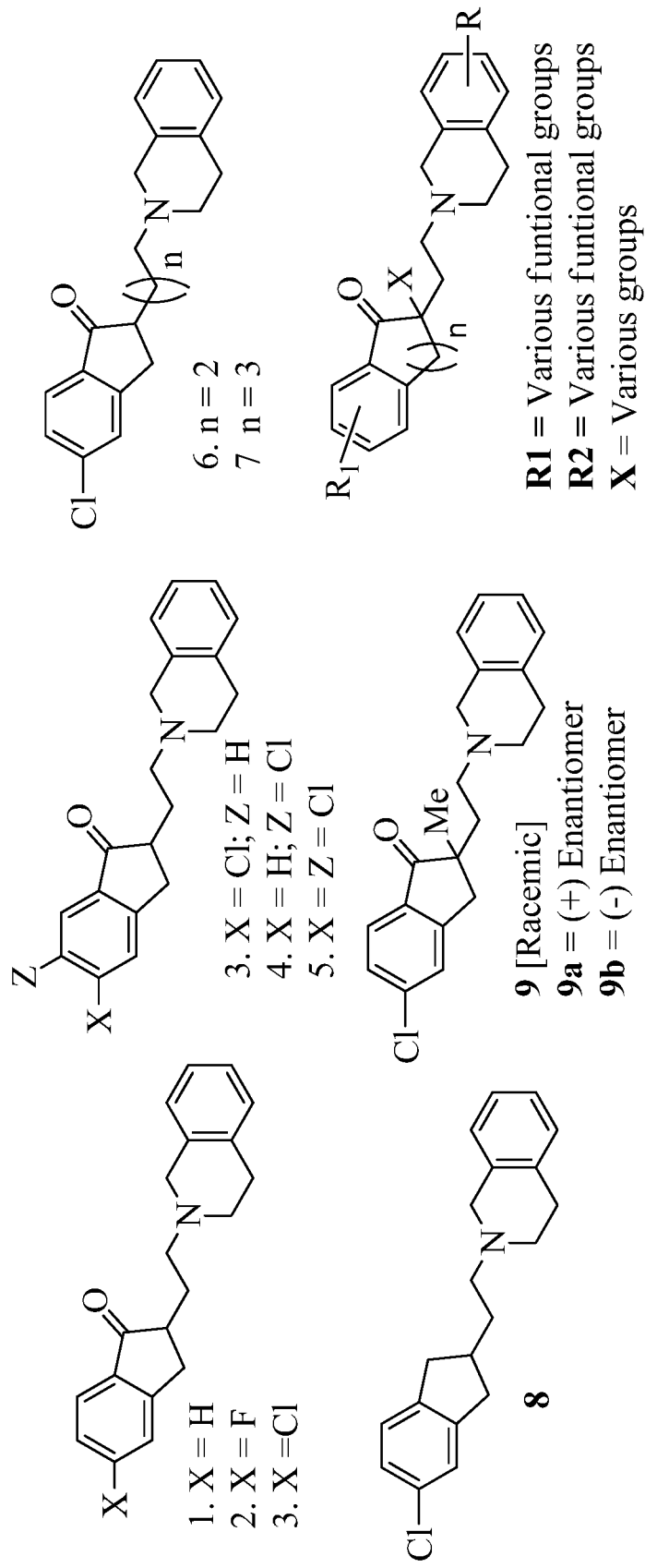
FIG. 23 illustrates structures of central nervous system receptor ligand analogs.

[a]Structures as shown in FIG. 23

I claim:

1. A serotonin receptor ligand, wherein the ligand has the formula:

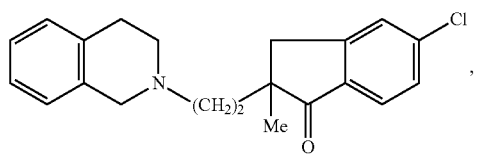

wherein the ligand is a racemic mixture, or an isolated enantiomer thereof.